United States Patent
Patel

(10) Patent No.: US 9,295,674 B2
(45) Date of Patent: Mar. 29, 2016

(54) METALLOPORPHYRIN NEUROLOGICAL TREATMENTS

(71) Applicant: The Regents of the University of Colorado, a body corporate, Denver, CO (US)

(72) Inventor: Manisha Patel, Englewood, CO (US)

(73) Assignee: The Regents of the University of Colorado, A Body Corporate, Denver, CO (US)

(*) Notice: Subject to any disclaimer, the term of this patent is extended or adjusted under 35 U.S.C. 154(b) by 5 days.

(21) Appl. No.: 14/291,798

(22) Filed: May 30, 2014

(65) Prior Publication Data

US 2015/0246057 A1 Sep. 3, 2015

Related U.S. Application Data

(63) Continuation of application No. PCT/US2012/067633, filed on Dec. 3, 2012.

(60) Provisional application No. 61/566,530, filed on Dec. 2, 2011.

(51) Int. Cl.
| | |
|---|---|
| A61K 31/555 | (2006.01) |
| F16C 11/10 | (2006.01) |
| A61B 17/17 | (2006.01) |
| A61B 19/00 | (2006.01) |
| A61K 45/06 | (2006.01) |
| A61K 31/409 | (2006.01) |
| A61K 31/44 | (2006.01) |

(52) U.S. Cl.
CPC ........... *A61K 31/555* (2013.01); *A61B 17/1746* (2013.01); *A61B 19/201* (2013.01); *A61K 31/409* (2013.01); *A61K 31/44* (2013.01); *A61K 45/06* (2013.01); *F16C 11/10* (2013.01); *Y10T 403/32426* (2015.01)

(58) Field of Classification Search
CPC .................................................. A61K 31/555
USPC ......................................................... 514/185
See application file for complete search history.

(56) References Cited

U.S. PATENT DOCUMENTS

| | | | | |
|---|---|---|---|---|
| 4,800,188 | A * | 1/1989 | Shepherd ....................... | 502/159 |
| 5,081,115 | A * | 1/1992 | Vreman et al. ................ | 514/185 |
| 5,994,339 | A | 11/1999 | Crapo et al. | |
| 6,066,628 | A * | 5/2000 | Stojiljkovic et al. .......... | 514/185 |
| 6,103,714 | A | 8/2000 | Fridovich et al. | |
| 6,479,477 | B1 | 11/2002 | Crapo et al. | |
| 6,544,975 | B1 | 4/2003 | Crapo et al. | |
| 6,916,799 | B2 | 7/2005 | Fridovich et al. | |
| 7,485,721 | B2 | 2/2009 | Batinic-Haberle et al. | |
| 8,470,808 | B2 | 6/2013 | Piganelli et al. | |
| 8,765,729 | B2 | 7/2014 | Crapo et al. | |
| 2004/0254155 | A1 * | 12/2004 | Bommer ........................ | 514/185 |
| 2011/0136775 | A1 | 6/2011 | Day et al. | |
| 2012/0289492 | A1 | 11/2012 | Patel et al. | |
| 2013/0225545 | A1 | 8/2013 | Patel et al. | |

FOREIGN PATENT DOCUMENTS

| | | |
|---|---|---|
| WO | WO-2010/016965 A2 | 2/2010 |
| WO | WO-2010/016965 A9 | 2/2010 |
| WO | WO-2011/028935 A2 | 3/2011 |
| WO | WO-2011/028935 A3 | 3/2011 |
| WO | WO-2013/130150 A2 | 9/2013 |
| WO | WO-2013/130150 A9 | 9/2013 |

OTHER PUBLICATIONS

Gould, N.S. et al. (Mar. 2009). "A role for mitochondrial oxidative stress in sulfur mustard analog 2-chloroethyl ethyl sulfide-induced lung cell injury and antioxidant protection," *J Pharmacol Exp Ther* 328(3):732-739.

Kachadourian, R. et al. (Jan. 2004). "Flavin-dependent antioxidant properties of a new series of meso-N,N'-dialkyl-imidazolium substituted manganese(III) porphyrins," *Biochem Pharmacol* 67(1):77-85.

Li, Q-Y et al. (Aug. 2001). "Dependence of excitotoxic neurodegeneration on mitochondrial aconitase inactivation," *J Neurochem* 78(4):746-755.

O'Neill, H.C. et al. (May 1, 2010, e-published Feb. 4, 2010). "Treatment with the catalytic metalloporphyrin AEOL 10150 reduces inflammation and oxidative stress due to inhalation of the sulfur mustard analog 2-chloroethyl ethyl sulfide," *Free Radic Biol Med* 48(9):1188-1196.

Patel, M. et al. (Feb. 1996). "Requirement for superoxide in excitotoxic cell death," *Neuron* 16(2):345-355.

Patel, M. (Sep. 1998). "Inhibition of neuronal apoptosis by a metalloporphyrin superoxide dismutase mimic," *J Neurochem* 71(3):1068-1074.

Patel, M. et al. (Sep. 1999). "Metalloporphyrin class of therapeutic catalytic antioxidants," *Trends Pharmacol Sci* 20(9):359-364.

Patel, M.N. (Aug. 2003). "Metalloporphyrins improve the survival of Sod2-deficient neurons," *Aging Cell* 2(4):219-222.

Sheng, H. et al. (Oct. 1, 2002). "Effects of metalloporphyrin catalytic antioxidants in experimental brain ischemia," *Free Radic Biol Med* 33(7):947-961.

Alcaro, S. et al. (Jul. 2007). "Molecular modelling and enzymatic studies of acetylcholinesterase and butyrylcholinesterase recognition with paraquat and related compounds," *SAR QSAR Environ Res* 18(5-6):595-602.

Chen, P. et al (Jan. 2008). "Catalytic metalloporphyrin protects against MPTP-induced parkinson's disease in mice," *Academic Journal of Second Military Medical University* 29(1):36-41.

Chen, P. et al. (Jun. 2008) "Catalytic metalloporphyrin protects against paraquat *neurotoxicity* in vivo," *Biomedical and Environmental Sciences* 21(3):233-238.

Deshpande, L.S. et al. (Aug. 2010, e-published May 23, 2010). "Development of a prolonged calcium plateau in hippocampal neurons in rats surviving status epilepticus induced by the organophosphate diisopropylfluorophosphate," *Toxicol Sci* 116(2):623-631.

McGovern, T. et al. (Mar. 1, 2011). "AEOL 10150: a novel therapeutic for rescue treatment after toxic gas lung injury," *Free Radic Biol Med* 50(5):602-608.

\* cited by examiner

Primary Examiner — Raymond Henley, III

(74) *Attorney, Agent, or Firm* — Mintz, Levin, Cohn, Ferris, Glovsky and Popeo, P.C.

(57) ABSTRACT

Methods and compositions for treating a subject suffering from exposure to a chemical threat agent are disclosed.

20 Claims, 16 Drawing Sheets

METALLOPORPHYRIN NEUROLOGICAL TREATMENTS

CROSS-REFERENCES TO RELATED APPLICATIONS

This application is a continuation of International Appl. No. PCT/US2012/067633, filed Dec. 3, 2012, which claims the benefit of U.S. Provisional Application No. 61/566,530, filed Dec. 2, 2011, the entire contents of each of which is hereby incorporated herein in its entirety and for all purposes.

STATEMENT AS TO RIGHTS TO INVENTIONS MADE UNDER FEDERALLY SPONSORED RESEARCH AND DEVELOPMENT

This invention was made with Government support under Grant Numbers R21NS072099 and R01NS039487 awarded by the National Institutes of Health and by the Counter ACT program. The Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Chemical warfare agents (e.g., chemical threat agents) are an immense threat to military personnel and civilians. The central nervous system (CNS) is a sensitive target for chemical toxicants that interact with receptors and signaling, e.g. nerve agents or organophosphate pesticides. Studies in the literature have established that controlling seizure activity and downstream consequences is critical for neuroprotection and survival after nerve agent exposure. Accordingly, there is a need to develop novel and efficacious neuroprotective countermeasures against chemical threat agents. Provided herein are compositions and methods directed to these and other problems in the art.

BRIEF SUMMARY OF THE INVENTION

There is provided, inter alia, a novel method for treating a subject suffering from exposure to a chemical threat agent, the method including administering to the subject an effective amount of a compound selected from:

a) a compound having the structure of Formula (I) or Formula (II),

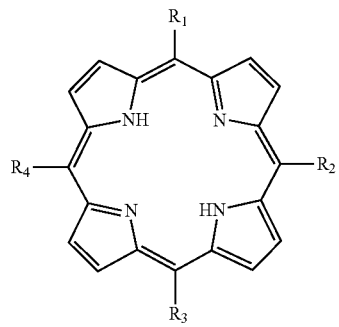

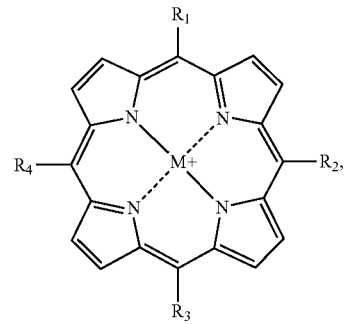

wherein $R_1$, $R_2$, $R_3$, and $R_4$ are each independently —$CF_3$, —$CO_2R_8$, —$COR_{8'}$,

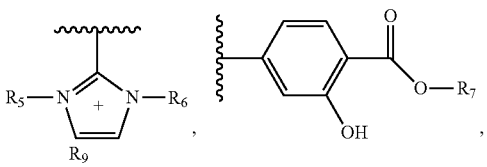

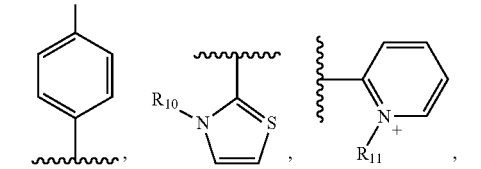

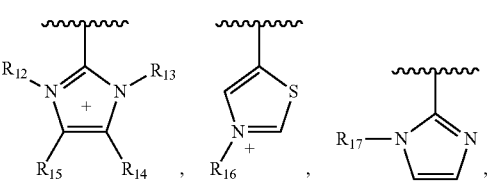

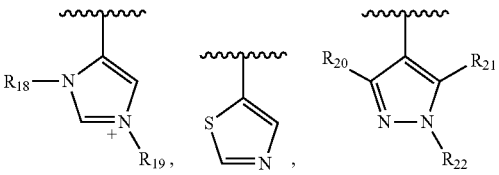

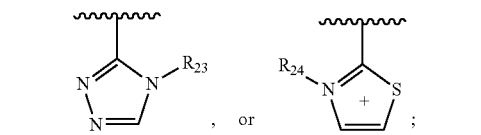

$R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are each independently hydrogen, halogen, —CN, —$CF_3$, —OH, —$NH_2$, —COOH, —$COOR_{25}$, —$CH_2COOR_{25}$, —$CH_2COOH$, an unsubstituted or substituted alkyl, unsubstituted or substituted heteroalkyl, unsubstituted or substituted cycloalkyl, unsubstituted or substituted heterocycloalkyl, unsubstituted or substituted aryl, or an unsubstituted or substituted heteroaryl; $R_{25}$ is an unsubstituted alkyl; and M is a metal;

b) a compound having the structure of one of Formulae (X)-(XV),
X
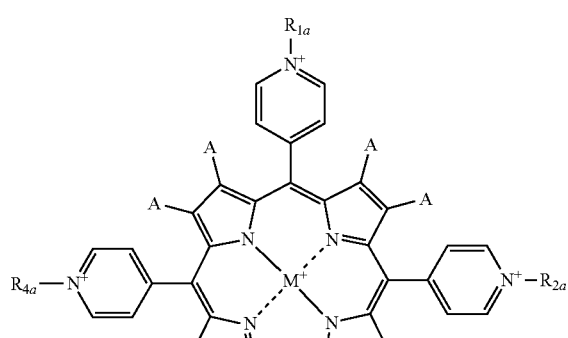
XI
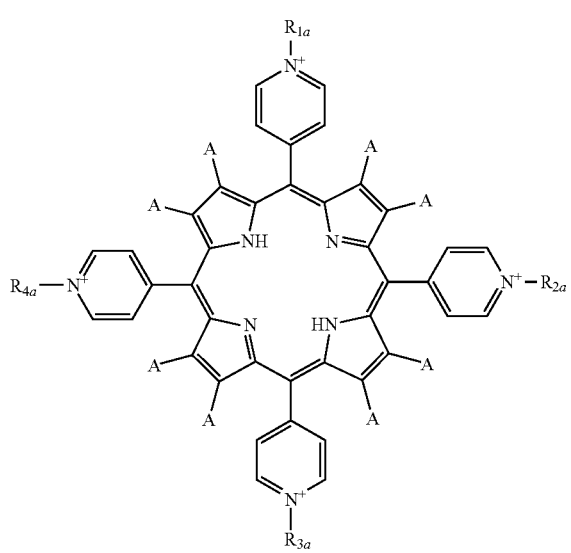
XII
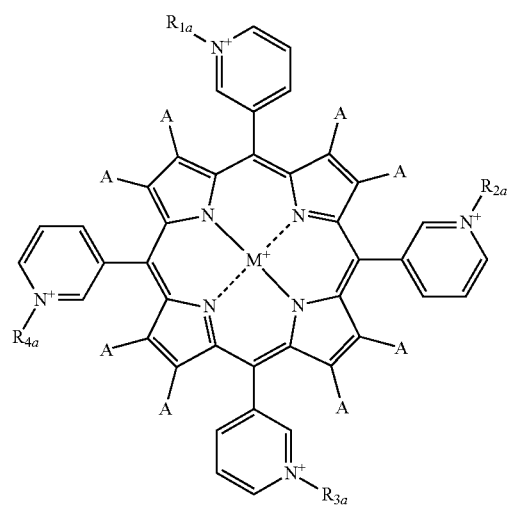
XIII
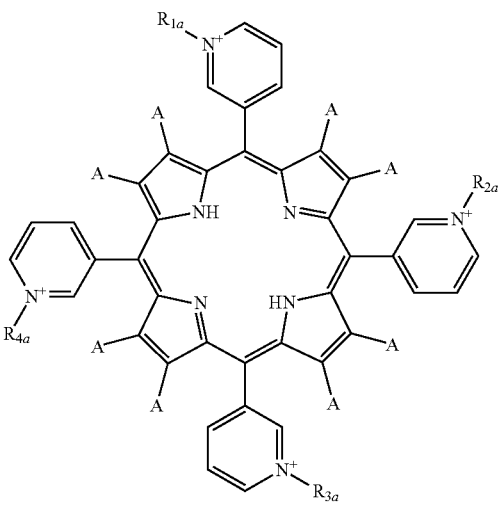
XIV
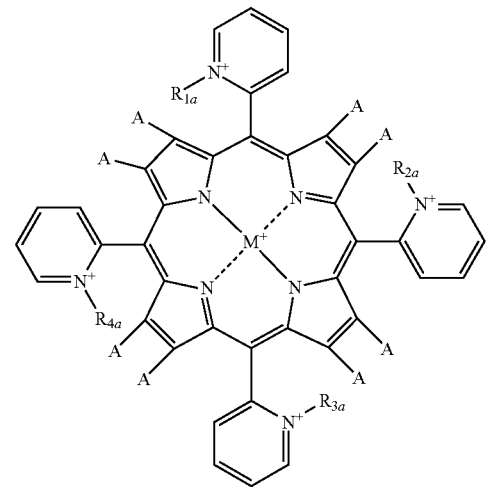
XV
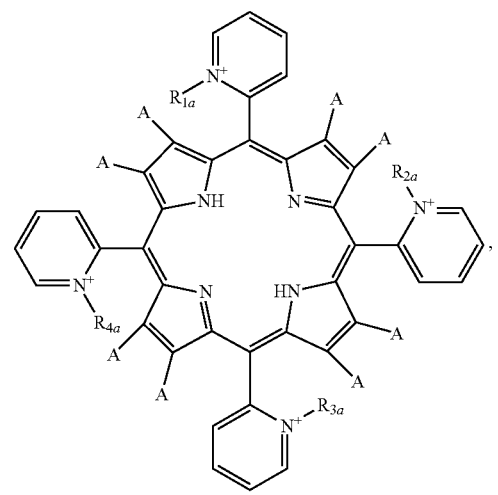
wherein $R_{1a}$, $R_{2a}$, $R_{3a}$, and $R_{4a}$ are independently —$(CH_2)_m CH_2 OX_1$ or —$(CH_2CH_2O)_n X_1$; m is 1-6; n is 3-50; $X_1$ is substituted or unsubstituted $C_{1-12}$ alkyl; M is a metal; and each A is, independently, hydrogen or an electron withdrawing group; and c) a compound having the structure of one of Formulae (XVI)-(XVII),

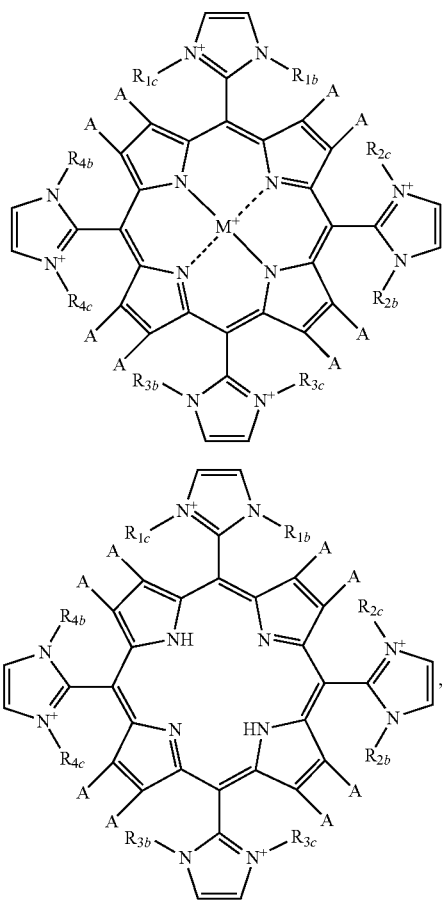

wherein at least one of $R_{1b}$ or $R_{1c}$, $R_{2b}$ or $R_{2c}$, $R_{3b}$ or $R_{3c}$, and $R_{4b}$ or $R_{4c}$ is, independently, $(CH_2)_pCH_2OX_2$ or $—(CH_2CH_2O)_qX_2$; the other one of $R_{1b}$ or $R_{1c}$, $R_{2b}$ or $R_{2c}$, $R_{3b}$ or $R_{3c}$, and $R_{4b}$ or $R_{4c}$ is, independently, a $C_{1-12}$ alkyl (straight chain or branched); p is 1-6; q is 3-50; $X_2$ is substituted or unsubstituted $C_{1-12}$ alkyl; M is a metal; and each A is, independently, hydrogen or an electron withdrawing group; wherein said chemical threat agent is an anti-cholinesterase agent, a GABA-agent or a metabolic poison.

In another aspect, there is provided a method for reducing brain injury in a subject in need thereof. The method includes administering to the subject an effective amount of a compound selected from any of Formulae (I)-(XVII), as disclosed herein.

BRIEF DESCRIPTION OF THE DRAWINGS

FIG. 1A: AEOL10150 [Formula (VII)] levels in plasma (right axis) and brain (left axis) of C57B16 mice are depicted with time after a single s.c. dose of AEOL10150 (15 mg/kg). Points represent mean+S.E.M. (n=3-4). Legend (FIG. 1A): Brain (closed circle); plasma (open circle). FIG. 1B: Histogram depicts TH-positive neurons in the SNpc of C57BL/6 mice counted by stereological analysis after injection of MPTP (15 mg/kg×3, s.c., 24 h intervals) alone or in the presence of AEOL10150 (15 mg/kg×3 s.c., daily for 3 days beginning 1 h prior to MPTP). FIG. 1C: Histogram depicts 4-HNE (4-hydroxynonenal) levels in the SN of the C57BL/6 mice after injection of MPTP (15 mg/kg×3, s.c., 24 h intervals) alone or in the presence of AEOL10150 (15 mg/kg×3 s.c., daily for 3 days) *p<0.01 vs. control, #p<0.01 vs. MPTP; one-way, ANOVA, n=6. Legend (FIGS. 1B-1C): Control (open); MPTP (closed); MPTP+AEOL10150 (diagonal lines).

(FIGS. 6A, 6D) control; (FIGS. 6B, 6E), kainate alone; (FIGS. 6C, 6F) kainate in presence of AEOL10150 treatment.

FIGS. 14A-14B depict histograms of GSH and GSSG concentrations, and GSH/GSSG ratio, and FIG. 14C depicts histogram of 3-nitrotyrosine/tyrosine (3NT/tyr) ratios in the hippocampus of the rat 24-hr (FIG. 14A and FIG. 14C left panel) or 48-h (FIG. 14B and FIG. 14C right panel) after either pilocarpine alone or in combination with AEOL10150 beginning 90 min after, 60 min after or 30 before and every 4 h thereafter until sacrifice (24 h or 48 h). Bars represent mean+S.E.M., $*p<0.05$ vs. saline treatment, $\# p<0.05$ vs. pilo alone treatment, one-way ANOVA, n=3-6 per group. Legend of histogram ordering: FIG. 14A: Control (A); pilocarpine (B); pilocarpine+AEOL10150 (90 min post-pilocarpine) (C); pilocarpine+AEOL10150 (60 min post-pilocarpine) (D); FIG. 14B: Control (E); pilocarpine (F); pilocarpine+AEOL10150 (90 min post-pilocarpine) (G); pilocarpine+AEOL10150 (60 min post-pilocarpine) (H); pilocarpine+AEOL10150 (30 min pre-pilocarpine) (I); FIG. 14C (left panel): Control (saline) (J); pilocarpine (K); pilocarpine+AEOL10150 (90 min post-pilocarpine) (L); pilocarpine+AEOL10150 (60 min post-pilocarpine) (M); FIG. 14C (right panel): Control (saline) (N); pilocarpine (O); pilocarpine+AEOL10150 (90 min post-pilocarpine) (P); pilocarpine+AEOL10150 (60 min post-pilocarpine) (Q); pilocarpine+AEOL10150 (30 min pre-pilocarpine) (R).

FIG. 15A is histogram depicting maximal respiratory capacity of rats treated with control, pilocarpine and saline, or pilocarpine and AEOL10150. n=5-8 rat/group. Histogram ordering (left to right): Control; pilocarpine+saline; pilocarpine+AEOL10150. FIG. 15B depicts time course of oxygen consumption rate (OCR, pmol/min).

FIGS. 16A-16D are photomicrographs of images of microglia (iba1) immunofluorescence in rat brain at 24 h after receiving saline (control (FIG. 16A), pilocarpine alone (FIG. 16B) or with AEOL10150 (5 mg/kg, s.c.) 60-min after pilocarpine (FIG. 16C) or 90-min after pilocarpine (FIG. 16D) every 4-hrs until sacrifice. FIG. 16E and FIG. 16F are histograms of quantitative analysis of the data provided in FIGS. 16A-16D. Bars=mean+S.E.M, $*p<0.01$ vs. saline; $\#p<0.05$ vs. pilocarpine; one way ANOVA, n=6 rats per group. Legend (FIGS. 16E-16F); Control (saline) (open); pilocarpine (closed); pilocarpine+AEOL10150 90-min post pilocarpine (diagonal lines upper left to lower right); pilocarpine (closed); pilocarpine+AEOL10150 60-min post pilocarpine (diagonal lines lower left to upper right).

DETAILED DESCRIPTION OF THE INVENTION

I. Definitions

Figure 1A:
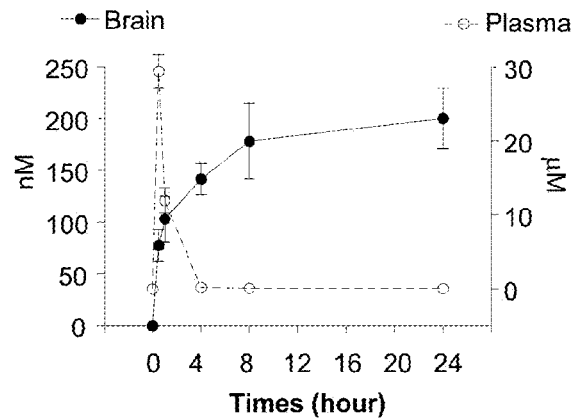
FIGS. 1A-1C.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—O$CH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R—SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2$O$CH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent, and each R substituent is optionally different. Where a particular R group is present in the description of a chemical genus (such as Formula (I)), a Roman alphabetic symbol may be used to distinguish each appearance of that particular R group. For example, where multiple $R_{27}$ substituents are present, each $R_{27}$ substituent may be distinguished as $R_{27A}$, $R_{27B}$, $R_{27C}$, $R_{27D}$, etc., wherein each of $R_{27A}$, $R_{27B}$, $R_{27C}$, $R_{27D}$, etc. is defined within the scope of the definition of $R_{27}$ and optionally differently. The term "about" in the context of a numeric value refers, absent express description otherwise, to the numeric value±10% thereof.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "effective amount," "therapeutically effective amount" and the like refer to the amount of an active agent sufficient to induce a desired biological result. That result may be alleviation of the signs, symptoms, or causes of a disease, or any other desired alteration of a biological system. The term "therapeutically effective amount" is used herein to denote any amount of a compound disclosed herein or formulation thereof which causes an improvement in a disease condition (e.g., exposure to a chemical threat agent) upon administration. The amount will vary with the condition being treated, the stage of advancement of the condition, and the type and concentration of formulation applied. Appropriate amounts in any given instance will be readily apparent to those skilled in the art or capable of determination by routine experimentation.

The terms "chemical agent," "chemical threat agent" and the like refer in the customary sense to compounds which elicit a pathological condition, e.g., incapacitation, convulsions, and the like, in a subject. Exemplary chemical threat agents include biotoxins, blister agents, blood agents, caustics (e.g., acids, bases), choking agents, lung agents, pulmonary agents, incapacitating agents, long-acting anticoagulants, metals, nerve agents, organic solvents, riot control agents, tear gas, toxic alcohols, and vomiting agents. The chemical threat agent may be a chemical weapon. The chemical threat agent may also be a nerve agent that disrupts the mechanism by which nerves transfer messages to organs. The disruption may be caused by inhibiting (i.e. lowering the activity of) acetylcholinesterase; e.g., sarin (isopropyl methylphosphonofluoridate), parathion (O,O-diethyl O-4-nitrophenyl phosphorothioate), aldicarb ((E)-2-methyl-2-(methylthio)propanal O-methylcarbamoyl oxime), and VX (S-2-(diisopropylamino)ethyl O-ethyl methylphosphonothioate). The chemical threat agent (e.g., nerve agent) may be a phosphorus-containing organic chemical (organophosphate). Some chemical threat agents (i.e., so-called "GABA-agents") interfere with GABA neuronal function and/or chloride channels, e.g., tetramethylene disulfotetramine, also known as "tetramine (TETS)" (2,6-dithia-1,3,5,7-tetraaza-tricyclo[3.3.1.13,7]decane 2,2,6,6-tetraoxide). Some chemical threat agents are so-called "metabolic poisons" or compounds which target the blood, as known in the art, e.g., cyanide, sodium fluoroacetate, arsenic trioxide, and strychnine. In one embodiment, chemical threat agents contemplated herein do not include agents as disclosed in International Publication No. WO 2010/016965 including a sulfur mustard, chlorine gas, phosgene, or 2-chloroethyl ethyl sulfide (CEES).

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of exposure to a chemical threat agent, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed. In one embodiment, the subject or patient is a child. In some embodiments, the subject or patient is a young child. In some embodiments, the subject or patient is an infant. In one embodiment, the subject or patient is an adult.

As defined herein, the term "child" or "children" as used herein means persons over the age of 3 years and prior to adolescence. As used herein, the term "young child" or "young children" means persons from the age of more than 12 months up to the age of three years. As used herein, the term "infant" means a person not more than 12 months of age. The term "adult" means persons past the age of adolescence.

II. Methods

There is provided a method for treating a subject suffering from exposure to a chemical threat agent. The chemical threat agent may be a nerve agent. The chemical threat agent may function as an anti-cholinesterase agent, a GABA-agent or a metabolic poison. The method includes administering to the subject an effective amount of a compound selected from the group having the structure of any of Formulae (I)-(XVII) disclosed herein.

In one embodiment, the compound has the structure of Formula (I) or Formula (II),

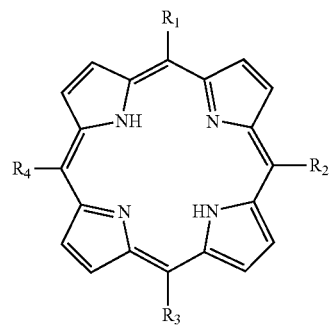
(I)

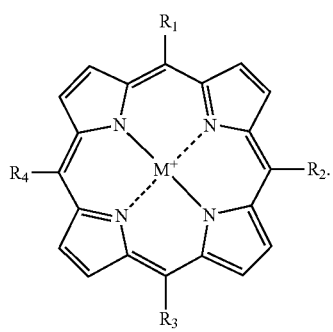
(II)

In Formula (I), the substituted porphyrin may be bound to a metal, e.g., Formula (II). The metal may be manganese, iron, cobalt, copper, nickel, or zinc, including ions thereof. For example, in Formula (II), or in any formula set forth herein, M is manganese, iron, cobalt, copper, nickel, or zinc, including ions thereof. Thus, in a specific embodiment, the metal is manganese and the compound has the structure of Formula (III):

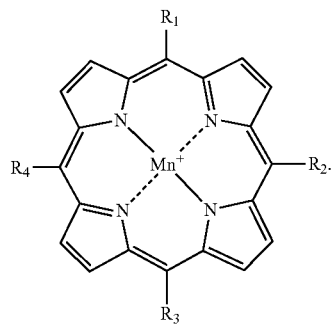
(III)

In any of Formulae (I)-(III), $R_1$, $R_2$, $R_3$, and $R_4$ are each independently —$CF_3$, —$CO_2R_8$,

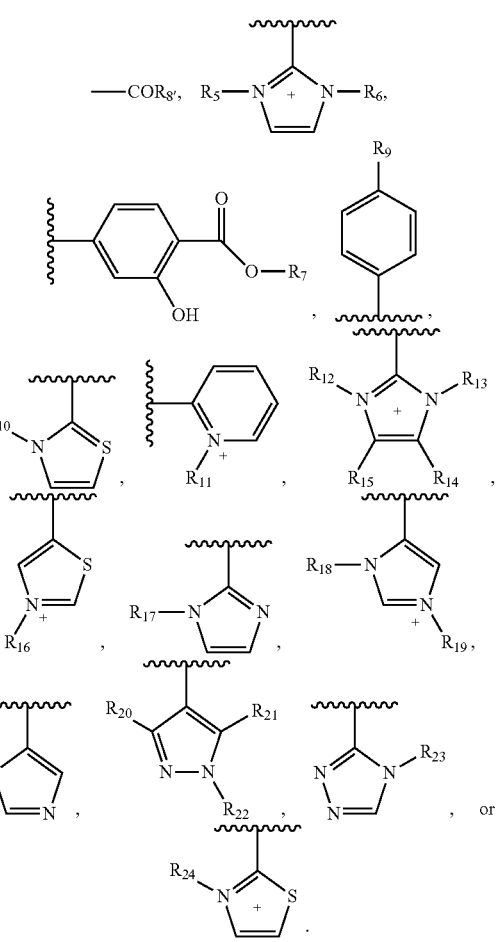

In one embodiment for Formulae (I)-(III), $R_1$, $R_2$, $R_3$, and $R_4$ may be

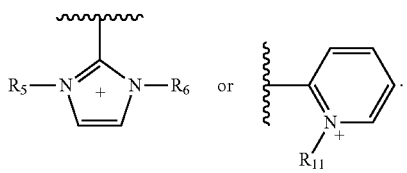

In one embodiment, $R_1$ and $R_3$ are independently $-CO_2R_8$ or $-COR_8$. $R_2$ and $R_4$ may independently be $-CF_3$ or

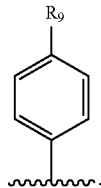

In one embodiment, $R_1$ and $R_3$ are independently $-CO_2R_8$, and $R_2$ and $R_4$ are $-CF_3$. In one embodiment, $R_1$ and $R_3$ are independently $-CO_2R_8$ and $R_2$ and $R_4$ are independently

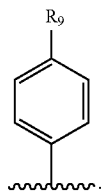

Where $R_1$, $R_2$, $R_3$, and $R_4$ contain a positive charge, one of skill will immediately recognize that an anionic compound or molecule will be present where the compound is in solution. Any applicable anionic compound are molecule may be used as a counterion to the positively charges substituents, including for example chloride, fluoride, sulfide, a sulfate, a carbonate, or a phosphate.

Further to this embodiment, $R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are each independently hydrogen, halogen, $-CN$, $-CF_3$, $-OH$, $-NH_2$, $-COOH$, $-COOR_{25}$, $-CH_2COOR_{25}$, $-CH_2COOH$, an unsubstituted or substituted alkyl, unsubstituted or substituted heteroalkyl, unsubstituted or substituted cycloalkyl, unsubstituted or substituted heterocycloalkyl, unsubstituted or substituted aryl, or an unsubstituted or substituted heteroaryl. $R_{25}$ is an unsubstituted alkyl. In one embodiment, $R_{25}$ is an unsubstituted alkyl such as $C_{1-10}$ alkyl (e.g., $-CH_3$ or a $C_{1-5}$ alkyl). M is a metal (e.g. is manganese, iron, cobalt, copper, nickel, or zinc).

In one embodiment, $R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ may each independently be hydrogen, halogen, $-CN$, $-CF_3$, $-OH$, $-NH_2$, $-COOH$, $-COOR_{25}$, $-CH_2COOR_{25}$, $-CH_2COOH$, substituted or unsubstituted $C_1$-$C_{10}$ (e.g., $C_1$-$C_6$) alkyl, substituted or unsubstituted 2 to 10 membered (e.g., 2 to 6 membered) heteroalkyl, substituted or unsubstituted $C_3$-$C_8$ (e.g., $C_5$-$C_7$) cycloalkyl, substituted or unsubstituted 3 to 8 membered (e.g., 3 to 6 membered) heterocycloalkyl, substituted or unsubstituted $C_5$-$C_8$ (e.g., $C_5$-$C_6$) aryl, or substituted or unsubstituted 5 to 8 membered (e.g., 5 to 6 membered) heteroaryl. In one embodiment, one or more of $R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ is unsubstituted. In one embodiment, $R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are independently hydrogen or a substituted or unsubstituted $C_1$-$C_{10}$ (e.g., $C_1$-$C_6$ or $C_1$-$C_3$) alkyl.

In one embodiment, $R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ may independently be hydrogen, halogen, $-CN$, $-CF_3$, $-OH$, $-NH_2$, and $R_{24}$, $-COOH$, $-COOR_{25}$, $-CH_2COOR_{25}$, $-CH_2COOH$, $R_{26}$-substituted or unsubstituted alkyl, $R_{26}$-substituted or unsubstituted heteroalkyl, $R_{26}$-substituted or unsubstituted cycloalkyl, $R_{26}$-substituted or unsubstituted heterocycloalkyl, $R_{26}$-substituted or unsubstituted aryl, or $R_{26}$-substituted or unsubstituted heteroaryl. $R_{26}$ is halogen, $-CN$, $-CF_3$, $-OH$, $-NH_2$, $-COOH$, $-COOR_{25}$, $-CH_2COOR_{25}$, $-CH_2COOH$, $R_{27}$-substituted or unsubstituted alkyl, $R_{27}$-substituted or unsubstituted heteroalkyl, $R_{27}$-substituted or unsubstituted cycloalkyl, $R_{27}$-substituted or unsubstituted heterocycloalkyl, $R_{27}$-substituted or unsubstituted aryl, or $R_{27}$-substituted or unsubstituted heteroaryl. In one embodiment, $R_{26}$ is halogen, $-CN$, $-CF_3$, $-OH$, $-NH_2$, $-COOH$, $R_{27}$-substituted or unsubstituted $C_1$-$C_{10}$ (e.g., $C_1$-$C_6$) alkyl, $R_{27}$-substituted or unsubstituted 2 to 10 membered (e.g., 2 to 6 membered) heteroalkyl, $R_{27}$-substituted or unsubstituted $C_3$-$C_8$ (e.g., $C_5$-$C_7$) cycloalkyl, $R_{27}$-substituted or unsubstituted 3 to 8 membered (e.g., 3 to 6 membered) heterocycloalkyl, $R_{27}$-substituted or unsubstituted $C_5$-$C_8$ (e.g., $C_5$-$C_6$) aryl, or $R_{27}$-substituted or unsubstituted 5 to 8 membered (e.g., 5 to 6 membered) heteroaryl. $R_{27}$ is halogen, $-CN$, $-CF_3$, $-OH$, $-NH_2$, $-COOH$, $-COOR_{25}$, $-CH_2COOR_{25}$, $-CH_2COOH$, $R_{28}$-substituted or unsubstituted alkyl, $R_{28}$-substituted or unsubstituted heteroalkyl, $R_{28}$-substituted or unsubstituted cycloalkyl, $R_{28}$-substituted or unsubstituted heterocycloalkyl, $R_{28}$-substituted or unsubstituted aryl, or $R_{28}$-substituted or unsubstituted heteroaryl. In one embodiment, $R_{27}$ is halogen, $-CN$, $-CF_3$, $-OH$, $-NH_2$, $-COOH$, $R_{28}$-substituted or unsubstituted $C_1$-$C_{10}$ (e.g., $C_1$-$C_6$) alkyl, $R_{28}$-substituted or unsubstituted 2 to 10 membered (e.g., 2 to 6 membered) heteroalkyl, $R_{28}$-substituted or unsubstituted $C_3$-$C_8$ (e.g., $C_5$-$C_7$) cycloalkyl, $R_{28}$-substituted or unsubstituted 3 to 8 membered (e.g., 3 to 6 membered) heterocycloalkyl, $R_{28}$-substituted or unsubstituted $C_5$-$C_8$ (e.g., $C_5$-$C_6$) aryl, or $R_{28}$-substituted or unsubstituted 5 to 8 membered (e.g., 5 to 6 membered) heteroaryl. $R_{28}$ is halogen, $-CN$, $-CF_3$, $-OH$, $-NH_2$, $-COOH$, $-COOR_{25}$, $-CH_2COOR_{25}$, $-CH_2COOH$, unsubstituted alkyl, unsubstituted heteroalkyl, unsubstituted cycloalkyl, unsubstituted heterocycloalkyl, unsubstituted aryl, or unsubstituted heteroaryl.

In one embodiment, $R_{26}$ and/or $R_{27}$ are substituted with a substituent group, a size-limited substituent group or a lower substituent group. In another embodiment, $R_{27}$ and $R_{28}$ are independently halogen, $-CN$, $-CF_3$, $-OH$, $-NH_2$, $-COOH$, $-COOR_{25}$, $-CH_2COOR_{25}$, $-CH_2COOH$, unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_8$ (e.g., $C_5$-$C_6$) aryl, or unsubstituted 5 to 8 membered (e.g., 5 to 6 membered) heteroaryl.

In one embodiment, each $R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$ may be the same or different and may each independently be an alkyl, and particularly a $C_{1-20}$ alkyl, more particularly a $C_{1-10}$ alkyl, and even more particularly a $C_{1-4}$ alkyl, and even more particularly, a methyl, an ethyl, or a propyl.

In one embodiments $R_8$ and $R_{8'}$ are independently hydrogen or an unsubstituted alkyl (e.g. an unsubstituted $C_{1-10}$ alkyl). $R_{8'}$ may also be hydrogen. $R_8$ may be methyl.

In one embodiment, $R_9$ is $-COOH$, $-COOR_{25}$, $-CH_2COOR_{25}$, or $-CH_2COOH$. $R_9$ may also be $-COOR_{25}$ or $-CH_2COOR_{25}$. In certain embodiments, $R_9$ is $-COOR_{25}$. In one related embodiment, $R_{25}$ is an unsubstituted $C_1$-$C_{10}$ alkyl, such as methyl.

In one embodiment, $R_1$ and $R_3$ may each independently be —$CO_2$—$CH_3$, or
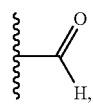
and $R_2$ and $R_4$ may each independently be —$CF_3$,
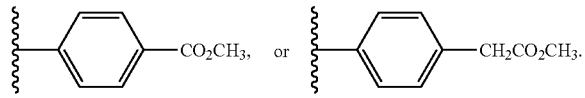
In one embodiment, the metalloporphyrin compound may have the formula:
In another specific embodiment, $R_1$, $R_2$, $R_3$, and $R_4$ may each independently be
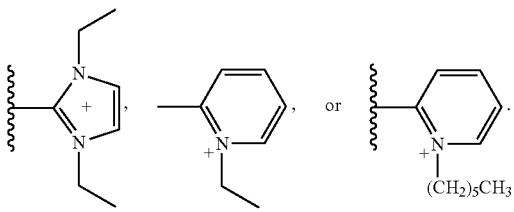
(IV)
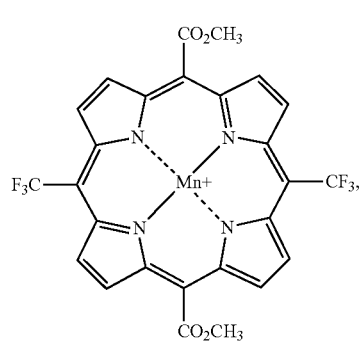
(V)
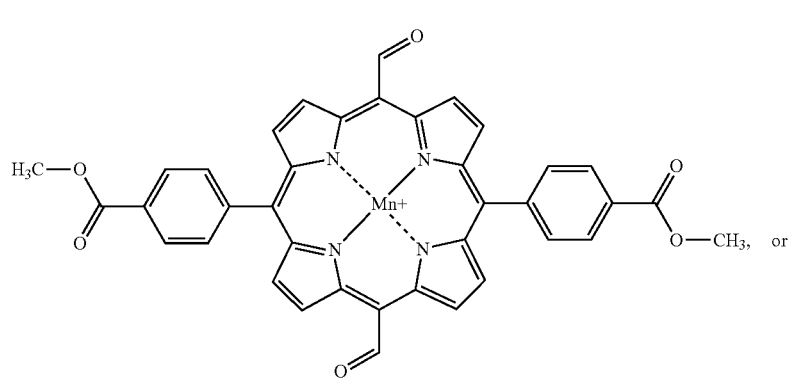
(VI)
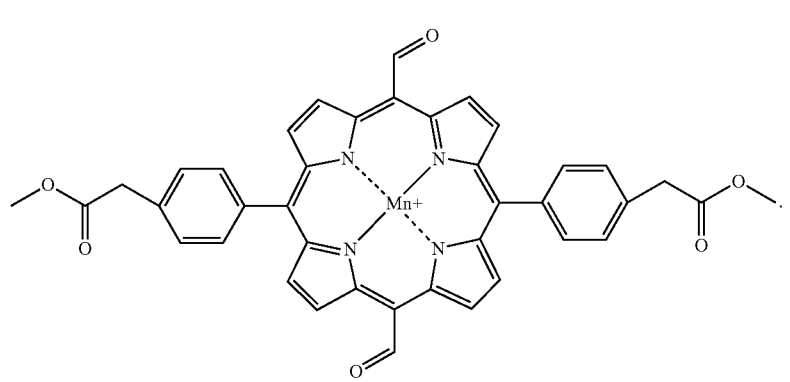

In one embodiment, the metalloporphyrin compound of the invention may have the formula:

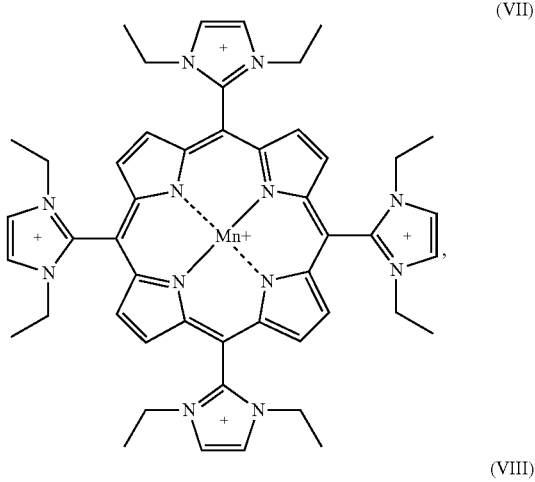

(VII)

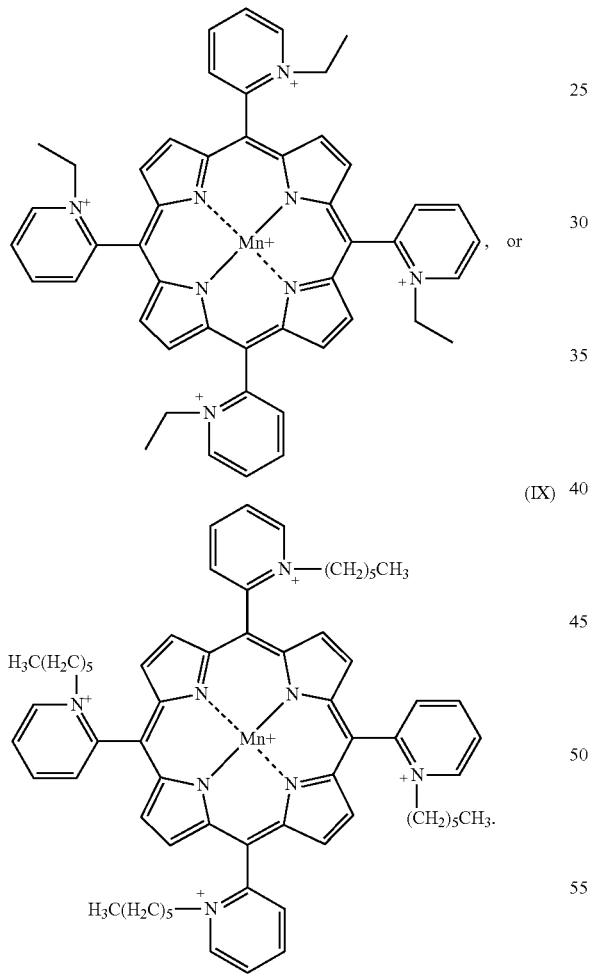

(VIII)

(IX)

In one embodiment, each substituted group described in the compounds above (e.g., Formulae (I)-(IX)) is substituted with at least one substituent group. More specifically, in one embodiment, each substituted alkyl, substituted heteroalkyl, substituted cycloalkyl, substituted heterocycloalkyl, substituted aryl, substituted heteroaryl, described in the compounds above (e.g., Formulae (I)-(IX)) are substituted with at least one substituent group. In one embodiment, at least one or all of these groups are substituted with at least one size-limited substituent group. Alternatively, at least one or all of these groups are substituted with at least one lower substituent group.

In one embodiment of the compounds described above (e.g., Formulae (I)-(IX)) each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

In one embodiment, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In one embodiment, the compound has the structure of one of Formulae (X)-(XV),

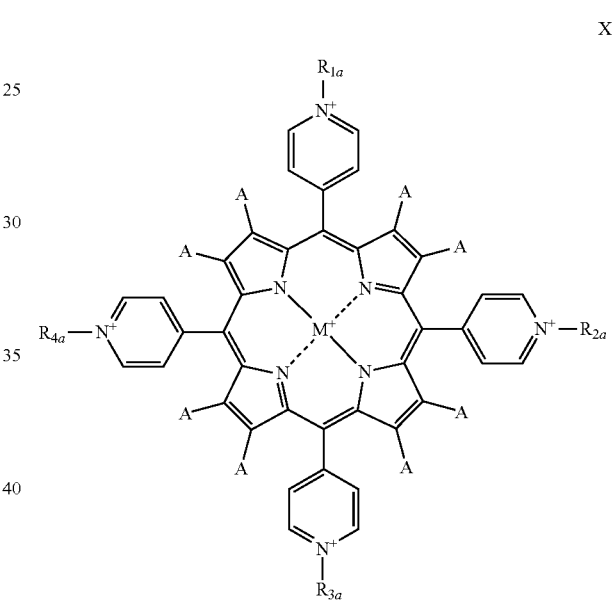

X

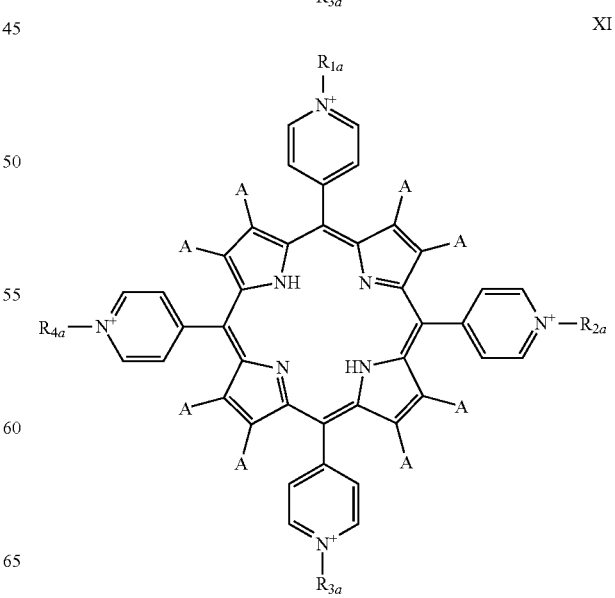

XI

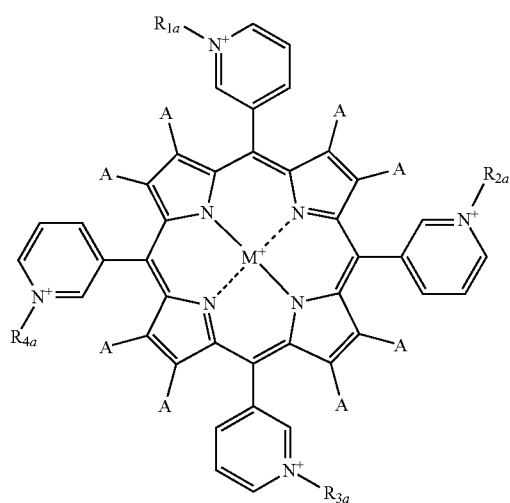

XII

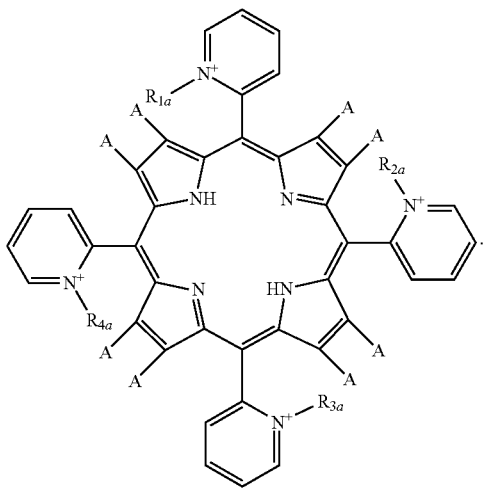

XV

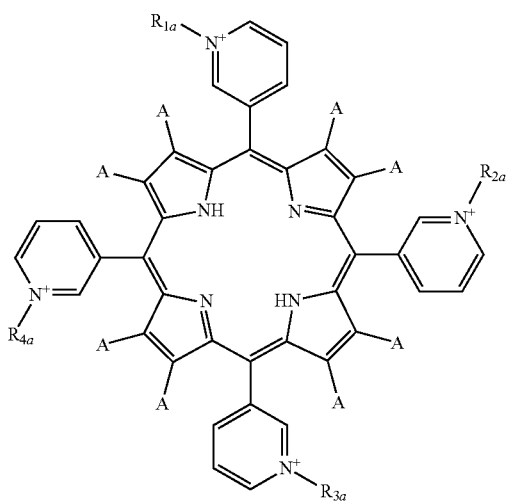

XIII

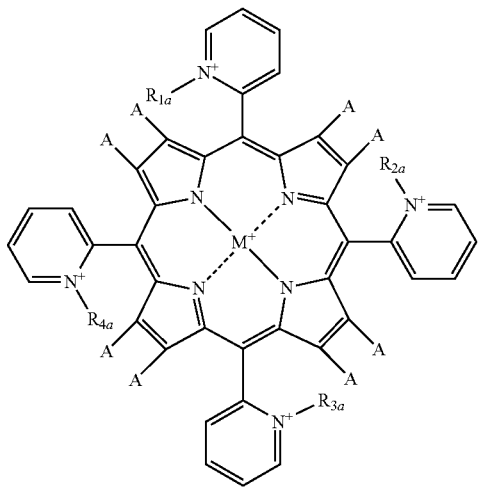

XIV

Further to this embodiment, $R_{1a}$, $R_{2a}$, $R_{3a}$, and $R_{4a}$ are independently —$(CH_2)_mCH_2OX_1$ or —$(CH_2CH_2O)_nX_1$; m is 1-6, preferably 1-4, more preferably 1 or 2; n is 3-50, preferably 3-10, more preferably 3, 4 or 5; $X_1$ is substituted or unsubstituted $C_{1-12}$ alkyl, preferably unsubstituted $C_{1-12}$ alkyl (straight chain or branched), more preferably $C_{1-8}$ alkyl, even more preferably $C_{1-4}$ alkyl; M is a metal (is manganese, iron, cobalt, copper, nickel, or zinc); and each A is, independently, hydrogen or an electron withdrawing group. Each $R_{1a}$, $R_{2a}$, $R_{3a}$, and $R_{4a}$ can be the same. The terms "electron withdrawing group," "EWG" and the like refer, in the usual and customary sense, to an atom or functional group that removes electron density from a system (e.g., a pi-system) thus making the system more electrophilic.

In one embodiment, the compound has the structure of one of Formulae (XVI)-(XVII),

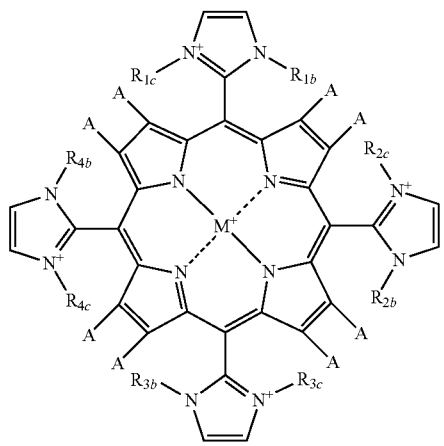

XVI

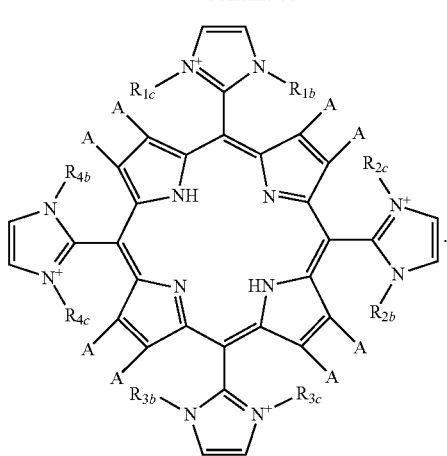

XVII

Further to this embodiment, at least one of $R_{1b}$ or $R_{1c}$, $R_{2b}$ or $R_{2c}$, $R_{3b}$ or $R_{3c}$, and $R_{4b}$ or $R_{4c}$ is, independently, —$(CH_2)_pCH_2OX_2$ or —$(CH_2CH_2O)_qX_2$; the other one of $R_{1b}$ or $R_{1c}$, $R_{2b}$ or $R_{2c}$, $R_{3b}$ or $R_{3c}$, and $R_{4b}$ or $R_{4c}$ is, independently, a $C_{1-12}$ alkyl (straight chain or branched), preferably a $C_{1-8}$ alkyl, more preferably a $C_1$, $C_2$, $C_3$ or $C_4$ alkyl; p is 1-6, preferably 104, more preferably 1 or 2; q is 3-50, preferably 3-10, more preferably 3, r or 5; $X_2$ is substituted or unsubstituted $C_{1-12}$ alkyl, preferably is $C_{1-12}$ alkyl (straight chain or branched), more preferably $C_{1-8}$ alkyl, even more preferably $C_{1-4}$ alkyl; M is a metal (e.g. is manganese, iron, cobalt, copper, nickel, or zinc); and each A is, independently, hydrogen or an electron withdrawing group. Advantageously, each $R_{1b}$, $R_{1c}$, $R_{2b}$, $R_{2c}$, $R_{3b}$, $R_{3c}$, $R_{4b}$ and $R_{4c}$ can be the same and is —$(CH_2CH_2O)_qX_2$.

When the compound is of Formulae (X)-(XVII), each A is, independently, hydrogen or an electron withdrawing group, for example, a halogen (e.g., CI, Br or F), $NO_2$, or CHO, preferably each A is hydrogen or halogen, more preferably at least one A is halogen and the remaining A's are hydrogen, still more preferably 1-4 A's are, independently, Cl or Br and the remaining A's are hydrogen. M is metal selected from the group consisting of manganese, iron, copper, cobalt, nickel and zinc (preferably manganese).

In one embodiment, each substituted group described in the compounds with structure of Formulae (X)-(XVII) is substituted with at least one substituent group. More specifically, in one embodiment, each substituted alkyl, substituted heteroalkyl, substituted cycloalkyl, substituted heterocycloalkyl, substituted aryl, substituted heteroaryl, described in the compounds with structure of Formulae (X)-(XVII) are substituted with at least one substituent group. In one embodiment, at least one or all of these groups are substituted with at least one size-limited substituent group. Alternatively, at least one or all of these groups are substituted with at least one lower substituent group.

In one embodiment of the compounds with structure of Formulae (X)-(XVII), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted het-erocycloalkyl is a substituted or unsubstituted 3 to 8 membered heterocycloalkyl. In one embodiment, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Further to any embodiment disclosed herein, the compound can be formed with a counterion Z, exemplified but not limited as follows for compounds of Formulae (X)-(XVII):

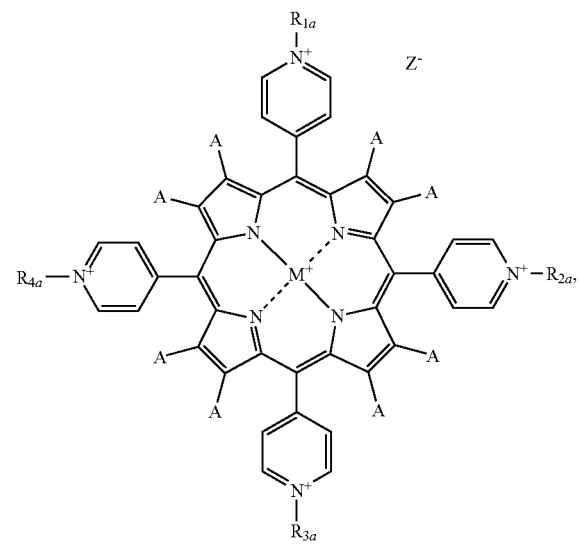

X

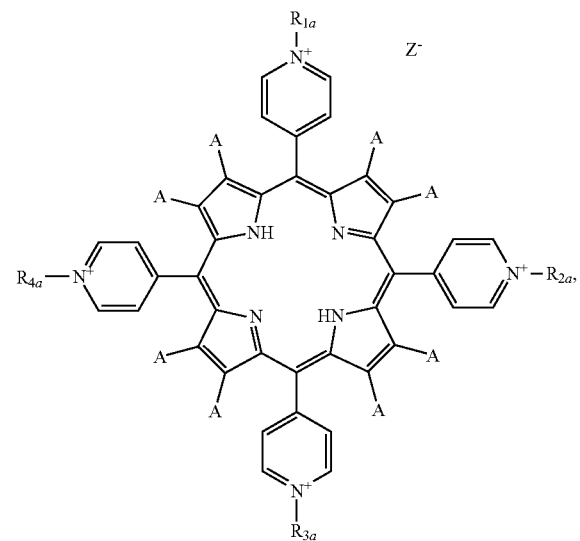

XI

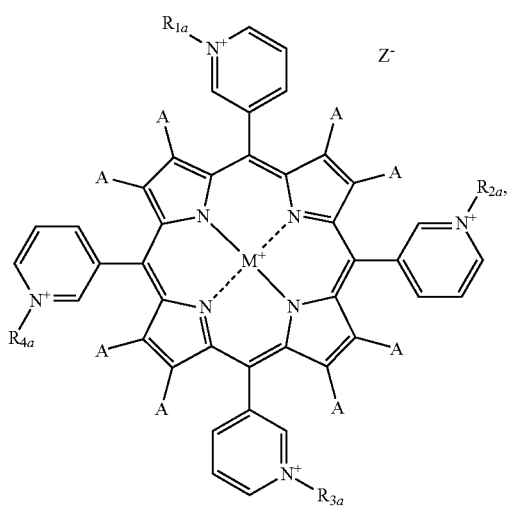

XII

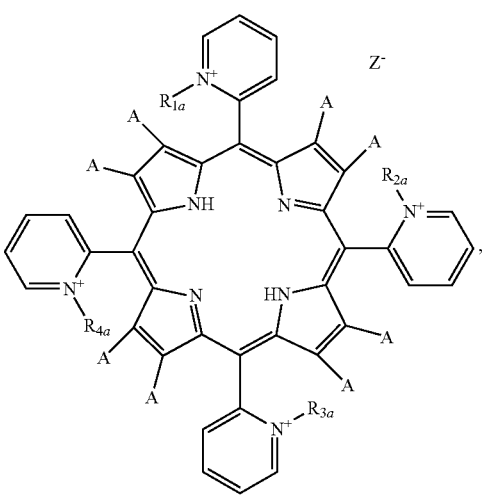

XV

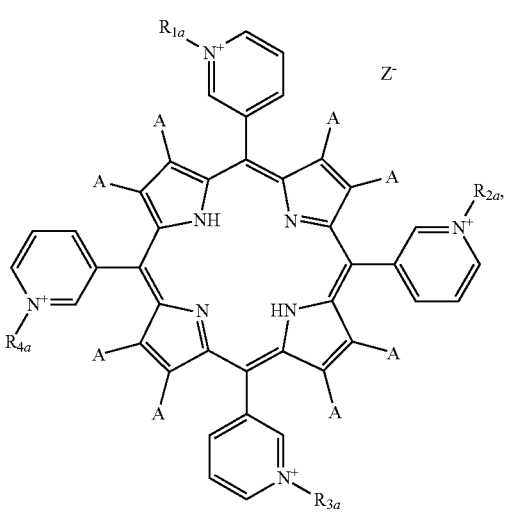

XIII

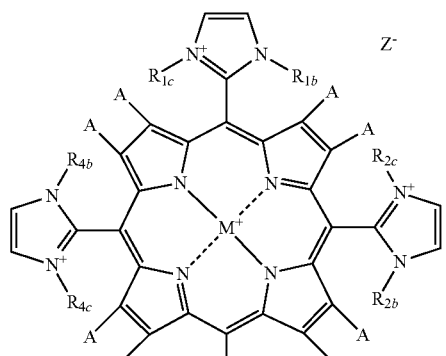

XVI and

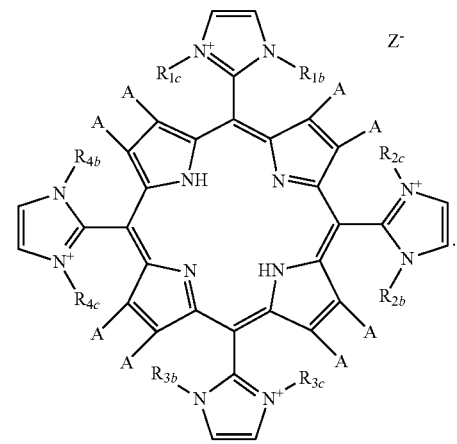

XVII

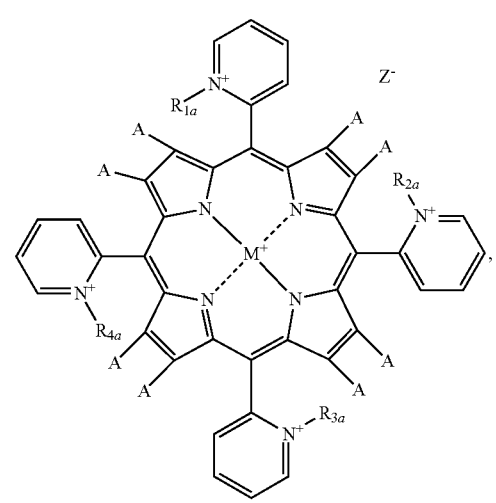

XIV

In one embodiment, a compound of Formula (I) can be formed with a counterion Z. In one embodiment, a compound of Formula (II) can be formed with a counterion Z. In one embodiment, a compound of Formula (III) can be formed with a counterion Z. In one embodiment, a compound of Formula (IV) can be formed with a counterion Z. In one embodiment, a compound of Formula (V) can be formed with a counterion Z. In one embodiment, a compound of Formula (VI) can be formed with a counterion Z. In one embodiment, a compound of Formula (VII) can be formed with a counterion Z. In one embodiment, a compound of Formula (VIII) can be formed with a counterion Z. In one embodiment, a compound of Formula (IX) can be formed with a counterion Z. In one embodiment, a compound of Formula (X) can be formed with a counterion Z. In one embodiment, a compound of Formula (XI) can be formed with a counterion Z. In one embodiment, a compound of Formula (XII) can be formed with a counterion Z. In one embodiment, a compound of Formula (XIII) can be formed with a counterion Z. In one embodiment, a compound of Formula (XIV) can be formed with a counterion Z. In one embodiment, a compound of Formula (XV) can be formed with a counterion Z. In one embodiment, a compound of Formula (XVI) can be formed with a counterion Z. In one embodiment, a compound of Formula (XVII) can be formed with a counterion Z.

The counterion Z is an anion, e.g., halogen (chloride, bromide, iodide), an organic anion base (e.g., acetate, and the like), an inorganic base (e.g., sulfide, sulfate, carbonate, phosphate), or the like.

In one embodiment, the compound has the structure of Formula (I). In one embodiment, the compound has the structure of Formula (II). Where the compound has the structure of Formula (II), in one embodiment the metal is manganese, iron, cobalt, copper, nickel, or zinc. In one embodiment, the metal is manganese.

Further to embodiments where the compound has the structure of Formula (I) or Formula (II), in one embodiment $R_1$, $R_2$, $R_3$, and $R_4$ are each

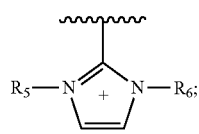

and $R_5$ and $R_6$ are independently unsubstituted alkyl (e.g., unsubstituted $C_1$-$C_{10}$ alkyl). $R_5$ and $R_6$ may independently be unsubstituted $C_1$-$C_6$ alkyl. $R_5$ and $R_6$ may independently be unsubstituted $C_1$-$C_5$ alkyl. $R_5$ and $R_6$ may independently be unsubstituted $C_1$-$C_4$ alkyl. $R_5$ and $R_6$ may independently be unsubstituted $C_1$-$C_3$ alkyl. $R_5$ and $R_6$ may independently be unsubstituted $C_1$-$C_2$ alkyl. In one embodiment, the compound has the structure of Formula (VII) following:

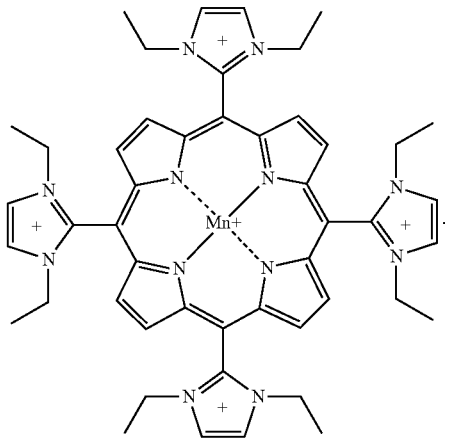

(VII)

Further to any embodiment disclosed herein, in one embodiment the chemical threat agent causes seizures, neuropathology, or both seizures and neuropathology. In one embodiment, the chemical threat agent causes seizures. In one embodiment, the chemical threat agent causes neuropathology.

In one embodiment, the chemical threat agent is a nerve agent. The terms "nerve agent" and the like refer, in the usual and customary sense, to compounds that disrupt the mechanism by which nerves transfer messages. In one embodiment, the nerve agent disrupts nerve signals by inhibiting acetylcholinesterase. The terms "anti-acetylcholinesterase," "anti-cholinesterase" and the like refer, in the usual and customary meaning, to an agent which can inhibit the activity of acetylcholinesterase (e.g., upon exposure to a chemical threat agent). Acetylcholinesterase, as well known in the art, hydrolyzes the neurotransmitter acetylcholine to afford an acetyl group and choline. In one embodiment, inhibition of acetylcholinesterase results in increased levels and duration of acetylcholine in a subject. The effects of anti-cholinesterases on the autonomic nervous system can include bradycardia, hypotension, hypersecretion, bronchoconstriction, GI tract hypermotility, and decreases intraocular pressure. Action at the neuromuscular junction can include prolonged muscle contraction. The effect of anti-cholinesterases can include seizure and/or neuropathology.

In one embodiment, the chemical threat agent is sarin, parathion, aldicarb or tetramine (TETS). In one embodiment, the chemical threat agent targets the blood. In one embodiment, the chemical threat agent is cyanide, sodium fluoroacetate, arsenic trioxide or strychnine.

In one embodiment, the effect of treating a subject suffering from exposure to a chemical threat agent lasts for a period of time (i.e., "effective period") following administration of a compound disclosed herein. In one embodiment, the effect lasts for an effective period of at least 10, 20, 30, 40, 50, 60, 90, 120, 150, 180, or 240 minutes, or even longer. In one embodiment, the effect lasts for an effective period of at least 1, 2, 3, 4, 5, 6, 12, or even 24 hours. In one embodiment, the effect lasts for at least 90 minutes.

In one embodiment, a compound with structure of Formulae (I)-(XVII), e.g., Formula (VII), is administered (e.g., parenterally or topically) at a dosage in the range of about 0.01 to 50 mg/kg/day, preferably, 0.1 to 10 mg/kg/day, more preferably 0.1 to 6 mg/kg/day. In one embodiment, dosage is about 1, 3, 5, 7, 10, 20, 50, 100, 200, 300, 400, 500, 600, 700, 800, 900, 1000 mg/day, or even more, in an adult.

In one embodiment, a compound with structure of Formulae (I)-(XVII) is administered in combination with any antidote or prophylactic to a chemical threat agent (e.g., nerve agent such as anti-cholinesterase agent, a GABA-agent or a metabolic poison).

The antidote or prophylactic can be an anticholinergic, an anti-seizure agent, or an acetylcholinesterase reactivating agent, or a combination of one, two or three of an anticholinergic, an anti-seizure agent, or an acetylcholinesterase reactivating agent. The anticholinergic can be an anticholinergic disclosed herein or known in the art. The anti-seizure agent can be an anti-seizure agent disclosed herein or known in the art. The acetylcholinesterase reactivating agent can be an acetylcholinesterase reactivating agent disclosed herein or known in the art. In one embodiment, the antidote or prophylactic agent restores acetylcholinesterase activity that is inhibited by the chemical threat agent.

In another aspect, there is provided a method for reducing brain injury in a subject in need thereof. The method includes administering to the subject an effective amount of a compound selected from any of Formulae (I)-(XVII), as disclosed above. In one embodiment, the compound has the structure of Formula (VII).

In one embodiment, the brain injury results from seizure. The seizure can result from exposure to a chemical threat agent. In one embodiment, the brain injury is cognitive dysfunction.

The terms "cognitive dysfunction" and the like refer, in the usual and customary sense, to a loss of intellectual functions such as thinking, remembering, reasoning, and the like.

In one embodiment, the brain injury results from seizure, the seizure results from exposure to a chemical threat agent, and the chemical threat agent is an anti-cholinesterase agent.

In one embodiment, a compound with structure of Formulae (I)-(XVII), e.g., Formula (VII), is administered (e.g., parenterally or topically) at a dosage in the range of about 0.01 to 50 mg/kg/day, preferably, 0.1 to 10 mg/kg/day, more preferably 0.1 to 6 mg/kg/day. In one embodiment, dosage is about 1, 3, 5, 7, 10, 20, 50, 100, 200, 300, 400, 500, 600, 700, 800, 900, 1000 mg/day, or even more, in an adult.

Further to the method for treating a subject suffering from exposure to a chemical threat agent, or the method for reducing brain injury in a subject in need thereof, in one embodiment the method further includes administering to the subject an anticholinergic agent. The terms "anticholinergic (noun)," "anticholinergic agent" and the like refer, in the usual and customary sense, to compounds that block the action of the neurotransmitter acetylcholine in the central and peripheral nervous system. Exemplary anticholinergics at the muscarinic receptor, i.e., "antimuscarinic agents" as known in the art, include atropine, benztropine, ipratropium, oxitropium, tiotropium, glycopyrrolate, oxybutinin, tolterodine, chlorphenamine, diphenhydramine, dimenhydrinate, and the like. Exemplary anticholinergics at the nicotinic receptor, i.e., "antinicotinic agents" as known in the art, include bupropion, hexamethonium, tubocurarine, dextromethorphan, mecamylamine, doxacurium, and the like.

In one embodiment, the anticholinergic agent is atropine. As well known in the art, atropine competitively blocks acetylcholine (ACh) at muscarinic receptor sites by competing for the muscarinic receptors. Thus, blockade of muscarinic receptor ameliorates increased levels of acetylcholine. In one embodiment, the preferred anticholinergic is less toxic than atropine in a human subject. Toxicity can be assessed by a variety of methods known in the art including calculation of $LD_{50}$, the toxic dose for 50% of a population.

In one embodiment, an anticholinergic agent is administered at a dosage of about 0.1, 0.2, 0.3, 0.4, 0.5, 1.0, 1.5, 2.0, 2.5, 3.0, 4.0, 5.0, 6.0 mg or even greater in an adult. Administration can be by bolus or sequential administration of smaller aliquots of anticholinergic agent, e.g., administration in rapid succession, e.g., 2, 4, 6, 8, 10, 15, 20 minutes part. Administration of anticholinergic agent can be repeated as needed to prevent or treat symptoms of parasympathomimetic activity, coma, and/or cardiovascular collapse, as known in the art. In one embodiment, atropine is administered at a dosage of about 0.1, 0.2, 0.3, 0.4, 0.5, 1.0, 1.5, 2.0, 2.5, 3.0, 4.0, 5.0, 6.0 mg or even greater in an adult. Dosages for children can be adjusted as necessary. For example, dosages for infants generally less than six months of age can be about 0.10, 0.15, 0.20, 0.25, 0.30, 0.35, 0.40, 0.45, 0.50, 0.55, 0.60, 0.65, 0.70, 0.75 mg, or more. Dosages can be administered by sequential administration of smaller aliquots of anticholinergic agent, e.g., atropine. Dosages for infants and children weighting 15 to 40 pounds may be 0.10, 0.20, 0.30, 0.40, 0.50, 0.60, 0.70, 0.80, 0.90, 1.00, 1.10, 1.20, 1.30, 1.40, 1.50 mg, or even greater. Dosages for children weighting 40 to 90 pounds may be about 0.20, 0.40, 0.60, 0.80, 1.00, 1.20, 1.40, 1.60, 1.80, 2.00, 2.20, 2.40, 2.60, 2.80, 3.00 mg, or even greater.

In one embodiment, the compound of Formula (VII) is administered in combination with an anticholinergic. In one embodiment, the anticholinergic is atropine.

Further to the method for treating a subject suffering from exposure to a chemical threat agent, or the method for reducing brain injury in a subject in need thereof, in one embodiment the method further includes administering to the subject an anti-seizure agent. The term "anti-seizure agent" and the like refer, in the usual and customary sense, to compounds useful to suppress the rapid and excessive firing of neurons as a preliminary to, or duration, a seizure. Exemplary anti-seizures agents include the benzodiazepines: clobazam, clonazepam, clorazepate, diazepam, midazolam, lorazepam, and the like. In one embodiment, the anti-seizure agent is a benzodiazepine. In one embodiment, the anti-seizure agent is diazepam. In one embodiment, the anti-seizure agent is midazolam.

In one embodiment, an anti-seizure agent is administered at a dosage of about 1, 2, 3, 4, 5, 6, 7, 8, 9, 10, 15, 20, 25, 30, 35, 40, 45, 50 mg, or even greater, in an adult. In one embodiment, an anti-seizure agent is administered at a dosage of about 10, 50, 100, 200, 300 400, 500 mg/kg, or even greater, in a child. In one embodiment, administration is intravenous (i.v.) or intramuscular (i.m.) In one embodiment, administration is intramuscular (i.m.) In one embodiment, the anti-seizure agent is diazepam which is administered at a dosage of about 1, 2, 3, 4, 5, 6, 7, 8, 9, 10, 12, 14, 16, 18, 20 mg, or even greater, in an adult. In one embodiment, the anti-seizure agent is midazolam which is administered at a dosage of about 1, 2, 3, 4, 5, 6, 7, 8, 9, 10, 12, 14, 16, 18, 20 mg, or even greater, in an adult.

In one embodiment, the compound of Formula (VII) is administered in combination with an anti-seizure agent. In one embodiment, the anti-seizure agent is diazepam. In one embodiment, the anti-seizure agent is midazolam.

Further to the method for treating a subject suffering from exposure to a chemical threat agent, or the method for reducing brain injury in a subject in need thereof, in one embodiment the method further includes administering to the subject in combination an anticholinergic agent and an anti-seizure agent, as disclosed herein.

In one embodiment, the administered compound has the structural of Formula (VII), and the method further includes administering to the subject in combination an anticholinergic agent and an anti-seizure agent, as disclosed herein. In one embodiment, the anticholinergic is atropine. In one embodiment, the anti-seizure agent is diazepam. In one embodiment, the anti-seizure agent is midazolam.

In one embodiment, administration of a compound with structure of Formulae (I)-(XVII), e.g., Formula (VII), in combination with an anticholinergic agent and an anti-seizure agent results in a synergistic benefit to the subject. The terms "synergistic," "synergistic benefit," "synergistic effect," "synergistic therapeutic effect," "synergistically effective amount" and the like in the context of co-administration of compounds described herein refer to a more than additive (e.g., supra-additive) response (e.g., biological response) when two or more compounds are administered with respect to the summed effects upon administration of each compound in the absence of the other compound or compounds. For example, if two compounds provide a synergistic therapeutic effect, then the therapeutic effect observed upon co-administration of both compounds is greater than the summed observed therapeutic effects when either compound is administered in the absence of the other compound. Likewise, a first amount of a first compound and a second amount of a second compound together provide a synergistically effective amount where the therapeutic effect observed upon co-administration of both compounds is greater than the summed observed therapeutic effects when either compound is administered in the absence of the other compound. Where a synergistic benefit is achieved, the pharmaceutically active agents are provided in a combined synergistic amount.

In one embodiment, administration of a compound with structure of Formulae (I)-(XVII), e.g., Formula (VII), in combination with an anticholinergic agent and an anti-seizure agent results is greater effectiveness (i.e., synergistic benefit wherein the compound and agents are provided in a combined synergistic amount) relative to the summed effects of 1) treatment by administration of a structure of Formulae (I)-(XVII) alone, and 2) treatment with an anticholinergic agent in combination with an anti-seizure agent alone. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or 95%.

In one embodiment, a compound with structure of Formulae (I)-(XVII), e.g., Formula (VII), is administered (e.g., parenterally or topically) at a dosage in the range of about 0.01 to 50 mg/kg, preferably 0.1 to 10 mg/kg, more preferably 1.0 to 6 mg/kg. The effect of this administration alone can be compared with the combined effect upon administration of an anticholinergic agent administered at a dosage of about 0.1, 0.2, 0.3, 0.4, 0.5, 1.0, 1.5, 2.0, 2.5, 3.0, 4.0, 5.0, or 6.0 mg, preferably in the range of about 2-6 mg, and an anti-seizure agent administered at a dosage of about 1, 2, 3, 4, 5, 6, 7, 8, 9, 10, 15, 20, 25, 30, 35, 40, 45, 50 mg, preferably in the range of about 10-30 mg. The effect of the ternary combination of a compound with structure of Formulae (I)-(XVII), the anticholinergic agent and the anti-seizure agent can be compared with the summed effects of the administration of a compound with structure of Formulae (I)-(XVII) alone, and the effect of the administration of the binary combination of anticholinergic agent and anti-seizure agent alone to quantitate a synergistic benefit. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or 95%.

In one embodiment, a compound with structure of Formulae (I)-(XVII), e.g., Formula (VII), is administered (e.g., parenterally or topically) at a dosage in the range of about 0.01 to 50 mg/kg, preferably 0.1 to 10 mg/kg, more preferably 1.0 to 6 mg/kg. An anticholinergic agent, preferably atropine, may be administered at a dosage of about 0.1, 0.2, 0.3, 0.4, 0.5, 1.0, 1.5, 2.0, 2.5, 3.0, 4.0, 5.0, or 6.0 mg, preferably in the range of about 2-6 mg. An anti-seizure agent, preferably diazepam or midazolam, may be administered at a dosage of about 1, 2, 3, 4, 5, 6, 7, 8, 9, 10, 15, 20, 25, 30, 35, 40, 45, 50 mg, preferably in the range of about 10-30 mg. The effect of the ternary combination of a compound with structure of Formulae (I)-(XVII), e.g., Formula (VII), the anticholinergic agent and the anti-seizure agent can be compared with the summed effects of the administration of a compound with structure of Formulae (I)-(XVII), e.g., Formula (VII), alone, and the effect of the administration of the binary combination of anticholinergic agent and anti-seizure agent alone to quantitate a synergistic benefit. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or 95%.

In one embodiment, a compound with structure of Formula (VII) is administered (e.g., parenterally or topically) at a dosage in the range of about 0.01 to 50 mg/kg, preferably 0.1 to 10 mg/kg, more preferably 1.0 to 6 mg/kg. Atropine may be administered at a dosage of about 0.1, 0.2, 0.3, 0.4, 0.5, 1.0, 1.5, 2.0, 2.5, 3.0, 4.0, 5.0, or 6.0 mg, preferably in the range of about 2-6 mg. Diazepam may be administered at a dosage of about 1, 2, 3, 4, 5, 6, 7, 8, 9, 10, 15, 20, 25, 30, 35, 40, 45, 50 mg, preferably in the range of about 10-30 mg. The effect of the ternary combination of a compound with structure of Formula (VII), atropine and diazepam can be compared with the summed effects of the administration of a compound with structure of Formula (VII) alone, and the effect of the administration of the binary combination of atropine and diazepam alone to quantitate a synergistic benefit. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or 95%.

In one embodiment, a compound with structure of Formula (VII) is administered (e.g., parenterally or topically) at a dosage in the range of about 0.01 to 50 mg/kg, preferably 0.1 to 10 mg/kg, more preferably 1.0 to 6 mg/kg. Atropine may be administered at a dosage of about 0.1, 0.2, 0.3, 0.4, 0.5, 1.0, 1.5, 2.0, 2.5, 3.0, 4.0, 5.0, or 6.0 mg, preferably in the range of about 2-6 mg. Midazolam may be administered at a dosage of about 1, 2, 3, 4, 5, 6, 7, 8, 9, 10, 15, 20, 25, 30, 35, 40, 45, 50 mg, preferably in the range of about 10-30 mg. The effect of the ternary combination of a compound with structure of Formula (VII), atropine and midazolam can be compared with the summed effects of the administration of a compound with structure of Formula (VII) alone, and the effect of the administration of the binary combination of atropine and midazolam alone to quantitate a synergistic benefit. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or 95%.

Further to the method for treating a subject suffering from exposure to a chemical threat agent, or the method for reducing brain injury in a subject in need thereof, in one embodiment the method further includes administering to the subject an acetylcholinesterase reactivating agent. The terms "acetylcholinesterase reactivating agent" the like refer, in the usual and customary sense, to compounds useful to regenerate catalytic activity at an acetylcholinesterase site which has become deactivated due to chemical reaction, e.g., with a chemical threat agent such as an acetylcholinesterase inhibitor. See e.g., Luo, C., et al., 2007, *Biochemistry* 46:11771-11779. Useful acetylcholinesterase reactivating agents are known in the art and include HI-6 ([(E)-[1-[(4-carbamoylpyridin-1-ium-1-yl)methoxymethyl]pyridin-2-ylidene]methyl]-oxoazaniumdichloride), pralidoxime (2-pyridine aldoxime methyl chloride (2-PAM), and obidoxime (1,1'-[oxybis(methylene)] bis {4-[(E)-(hydroxyimino)methyl]pyridinium}), and the like. See e.g., Dawson, R. M., 1994, *J. Appl. Toxicol.* 14:317-331; Koplovitz, I. & Stewart, J. R., 1994, *Toxicol. Lett.* 70:269-279; Marrs, T C, 1993, *Pharmac. Ther.* 58:51-66; Rousseaux, C. G. & Dua, A. K., 1989, *Can. J. Physiol. Pharmacol.*, 67:1183-1189. In one embodiment, the methods provided herein include administering a compound of Formulae (I)-(XVII) and 2-PAM (e.g., in a combined synergistic amount and achieving a synergistic benefit).

In one embodiment, acetylcholinesterase reactivating agent is administered at a dosage of about 5, 10, 15, 20, 25, 30, 35, 40, 50, 60, 70, 80, 90, 100 mg/kg, or even greater, in an adult, preferably about 30 mg/kg. In one embodiment, acetylcholinesterase reactivating agent is administered at a dosage of about 5, 10, 15, 20, 25, 30, 35, 40, 50, 60, 70, 80, 90, or 100 mg/kg, or even greater, in a child, preferably 20-50 mg/kg. In one embodiment, initial administration of acetylcholinesterase reactivating agent is followed by a maintenance infusion of 1-20 mg/kg/hr, preferably 5-10 mg/kg/hr.

Initial administration of acetylcholinesterase reactivating agent can be by any means, e.g., intravenous, intramuscular, or subcutaneous. In one embodiment, initial administration is intravenous as a continuous infusion at about 100, 200, 300, 400, 500, 600, 700 mg/hr, or even greater. In one embodiment, administration of acetylcholinesterase reactivating agent is sequential, wherein administration of aliquots of acetylcholinesterase reactivating agent takes place over a time span of, e.g., 5, 10, 15, 20, 25, 30, 40, 50, 60 minutes, or even longer. In a preferred embodiment, initial administration of acetylcholinesterase reactivating agent is intramuscular. In one embodiment, the acetylcholinesterase reactivating agent is pralidoxime. In one embodiment, pralidoxime is administered at a dosage of about 5, 10, 15, 20, 25, 30, 35, 40, 50 mg/kg, or even greater, in an adult. In a preferred embodiment, administration of pralidoxime is intramuscular, and the dosage of pralidoxime is 1-2 g.

In one embodiment, administration of a compound with structure of Formulae (I)-(XVII), e.g., Formula (VII), in combination with an anticholinergic agent, an anti-seizure agent, and an acetylcholinesterase reactivating agent results in a synergistic benefit relative to the summed effects of 1) treatment by administration of a structure of Formulae (I)-(XVII) alone, and 2) treatment alone with an anticholinergic agent in combination with an anti-seizure agent in further combination with an acetylcholinesterase reactivating agent. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or even 95%.

In one embodiment, a compound with structure of Formulae (I)-(XVII), e.g., Formula (VII), is administered (e.g., parenterally or topically) at a dosage in the range of about 0.01 to 50 mg/kg, preferably 0.1 to 10 mg/kg, more preferably 1.0 to 6 mg/kg. The effect of this administration alone can be compared with the combined effect upon administration of an anticholinergic agent administered at a dosage of about 0.1, 0.2, 0.3, 0.4, 0.5, 1.0, 1.5, 2.0, 2.5, 3.0, 4.0, 5.0, or 6.0 mg, preferably in the range of about 2-6 mg, an anti-seizure agent administered at a dosage of about 1, 2, 3, 4, 5, 6, 7, 8, 9, 10, 15, 20, 25, 30, 35, 40, 45, 50 mg, preferably in the range of about 10-30 mg, and an acetylcholinesterase reactivating agent at a dosage of about 5, 10, 15, 20, 25, 30, 35, 40, 50, 60, 70, 80, 90, 100 mg/kg. The effect of the quarnary combination of a compound with structure of Formulae (I)-(XVII), e.g., Formula (VII), the anticholinergic agent, the anti-seizure agent and the acetylcholinesterase reactivating agent can be compared with the summed effects of the administration of a compound with structure of Formulae (I)-(XVII) alone, and the effect of the administration of the ternary combination of anticholinergic agent, anti-seizure agent, and acetylcholinesterase reactivating agent alone to quantitate a synergistic benefit. In one embodiment, the synergistic benefit is at least 5%, 10%, 15%, 20%, 25%, 30%, 35%, 40%, 45%, 50%, 55%, 60%, 65%, 70%, 75%, 80%, 85%, 90%, or 95%. In one embodiment, the compound has the structure of Formula (VII), the anticholinergic agent is atropine, the anti-seizure agent is diazepam, and the acetylcholinesterase reactivating agent is pralidoxime. In one embodiment, the compound has the structure of Formula (VII), the anticholinergic agent is atropine, the anti-seizure agent is midazolam, and the acetylcholinesterase reactivating agent is pralidoxime.

In one embodiment, further to the method for treating a subject suffering from exposure to a chemical threat agent, or the method for reducing brain injury in a subject in need thereof, the method further includes administering to the subject a compound of Formulae (I)-(XVII), e.g., Formula (VII), and an acetylcholinesterase reactivating agent in combination with an anticholinergic agent and an anti-seizure agent. In one embodiment, the administered compound has the structural of Formula (VII), and the method further includes administering to the subject in combination an acetylcholinesterase reactivating agent, an anticholinergic agent and an anti-seizure agent, as disclosed herein. In one embodiment, the anticholinergic is atropine. In one embodiment, the anti-seizure agent is diazepam. In one embodiment, the anti-seizure agent is midazolam. In one embodiment, the acetylcholinesterase reactivating agent is pralidoxime.

Further to the method for treating a subject suffering from exposure to a chemical threat agent, or the method for reducing brain injury in a subject in need thereof wherein the brain injury results from seizure and the seizure results from exposure to a chemical threat agent, in one embodiment administration of a compound having the structure of any one of Formulae (I)-(XVII), e.g., Formula (VII), occurs prior to the exposure to the chemical threat agent. In one embodiment, administration of a compound of any one of Formulae (I)-(XVII) occurs at least 10, 20, 30, 40, 50, 60, 70, 80, 90, 100, 110, 120 min, or even longer, prior to exposure to the chemical threat agent. In one embodiment, administration of a compound of any one of Formulae (I)-(XVII) occurs at least 30 min prior to exposure to the chemical threat agent. In one embodiment, administration of a compound of any one of Formulae (I)-(XVII) occurs at least 60 min prior to exposure to the chemical threat agent. In one embodiment, administration of a compound of any one of Formulae (I)-(XVII) occurs at least 90 min prior to exposure to the chemical threat agent. In one embodiment, the compound has the structure of Formula (VII).

Further to the method for reducing brain injury in a subject in need thereof, the effect of reducing the brain injury lasts for at least 30, 60, 90, 120, 180, 240, 300 min, or even longer, following administration of a compound of Formulae (I)-(XVII). In one embodiment, the effect of reducing the brain injury lasts at least 30 min. In one embodiment, the effect of reducing the brain injury lasts at least 60 min. In one embodiment, the effect of reducing the brain injury lasts at least 90 min. In one embodiment, the effect of reducing the brain injury lasts at least 120 min. In one embodiment, the compound has the structure of Formula (VII).

Further to the method for reducing brain injury in a subject in need thereof, in one embodiment the compound has the structure of Formula (I) or Formula (II). In one embodiment, the compound has the structure of Formula (II). In one embodiment, the metal is manganese, iron, cobalt, copper, nickel, or zinc. In one embodiment, the metal is manganese. In one embodiment, for the compound with structure of Formula (I) or Formula (II), $R_1$, $R_2$, $R_3$, and $R_4$ are each

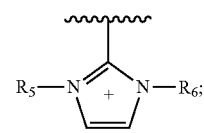

and $R_5$ and $R_6$ are independently unsubstituted alkyl. In one embodiment, the compound has the structure of Formula (VII).

III. Pharmaceutical Compositions

The compounds described above, metal bound and metal free forms, can be formulated into pharmaceutical compositions suitable for use in the present methods. Such compositions include the active agent (metalloporphyrin compounds) together with a pharmaceutically acceptable carrier, excipient or diluent. The composition can be present in dosage unit form for example, tablets, capsules or suppositories. The composition can also be in the form of a sterile solution, e.g., a solution suitable for injection (e.g., subcutaneous, i.p. or i.v.) or nebulization. Compositions can also be in a form suitable for ophthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought. The compounds can also be encapsulated in lysosomes and thereby targeted to enhance delivery.

In one embodiment, the metalloporphyrin compound may form part of a pharmaceutical composition. The pharmaceutical composition may include a metallophorphyrin compound, as disclosed herein, and a pharmaceutically acceptable excipient. A "pharmaceutically acceptable excipient" includes pharmaceutically and physiologically acceptable, organic or inorganic carrier substances suitable for enteral or parenteral administration that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinyl pyrrolidone. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the active agent.

In one embodiment, the treatment compound (e.g., metalloporphyrin compounds or metalloporphyrin catalytic antioxidant compositions as set forth herein) forms part of a pharmaceutical composition, wherein said pharmaceutical composition comprises the treatment compound and a pharmaceutical acceptable excipient. In one embodiment, the pharmaceutical composition includes a permeabilizer (e.g., a salicylate, a fatty acid, or a metal chelator).

The pharmaceutical composition can be formulated for any route of administration, including enteral, oral, sublingual, buccal, parenteral, ocular, intranasal, pulmonary, rectal, intravaginal, transdermal, and topical routes. Parenteral administration includes, but is not limited to, intravenous, intramuscular, subcutaneous, intradermal, intraperitoneal, intrasternal, intraarterial injection and infusion.

The pharmaceutical composition can be formulated for immediate release or modified release, e.g., modified, sustained, extended, delayed, or pulsatile release, using known methods and excipients.

In one embodiment, the pharmaceutical composition is formulated as a topical composition, an injectable composition, an inhalant, a sustained release composition, or an oral composition. The treatment compound is preferably formulated for parenteral administration, e.g., by subcutaneous injection. If subcutaneous or an alternative type of administration is used, the compounds may be derivatized or formulated such that they have a protracted profile of action.

In another embodiment, the pharmaceutical composition is formulated a targeted micelle, a degradable polymeric dosage form, a porous microsphere, a polymer scaffold, a liposome, or a hydrogel.

The treatment compound may be formulated according to known methods to prepare pharmaceutically useful compositions. An exemplary formulation would be one that is stable and reconstituted with an appropriate diluent or an aqueous solution of high purity with optional pharmaceutically acceptable carriers, preservatives, excipients or stabilizer. See e.g., Remington, 1980, PHARMACEUTICAL SCIENCES, 16th edition. The pharmaceutical composition may include a pharmaceutically acceptable buffer to achieve a suitable pH for stability and for administration.

For parenteral administration, the treatment compound can be formulated in a unit dosage injectable form (solution, suspension, or emulsion) with a pharmaceutically acceptable carrier. Preferably, one or more pharmaceutically acceptable anti-microbial agents may be added, such as phenol, m-cresol, benzyl alcohol, and the like as known in the art.

In one embodiment, one or more pharmaceutically acceptable salts (e.g., sodium chloride), sugars (e.g., mannitol), or other excipients (e.g., glycerin) may be added to adjust the ionic strength or tonicity.

The dosage of the composition to be administered can be determined without undue experimentation and will be dependent upon various factors including the nature of the active agent (including whether metal bound or metal free), the route of administration, the patient, and the result sought to be achieved. A suitable dosage of mimetic to be administered (e.g., i.v. or topically) can be expected to be in the range of about 0.01 to 50 mg/kg/day, preferably, 0.1 to 10 mg/kg/day, more preferably 0.1 to 6 mg/kg/day. For aerosol administration, it is expected that doses will be in the range of 0.001 to 5.0 mg/kg/day, preferably, 0.01 to 1 mg/kg/day. Suitable doses will vary, for example, with the compound and with the result sought.

The concentration of compound presentation in a solution used to treat cells/tissues/organs in accordance with the methods disclosed herein can be readily determined and will vary with the active agent, the cell/tissue/organ and the effect sought.

Certain aspects disclosed herein can be described in greater detail in the non-limiting examples that follows.

IV. Examples

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1

Neuroprotection by a Catalytic Antioxidant Following Pilocarpine- and Kainate-Induced Status Epilepticus Abstract Rationale:

Without wishing to be bound by any theory, it is believed that status epilepticus (SE) results in profound oxidative stress and mitochondrial dysfunction. Reactive oxygen species are mediators of mitochondrial dysfunction that may be active in promoting neuronal death associated with the development of temporal lobe epilepsy (TLE). A goal of this study was to determine if mitochondrial oxidative stress contributes to hippocampal neuronal death following SE and whether a synthetic catalytic antioxidant administered post-SE would provide neuroprotection in two chemoconvulsant models.

Methods:

Adult Sprague-Dawley rats were injected with vehicle, kainate (11 mg/kg) or pilocarpine (340 mg/kg) to initiate SE followed by treatment with vehicle or a synthetic metalloporphyrin catalytic antioxidant, AEOL 10150 (5 mg/kg, s.c.), beginning 60-90 min post-SE onset and every 4-6 hr until sacrifice at 48 h. Evidence for neuroprotection in the hippocampus of chemoconvulsant/AEOL 10150-treated rats was measured at 48 h post-SE using Fluoro-Jade B staining, a marker of degenerating neurons, and Image J analysis. Oxidative damage was assessed 24 h post-SE by measurement of 3-nitrotyrosine/tyrosine (3NT/tyr) and reduced/oxidized glutathione (GSH/GSSG) ratios, respectively by HPLC methods. The concentrations of AEOL 10150 in the rat brain were also determined.

Results:

Fluoro-Jade B staining indicative of cell injury was prevalent throughout the hippocampus of pilocarpine and kainate-treated rats at 48 h post-SE. In pilocarpine-treated rats receiving AEOL 10150, cell injury decreased by approximately 40% in CA1, and 60% in CA3 and hilus. In kainate-treated rats receiving AEOL 10150, cell injury decreased by approximately 40% in CA3 and hilus. AEOL 10150 significantly decreased oxidative stress indices (3-NT/tyr and GSH/GSSG ratios) in the hippocampus of pilocarpine-treated rats. Measurement of AEOL 10150 levels in the brain revealed its ability to achieve neuroprotective concentrations in the hippocampus and cortex following systemic administration.

Conclusions:

These data demonstrate the ability of a catalytic metalloporphyrin antioxidant to inhibit oxidative damage and provide neuroprotection in the hippocampus when administered 60-90 minutes following SE onset. The results suggest that oxidative stress may be a potential target for neuroprotection following SE.

Introduction

The central nervous system is a sensitive target for chemical toxicants that interact with receptors and signaling e.g. nerve agents or organophosphate pesticides. Studies in the literature have established that controlling seizure activity and downstream consequences is critical for neuroprotection and survival after nerve agent exposure. Recent efforts by the NIH CounterAct program to develop medical countermeasures have identified AEOL10150 as a lead compound with broad efficacy against multiple chemical threats. AEOL10150 is a catalytic antioxidant with a wide spectrum of activity against superoxide radicals ($O_2^-$.), hydrogen peroxide ($H_2O_2$), peroxynitrite ($ONOO^-$), and lipid peroxyl radicals. Work by our laboratories over the past decade demonstrates the efficacy of metalloporphyrins in numerous cell and animal models of neuronal injury. We have also established that oxidative stress is a critical consequence of prolonged seizures and contributes to seizure-induced neuronal death. Since elicitation of seizure activity is an important mechanism of several chemical threat agents e.g. nerve agents and organophosphate pesticides, it is important to determine whether AEOL10150 exerts neuroprotection against such agents. A goal of this study was to determine if AEOL10150 exerted neuroprotection against pilocarpine and kainate-induced seizures when administered 90 minutes after injection of convulsants.

A present goal is to determine if mitochondrial oxidative stress contributes to hippocampal neuronal death following SE and whether a synthetic catalytic antioxidant administered post-SE would provide neuroprotection in two chemoconvulsant models.

Methods

Animal.

Male Sprague-Dawley rats were treated with pilocarpine hydrochloride (340 mg/kg) i.p. after pre-treatment with methyl-scopolamine (1 mg/kg) i.p. or kainate (11 mg/kg, s.c.) to induce status epilepticus (SE). The animals were treated by saline or AEOL 10150 (5 mg/kg) s.c. at 90 minutes post-SE and every 4 hours thereafter until being sacrificed. Oxidative stress was measured at 24 h post-SE and neurons death was assessed by Fluoro-Jade B staining at 48 h post-SE.

Monitoring Behavioral Seizures.

Behavioral seizure severity during SE was evaluated by direct observation for 6 h after the initial treatment and scored based on a modified Racine scale with only motor seizures being considered (Class I and II seizures were not scored). See Racine R. J., 1972, *Electroencephalogr. Clin. Neurophysiol.* 32:269-279. Briefly, motor seizure severity was characterized as follows: class III, animals displayed forelimb clonus with a lordotic posture; class IV, animals reared with concomitant forelimb clonus; and class V animals had a Class IV seizure and fell over. Only rats having, at least, class III convulsive seizure were included in the study.

Histochemical Analyses.

The brain of the rats paraffin sections (10 μm) were cut coronally and stained with Fluoro-Jade B (Histo-Chem Inc., Jefferson, Ark.) follows the method described in the literature. See e.g., Hopkins, K J, et al., 2000, *Brain Res* 864:69-80; Liang L P, et al., 2008, *J Neurosci* 28:11550-11556. The Fluoro-Jade B positive signal in a given area was estimated with Image J (National Institutes of Health, Bethesda, Md.).

HPLC Assay.

Ascorbate, cysteine, cystine, glutathione (GSH), glutathione disulfide (GSSG), tyrosine, 3-nitrotyrosine (3-NT) were performed with ESA (Chelmsford, Mass.) 5600 CoulArray® HPLC equipped with eight electrochemical detector cells as previously described in the literature. See e.g., Beal M F, et al., 1990, *J Neurochem* 55:1327-1339; Liang L P, et al., 2007, *J Neurosci* 27:4326-4333.

Statistical Analyses.

Survival analysis was performed using the Kaplan-Meier method. For all biochemical analyses, two-way ANOVA was used. P values less than 0.05 were considered significant.

Results

The structure of AEOL 10150 follows. The antioxidant effect of AEOL10150 compared with Cu—Zn SOD (superoxide dismutase) is provided in Table 1. A unit of SOD activity is defined as the amount of compound that inhibits one-half the reduction of epinephrine by superoxide at pH 10.2. CAT: catalase activity measured by Clarke electrode. 4HNE assay by HPLC.

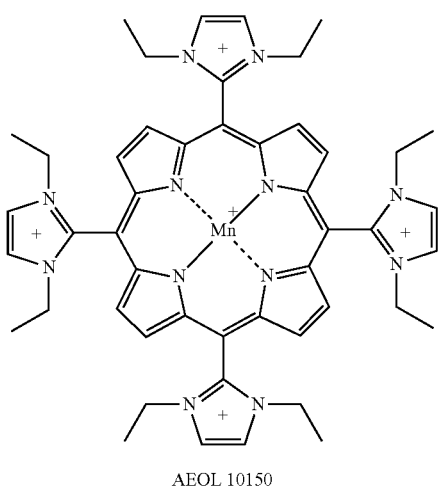

AEOL 10150

TABLE 1

Antioxidant effects of AEOL10150.

| Compounds | SOD Activity (U/mg) | CAT (1/min) | 4HNE IC$_{50}$ (nM) |
|---|---|---|---|
| Cu—Zn SOD | 15267 | — | — |
| AEOL10150 | 43103 | 2.2 | 271 |

Figure 1B:
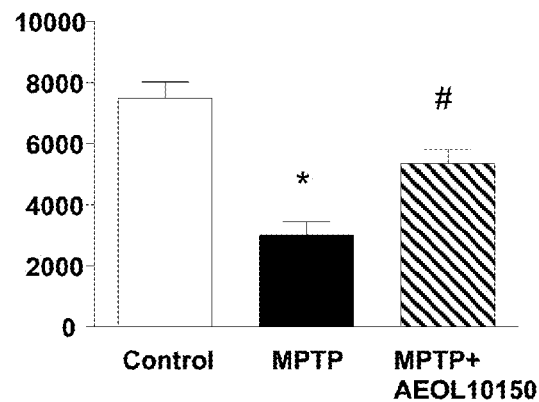
Figure 1C:
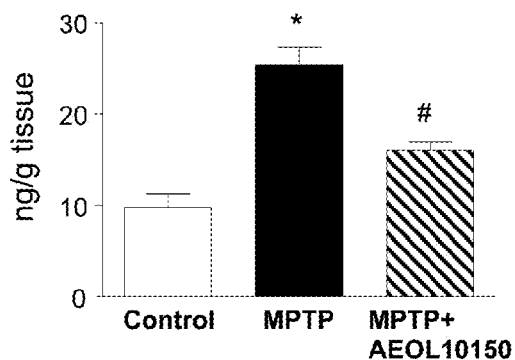

FIGS. 1A-1C demonstrate that AEOL10150 penetrates the BBB (blood brain barrier) following systemic administration in mice and protects against MPTP (1-methyl-4-phenyl-1,2,3,6-tetrahydropyridine) neurotoxicity, as known in the art.

Figure 2A:
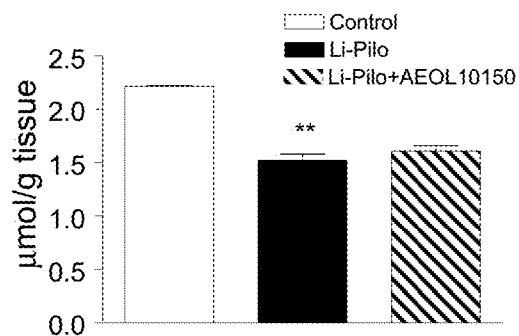
FIGS. 2A-2C. Histograms depict concentration of GSH (FIG. 2A) and GSSG (FIG. 2B), and GSH/GSSG (FIG. 2C) ratio in the hippocampus of the rat after either pilocarpine alone or in the presence of AEOL10150 post-treatment. Bars represent mean+S.E.M, **p<0.01 vs. control rats, #p<0.05 vs. pilocarpine alone treated rats; one-way ANOVA, n=3 rats per group. Legend: Control (open); pilocarpine (closed); pilocarpine+AEOL10150 (diagonal lines).
Figure 2B:
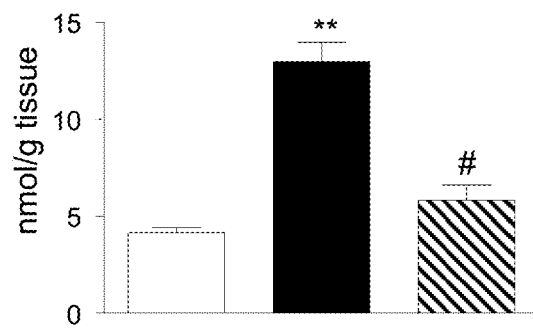
Figure 2C:
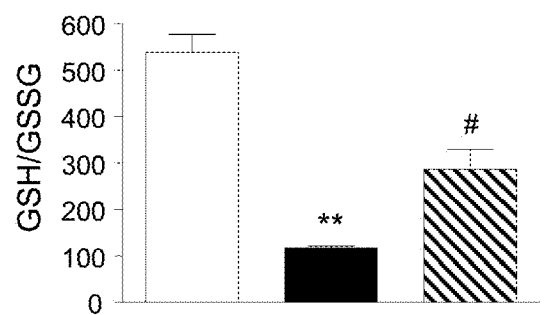

FIGS. 2A-2C demonstrate that AEOL10150 attenuates pilocarpine-induced GSH/GSSG changes.

Figure 3A:
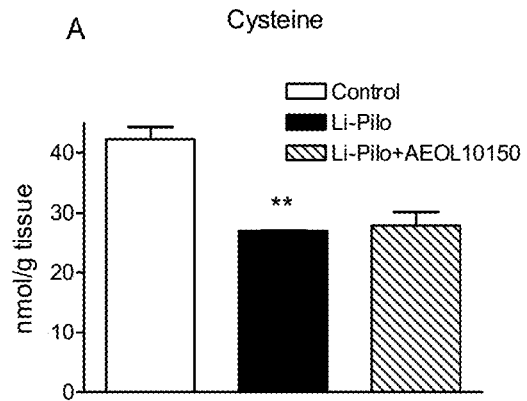
FIGS. 3A-3C. Histograms depict concentrations of Cysteine (FIG. 3A) and Cystine (FIG. 3B), and Cysteine/Cystine ratio (FIG. 3C) in the hippocampus of the rat after either pilocarpine alone or in the presence of AEOL10150 post-treatment. Bars represent mean+S.E.M, **p<0.01 vs. control rats, #p<0.05 vs. pilocarpine alone treated rats; one-way ANOVA, n=3 rats per group. Legend: Control (open); pilocarpine (closed); pilocarpine+AEOL10150 (diagonal lines).
Figure 3B:
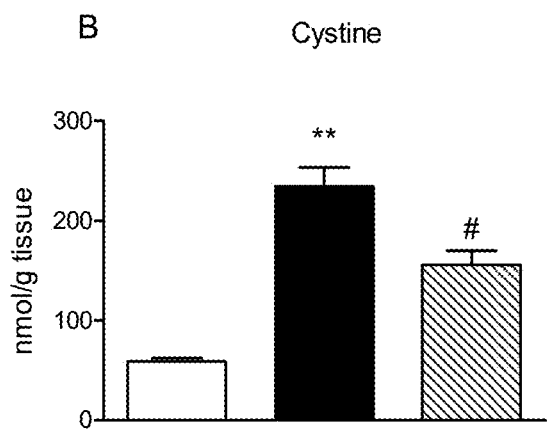
Figure 3C:
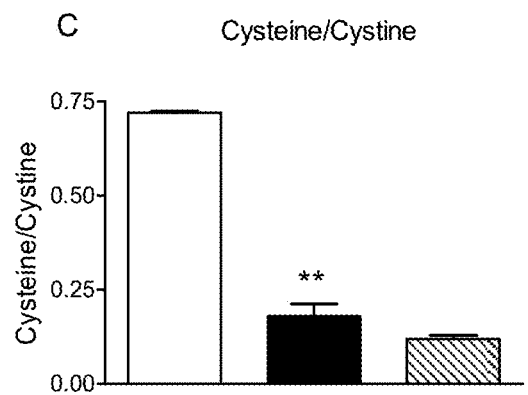

FIG. 3A-3C demonstrate that AEOL10150 attenuates pilocarpine-induced Cysteine/Cystine changes.

Figure 4A:
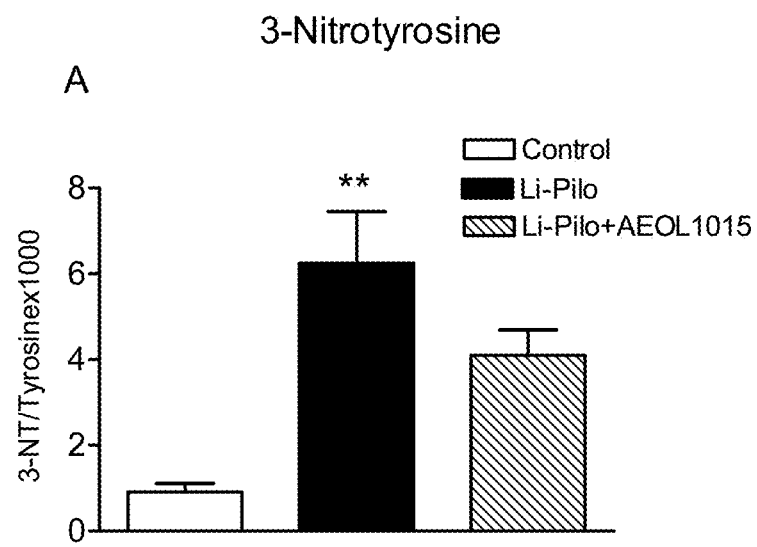
FIGS. 4A-4B. Histograms depict 3-NT/tyrosine ratio (FIG. 4A) and AA (FIG. 4B) in the hippocampus of the rat after either pilocarpine alone or in the presence of AEOL10150 post-treatment. Bars represent mean+S.E.M, **p<0.01 vs. control rats, #p<0.05 vs. pilocarpine alone treated rats; one-way ANOVA, n=3 rats per group. Legend: Control (open); pilocarpine (closed); pilocarpine+AEOL10150 (diagonal lines).
Figure 4B:
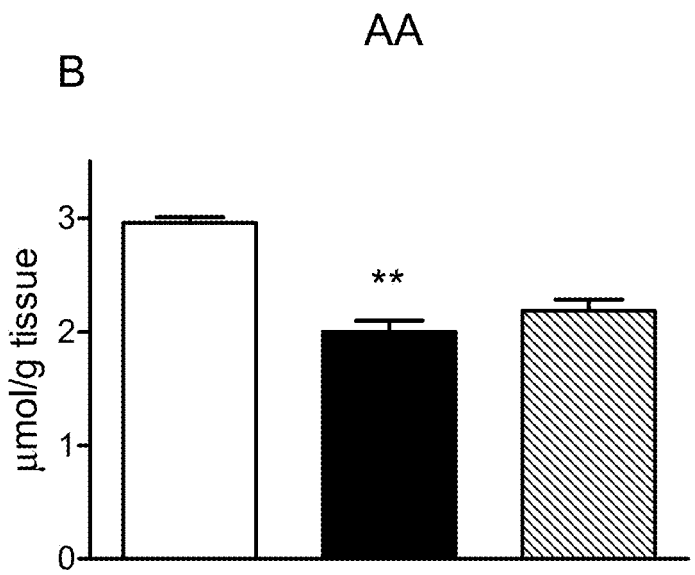

FIGS. 4A-4B demonstrate that AEOL10150 attenuates pilocarpine-induced increase in 3-Nitrotyrosine/Tyrosine ratio.

Figure 5A:
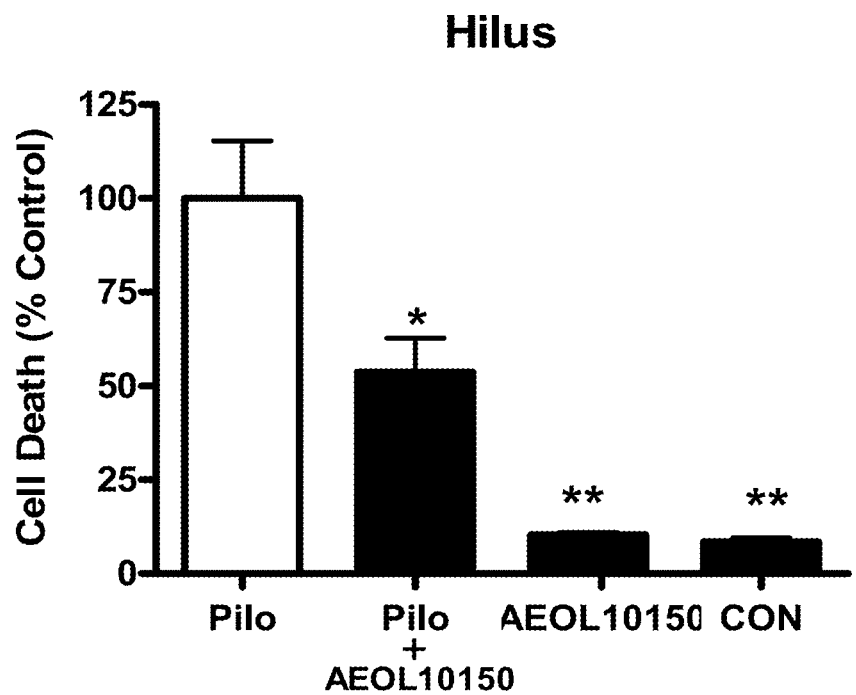
FIGS. 5A-5B. Histograms depict quantitative analysis of Fluoro-jade B fluorescence in the hilus (FIG. 5A) and CA3 (FIG. 5B) of the rat after either pilocarpine alone or in the presence of AEOL10150 post-treatment. Bars represent mean+S.E.M, *p<0.05, **p<0.01 vs. pilocarpine alone treated rats; one-way ANOVA, n=3 rats per group. Histogram ordering (left to right): pilocarpine; pilocarpine+AEOL10150; AEOL10150; control.
Figure 5B:
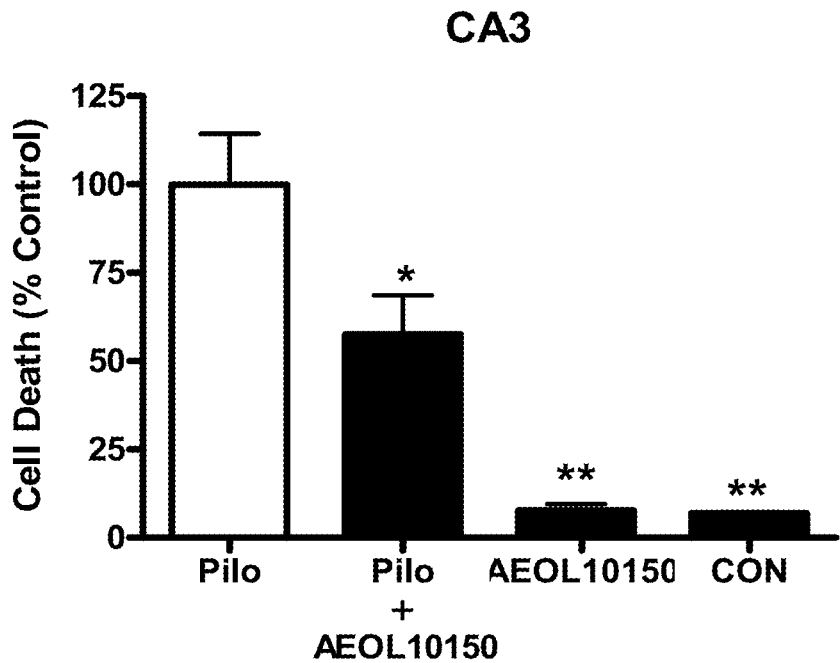
Figures 6A, 6B, 6C, 6D, 6E, 6F:
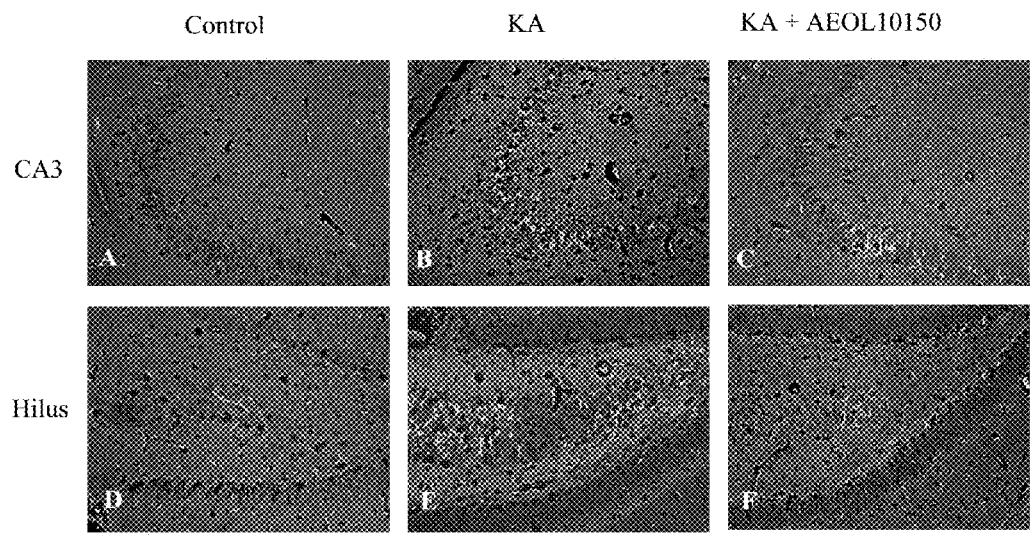
FIGS. 6A-6F. Photomicrographs depict representative Fluoro-jade B stained images in the CA3 (FIGS. 6A-6C) and hilus (FIGS. 6D-6F) of rats after either kainate alone or in the presence of AEOL 10150 post-treatment.
Figure 7A:
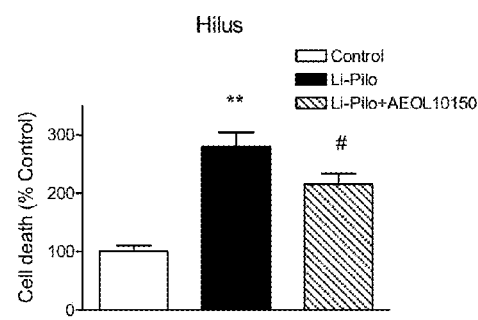
FIGS. 7A-7B. Histograms depicts quantitative analysis of Fluoro-jade B fluorescence in the hilus (FIG. 7A) and CA3 (FIG. 7B) of the rat after either kainate alone or in the presence of AEOL 10150 post-treatment. Bars represent mean+S.E.M, **p<0.01 vs. control rats, #p<0.05 vs. kainate alone treated rats; one-way ANOVA, n=4 rats per group. Legend: Control (open); pilocarpine (closed); pilocarpine+AEOL10150 (diagonal lines).
Figure 7B:
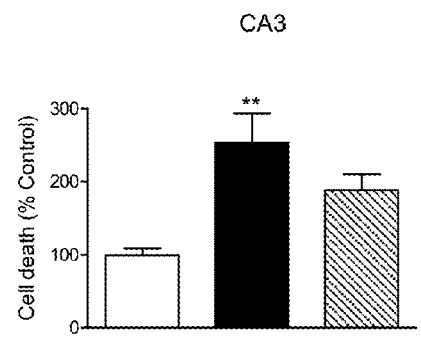

FIGS. 5A-5B demonstrate that AEOL10150 attenuates pilocarpine-induced hippocampal cell death.

FIGS. 6A-6F and FIGS. 7A-7B demonstrate that AEOL10150 attenuates Kainate-induced hippocampal cell death.

Figure 8A:
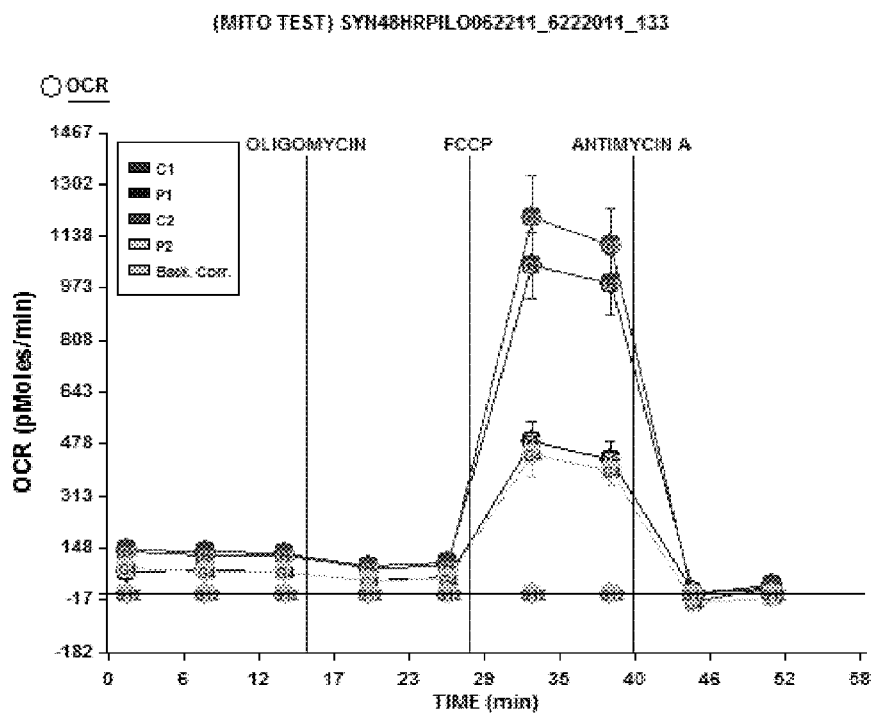
FIGS. 8A-8B depict representative oxygen consumption rates (OCR) in isolated hippocampal synaptosomes 48 h after injection pilocarpine (FIG. 8A) or kainate (FIG. 8B) in rats.
Figure 8B:
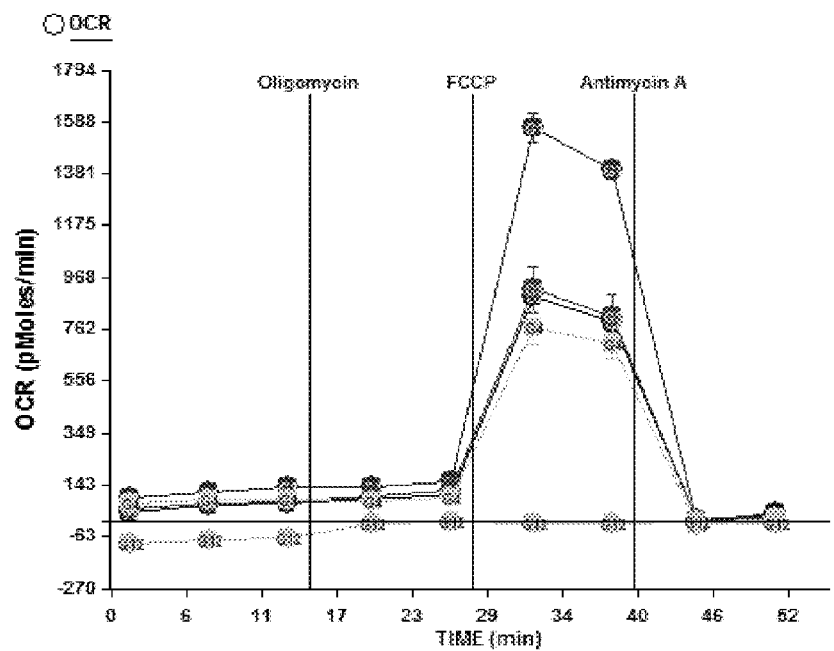
Figure 9A:
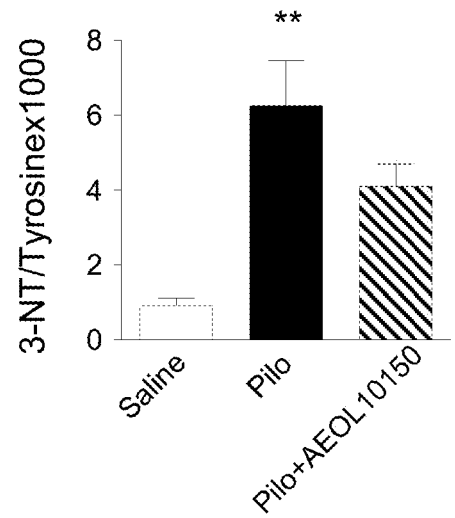
FIGS. 9A-9B. Histograms depict AEOL10150 effect on 3-NT/Tyrosine (FIG. 9A) and GSH/GSSG (FIG. 9B) 24 hours following Pilocarpine (pilo)-induced SE. AEOL 10150 was injected at a dose of 5 mg/kg every 4 hours s.c. beginning 90 min after SE onset. **p<0.01, *p<0.05, ***p<0.001 n=3 per group. Legend: Control (saline) (open); pilocarpine (closed); pilocarpine+AEOL10150 (diagonal lines).
Figure 9B:
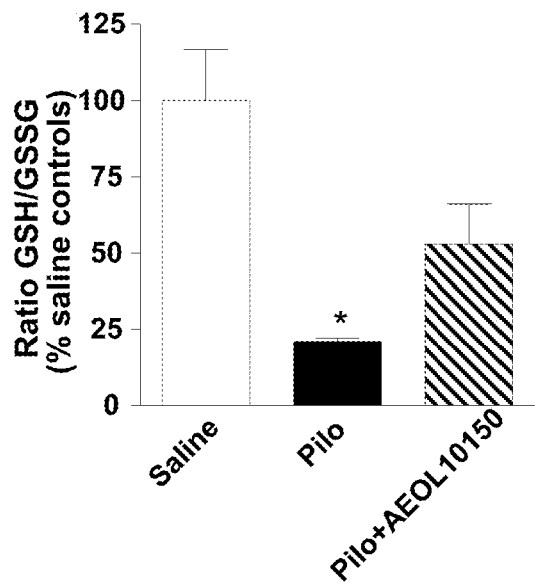

FIGS. 8A-8B demonstrate that oxygen consumption rates (OCR) in isolated hippocampal synaptosomes are decreased after injection of pilocarpine or kainate.

SUMMARY

FIGS. 1A-8B demonstrate that AEOL10150 penetrates the BBB following systemic administration in mice; AEOL10150 inhibits oxidative stress indices 90 minutes post-pilocarpine or kainate treatment; AEOL10150 inhibits hippocampal cell loss 90 minutes post-pilocarpine or kainate treatment; and pilocarpine- or kainate-induced seizures result in decreased oxygen consumption rates.

Example 2

Neuroprotective Efficacy of AEOL10150 Against Neurotoxic Agents

Introduction.

Chemical warfare agents (e.g., chemical threat agents) are an immense threat to military personnel and civilians. The central nervous system (CNS) is a sensitive target for chemical toxicants that interact with receptors and signaling e.g. nerve agents or organophosphate pesticides. See e.g., Jett, D. A. & D. T. Yeung, Proc Am Thorac Soc. 7(4): 254-6. Studies in the literature have established that controlling seizure activity and downstream consequences is critical for neuroprotection and survival after nerve agent. See e.g., Shih, T. M., et al., 2003, Toxicol Appl Pharmacol 188(2):69-80. Accordingly, the goal of this research project is to develop a novel and efficacious neuroprotective countermeasure against nerve agents. Recent efforts by the NIH CounterAct program to develop medical countermeasures have identified AEOL10150 as a lead compound with broad efficacy against multiple chemical threats. AEOL10150 is a catalytic antioxidant with a wide spectrum of activity against superoxide radicals ($O_2^-$.), hydrogen peroxide ($H_2O_2$), peroxynitrite ($ONOO^-$), and lipid peroxyl radicals. See e.g., Day, B. J., 2004, Drug Discovery Today 9(13):557-66. Work by the PI and colleagues over the past decade demonstrates the efficacy of metalloporphyrins in numerous cell and animal models of neuronal injury. See e.g., Patel, M., 2003, Aging Cell 2(4): 219-222; Patel, M., 1998, Neurochem 71:1068-1074; Patel, M. & B. J. Day, 1999, Trends Pharmacol Sci 20:359-364; Patel, M., et al., 1996, Neuron 16:345-355; Sheng, H., et al., 2002, Free Radical Biology & Medicine 33(7):947-61; Li, Q. Y., et al., 2001, J Neurochem 78(4):746-55; Liang, L. P., et al., 2000, Neuroscience 101(3):563-70. The PI's laboratory has also established that oxidative stress is a critical consequence of prolonged seizures and contributes to seizure-induced neuronal death. See e.g., Liang, L. P., Y, 2000, Id.; Liang, L. P., et al., 2008, J Neurosci 28(45):11550-6; Waldbaum, S., et al., 2010, Journal of Neurochemistry 115(5):1172-1182. Since elicitation of seizure activity is an important mechanism of several chemical threat agents e.g. nerve agents and organophosphate pesticides, it is important to determine whether AEOL10150 exerts neuroprotection against such agents.

Several important attributes of AEOL10150 support its rapid development as a lead medical countermeasure agent. 1) It has completed Phase 1 human clinical trials for safety with a low incidence of adverse events which can expedite its development. 2) It is efficacious against several threats including radiation, chlorine and mustard gas. See e.g., O'Neill, H. C., et al., 2010, Free Radic Biol Med 48(9):1188-96; Gould, N. S., et al., 2009, J Pharmacol Exp Ther 328(3): 732-9. 3) It has favorable pharmacokinetic properties following subcutaneous injection which is ideal for its use as a medical countermeasure. 4) It is efficacious in experimental models when administered post-exposure i.e. after the chemical threat agent which allows its self-administration after chemical exposure.

Thus, the goal of this project is to determine if AEOL10150 is a neuroprotective medical countermeasure against nerve agents using pilocarpine as a surrogate agent. Nerve agents such as sarin and VX are known to rapidly elicit seizures in animals and exposed individuals as evidenced by the Tokyo subway attack and use in the Iran-Iraq war. See e.g., Jett, D. A. & D. T. Yeung, Proc Am Thorac Soc. 7(4):254-6; Jett, D. A., Sci Transl Med. 2(23):23ps12. We have shown that pilocarpine-induced seizures result in profound oxidative stress.

See e.g., Waldbaum, S., et al., 2010, Id. Therefore, catalytic removal of reactive oxygen species (ROS) by AEOL10150 is predicted to blunt oxidative stress and prevent downstream changes such as metabolic dysfunction, gliosis and neuronal loss.

Compelling in vivo preliminary data demonstrate that 1) pilocarpine produces oxidative stress and mitochondrial dysfunction, 2) AEOL10150 is permeable to the rodent brain, and 3) inhibits pilocarpine-induced oxidative stress and neuronal death. The specific goals of each specific aims below include establishing the dose, mechanism and therapeutic window of neuroprotection. The following parameters can be measured: 1) blood brain barrier (BBB) permeability and pharmacokinetic parameters for optimization of dosing, 2) oxidative stress indices (reduced and oxidized glutathione, 3-nitrotyrosine levels, 8-hydroxy-2'-deoxyguanosine (8-OHdG), 4-hydroxynonenal (4-HNE) levels), 3) mitochondrial oxygen consumption rates and glycolytic metabolism 4) seizure activity using 24/7 video EEG monitoring and 5) neuronal loss (Fluoro-Jade B analysis) and 5) gliosis (astrocyte and microglial markers).

Specific Aims.

A first specific aim is to determine BBB permeability of AEOL10150 in rats. This includes a) determine of plasma and brain concentrations, and b) establishment of optimal dose and dosing regimen. A second specific aim is to evaluate the neuroprotective efficacy of AEOL10150 against pilocarpine exposure in rats. This includes a) determining efficacy and therapeutic window of AEOL10150 on pilocarpine-induced seizures, oxidative stress, mitochondrial dysfunction, neuronal loss and gliosis, and b) determining the neuroprotective efficacy of AEOL10150 following administration with standard therapy (diazepam and atropine).

Background and Significance

Seizures are a Critical Consequence of Nerve Agent.

Exposure to nerve agents, metabolic poisons, or high levels of sulfur mustard can trigger seizures and loss of consciousness. The elicitation of seizures is a common manifestation of nerve agents that target the CNS. See e.g., Jett, D. A. & D. T. Yeung, Id.; Jett, D. A., Id. Therefore it is important for medical countermeasures to intervene at two levels. The first level of intervention is usually to ameliorate the symptoms arising due to the specific interaction of the agent and cellular targets. Nerve agents and organophosphate pesticides bind and inhibit acetylcholinesterase (AChE) leading to a persistent increase cholinergic tone. This produces acute effects of nerve agent poisoning including muscle paralysis, cardiorespiratory depression, massive secretion from mucous membranes, eye irritation, and blurry or dim vision which can be controlled by atropine and other cholinergic antagonists. A second level of intervention is targeting the delayed injury response to the threat agents. Seizure activity is the most critical injury response common to nerve agents and organophosphate exposures. See e.g., Shih, T. M., et al., 2003, *Toxicol Appl Pharmacol* 188(2):69-80; Shih, T., et al., 1999, *J Biomed Sci* 6(2):86-96.

Oxidative Stress is a Consequence of Chemical Convulsants:

An important by-product of mitochondrial metabolism, xenobiotic detoxification and other enzymatic chain reactions is the production of ROS. Excessive production of ROS can overwhelm antioxidant defenses resulting in oxidation of vulnerable cellular targets. Work from this laboratory has demonstrated that seizures resulting from chemical convulsants such as pilocarpine and kainic acid oxidatively damage mitochondrial DNA, susceptible mitochondrial proteins and cellular lipids. See e.g., Patel, M., 2004, *Free Radic Biol Med* 37(12):1951-62. In addition to being an acute consequence of SE, mitochondrial ROS production re-emerges immediately prior to development of chronic epilepsy assessed by behavioral analysis, suggesting that ROS formation could contribute to epileptogenesis. See, e.g., Jarrett, S. G., et al., 2008, *Neurobiol Dis.* 30:130-138.

AEOL10150, a Catalytic Antioxidant is a Medical Countermeasure with Broad Efficacy Against Multiple Agents:

Catalytic antioxidants, which are small, molecular mimics of superoxide dismutase (SOD) and/or catalase, potent inhibitors of lipid peroxides and ONOO$^-$ hold particular promise. See e.g., Day, B. J., 2004, *Drug Discov Today* 9(13): 557-66. Because they are catalytic, and not merely free radical scavengers, these compounds are much more potent antioxidants than dietary additives such as vitamin E that act stoichiometrically. The manganese meso-porphyrin catalytic antioxidants (e.g., AEOL10150, Table 2) combine the broad spectrum of reactivity like the stoichiometric antioxidants with the catalytic efficiency of the endogenous antioxidant enzymes. Table 2 discloses the effect of AEOL 10150 to destroy superoxide (as measured by pulse radiolysis), hydrogen peroxide (Clark oxygen electrode [Day, B. J., 2004, *Drug Discovery Today* 9(13): 57-66]), peroxynitrite (stop-flow) and inhibit lipid peroxidation (F2-isoprostanes [Kachadourian, R., et al., 2004, *Biochemical Pharmacology*, 67(1): 77-85]).

TABLE 2

Structure and antioxidant activities of AEOL10150

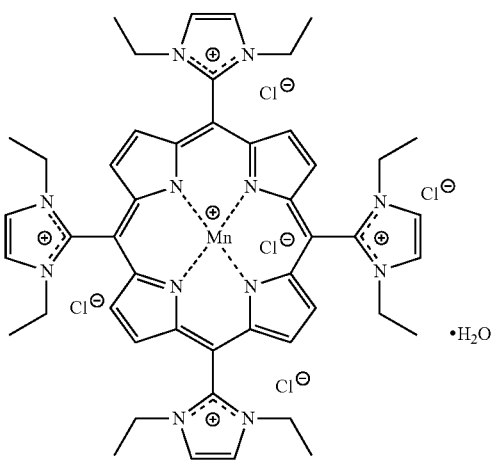

| Reactive Oxygen Species | Superoxide | Hydrogen peroxide | Lipid Peroxides | Peroxynitrite |
|---|---|---|---|---|
| Activity | $k_{cat}(O_2^{\bullet -}) =$ 6.78 × $10^7 M^{-1} s^{-1}$ | $k(H_2O_2) =$ 2.2 min$^{-1}$ | $F_2$-IP IC$_{50}$ = 0.1 μM | $k(ONOO^-) =$ 1.01 × $10^7 M^{-1} s^{-1}$ |

These synthetic compounds can be chemically modified to increase their ability to cross the BBB and various subcellular compartments. Metalloporphyrins have plasma half lives that range from 4 to 48 hours. Patel et al. first demonstrated the neuroprotective effects of MnTBAP, a prototypical first generation metalloporphyrin. See e.g., Patel, M., et al., 1996, Id. Since then their properties have been optimized resulting in the development of AEOL10113, AEOL10150 and the orally bioavailable, AEOL11207. The efficacy of these compounds have been demonstrated in multiple models of neuronal injury. See e.g., Trova, M. P., et al., 2003, *Bioorganic &*

*Medicinal Chemistry* 11(13):695-707. For e.g. AEOL11207, a lipophilic metalloporphyrin, protected against 1-methyl 4-phenyl tetrahydropyridine (MPTP) neurotoxicity in vivo following oral administration. See e.g., Liang, L. P., et al., 2007, Id. Most metalloporphyrins are not extensively metabolized by the body and are largely excreted unchanged in the urine. AEOL10150 is a prototypical water soluble metalloporphyrin that possesses extremely high SOD activity. On a weight basis, its SOD activity surpasses that of CuZnSOD. It also catalyzes the dismutation of $H_2O_2$ and inhibits lipid peroxidation with potent IC50s and scavenges $ONOO^-$ efficiently. See e.g., Day, B. J., *Drug Discovery Today*, 2004. 9(13): 557-66; Day, B. J., et al., 1999, Id.; Day, B. J. & J. D. Crapo, 1996, *Toxicology and Applied Pharmacology* 140(1):4-100; Day, B. J., et al., 1997, *Archives of Biochemistry and Biophysics* 347(2):256-262.

Study 1: AEOL10150 Penetrates the BBB Following Systemic Administration in Mice and Protects Against MPTP Neurotoxicity.

MPTP is a prototypical neurotoxicant that is widely used to induce parkinsonism in mice. MPTP neurotoxicity is thought to arise primarily via inhibition of the mitochondrial electron transport chain at the level of complex I and consequent metabolic inhibition and ROS production. FIGS. 1A-1C (Example 1) show the ability of AEOL 10150 to penetrate the mouse BBB and inhibit MPTP-induced dopaminergic neuronal loss and oxidative stress.

Results and Interpretation:

As shown in FIG. 1A, AEOL10150 achieved concentrations of 150-200 pmoles/g in the mouse brain following single injection. Estimated AEOL10150 concentrations based on its molecular weight is 100-200 nM. Based on AEOL10150's potent antioxidant activity profile, these concentrations are expected to exert neuroprotection.

Study 2. AEOL10150 Inhibits Oxidative Stress Indices 90 Minutes Post-Pilocarpine Treatment.

Previous work in our laboratory demonstrates marked oxidative stress and mitochondrial dysfunction in the hippocampus of rats injected with pilocarpine. See e.g., Waldbaum, S., et al., 2008, *Soc Neurosci Abstr*, 511.6. Here we conducted a study to determine the effects of AEOL10150 on pilocarpine-induced oxidative stress. As shown in FIGS. 3A-3B, injection of AEOL10150 90 minutes after pilocarpine resulted in a statistically significant inhibition of oxidative stress indices (3-nitrotyrosine/tyrosine; 3-NT/tyr and GSH/GSSG ratios) in the hippocampus 24 hours later.

Study 3. AEOL10150 Inhibits Hippocampal Cell Loss 90 Minutes Post-Pilocarpine Treatment.

A study was conducted to determine the effect of AEOL10150 on pilocarpine-induced hippocampal cell loss.

Methods and Results:

Rats were injected AEOL10150 90 min s.c. after receiving saline (CON) or pilocarpine (Pilo) and sacrificed 24 h thereafter. Frozen sections (15 μm) were cut coronally and stained with Fluoro-Jade B (Histo-Chem Inc., Jefferson, Ark.) with modifications of a method described in the literature. See e.g., Hopkins, K. J et al., 2000, *Brain Res.*, 864(1): 69-80. Images were captured using a Nikon Optiphot-2 80i microscope equipped with epifluorescence optics (Nikon Inc., Melville, N.Y.). The Fluoro-Jade B positive signal of a given area was measured with Image J software. The average of relative fluorescence density was expressed as percentage of the control. As shown in FIGS. 5A-5B, this study demonstrates the ability of AEOL10150 to significantly decrease hippocampal cell loss in the hilar and CA3 regions.

Study 4. Pilocarpine Decreases Oxygen Consumption Rates in the Hippocampus.

Figure 10:
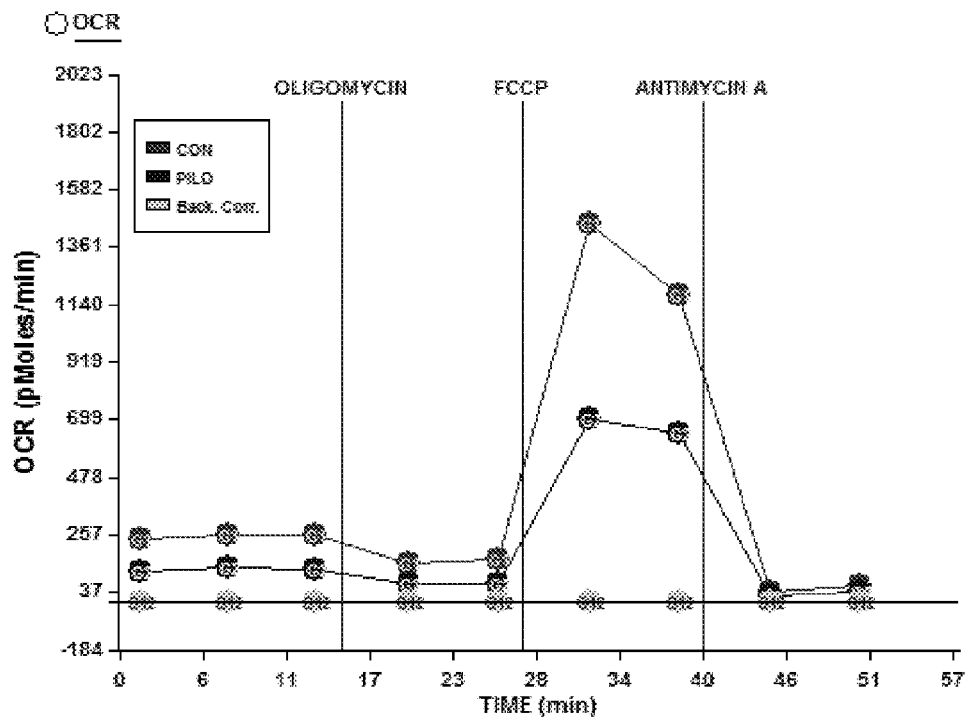
FIG. 10 depicts oxygen consumption rates (OCR) in isolated hippocampal synaptosomes 16 h after injection of saline and pilocarpine. Points represent average values from 2 rats per group.

A key end point of Specific Aim 2 is to assess metabolic flux (oxygen consumption rates; OCR) in real time using the Seahorse Biosciences extracellular flux analyzer. To support the feasibility of these studies, we provide pilot data clearly demonstrating decreased OCR in hippocampal synaptosomes from pilocarpine- vs. saline-treated rats 16 hours after injection (average values from n=2 rats per groups, FIG. 10). This study suggests that pilocarpine seizures result in decreased stimulated OCR in hippocampal synaptosomes and underscores the feasibility of testing the effects on AEOL10150 on pilocarpine-induced changes in OCR in vivo.

Summary.

The data of Studies 1-4 demonstrate the ability of AEOL10150 to penetrate the mouse brain at therapeutic concentrations and to protect against pilocarpine-induced oxidative stress and neuronal loss. Moreover, pilocarpine decreases OCR, a key index of mitochondrial function.

Research Strategy: Specific Aim 1: To Determine BBB Permeability of AEOL10150 in Rats.

Rationale:

The pharmacokinetic profile of AEOL10150 can be determined to guide studies that its efficacy. Measurements of plasma and brain concentrations of the compound in rats is necessary for determining an optimal dosing regimen and correlate its biological effects with in vivo efficacy in the pilocarpine rat model. In addition, data using AEOL10150 in the mouse indicate that it crosses the mouse BBB.

Experimental Approach:

Groups of 6-10 rats can be administered 2.5, 5 or 10 mg/kg of AEOL10150 by the s.c. route (single or multiple i.e. every 4, 8 and 24 h) and sacrificed at various times (1, 3, 6, 12, 24 and 48 hr) following the last injection. Once blood samples are obtained, rats can be perfused free of blood and the brains (hippocampus, piriform cortex and frontal cortex) can be collected for analysis. Compounds can be measured using methods known in the art. See e.g., Kachadourian, R., et al., 2004, Id.; Kachadourian, R., et al., 2003, *Journal of Inorganic Biochemistry*, 95(4): 240-8.

AEOL10150 Measurement:

AEOL10150 can be measured in plasma and brain samples by HPLC-UV methods as previously described for AEOL11207. See e.g., Liang, L. P., et al., 2007, *J Neurosci* 27(16): 4326-33

Analysis:

Pharmacokinetic Analysis of Drug Levels can be Analyzed by PKAnalyst® (MicroMath® software). The following parameters can be obtained: 1) Elimination $T_{1/2}$ in plasma and brain; 2) Distribution T1/2 in plasma and brain regions; 3) Volume of distribution of AEOL10150 (Vd); 4) Time to peak plasma concentrations; 5) Time to peak tissue concentration; 6) AUC (area under the plasma level-time curve), which gives a measure of the extent of drug bioavailability; and 7) Peak plasma and brain levels of AEOL101050.

Research Strategy: Specific Aim 2: To Evaluate the Neuroprotective Efficacy of AEOL10150 Against Pilocarpine Exposure in Rats.

Rationale:

The goal of this project is to determine if AEOL10150 is a neuroprotective medical countermeasure against chemical threat agents that mediate oxidative stress via elicitation of seizures. Work by the PI has demonstrated that various chemical convulsants including pilocarpine produce profound oxidative stress in vulnerable brain areas. See e.g., Liang, L. P., et al., 2000, *Neuroscience* 101(3):563-570;

Waldbaum, S., et al., 2010, *Journal of Neurochemistry* 115 (5):1172-1182; Liang, L. P. & M. Patel, 2006, *Free Radic Biol Med* 40(2):316-22. Therefore, catalytic removal of ROS by AEOL10150 is predicted to blunt oxidative stress and prevent downstream changes such as metabolic dysfunction, gliosis and neuronal loss thereby aiding recovery of the brain from the chemical attack. Video-EEG analysis, oxidative stress indices, mitochondrial functions, glycolytic rates and neuronal death/gliosis markers and their time points of assessment are all based on pilot studies and prior work in the laboratory.

Aim 2a:

The rationale for testing AEOL10150 alone is to determine its therapeutic window and whether it is sufficient to exert neuroprotection in a pre-treatment and post-treatment paradigm. In Specific Aim 2a, we can determine a neuroprotective dose of AEOL10150 and its therapeutic window (by treatment 30 min before, 60 min, 90 min, 3 h and 6 h after pilocarpine) in the presence or absence of scopolamine, an anticholinergic agent which does not penetrate the BBB. Video EEG analysis can determine if AEOL10150 has any effect on pilocarpine-induced seizure activity. Using an optimal dose, two separate time points (30 min before and selected time after pilocarpine) can determine AEOL10150's influence on seizure activity over a 24 h period.

Aim 2b:

It is important to determine the neuroprotective efficacy of AEOL10150 in the absence and presence of standard therapy for nerve agent exposure i.e. anticholinergic agents and benzodiazepines. Although pralidoximine (2-PAM) and/or diazepam are first line therapies for nerve agent poisoning, it is important to determine whether a new therapy can work on its own and in combination with standard therapies. Aim 2b determines the neuroprotective ability of AEOL10150 in combination with standard treatments (anticholinergic agent and diazepam). The rationale for using atropine vs. 2-PAM or carbamates is model-dependent i.e. because pilocarpine is a muscarinic agonist and therefore 2-PAM, which works via cholinesterase is believed to be ineffective. Treatment with atropine (0.5-2 mg/kg, i.m.) 5 min post-pilocarpine and diazepam (10-20 mg/kg, i.p.) 30 min after first motor seizure is based on our experience, literature findings and standard use of these countermeasures discussed in the *NIH Strategic Plan for Medical Countermeasures*. See e.g., Shih, T. M., et al., 3004, *Toxicol Appl Pharmacol* 188(2):69-80; Shih, T., et al., 1999, *J Biomed Sci* 6(2):86-96; Shih, T. M., et al., 2011, *Toxicol Mech Methods* 21(1):53-62. Further studies and Aims 1 and 2a can determine optimal doses, order and timing of each agent. The ability of the combination to influence pilocarpine-induced seizures, oxidative stress and injury can be assessed using video-EEG analysis, oxidative stress indices, mitochondrial functions and neuronal death/gliosis markers.

Experimental Approach

Experimental Timing.

Figure 11:
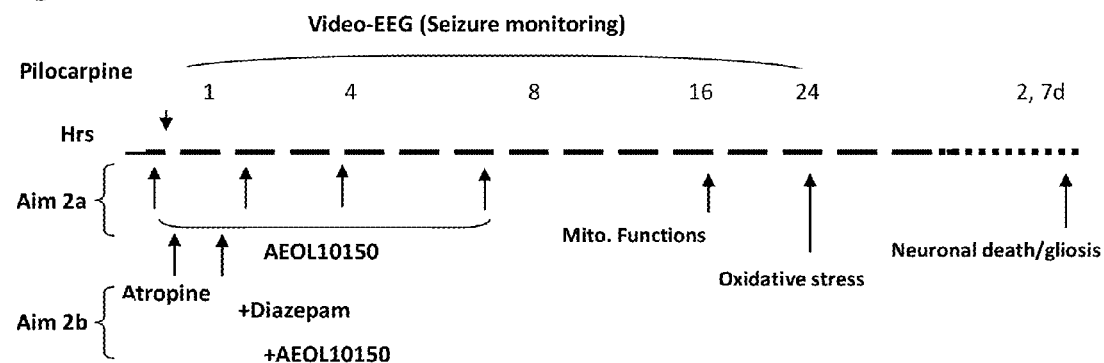
FIG. 11 depicts a time line for studies described in Example 2.

A schematic diagram of a time line for experimental conditions for studies for Aims 2a and 2b is disclosed in FIG. 11.

Aim 2a.

The goal of this study is to answer the following questions. 1) What is the optimal dose and dosing regimen for AEOL10150? Pharmacokinetic analysis (Specific Aim 1) and measurement of oxidative stress indices and cell death allow us to determine the dose and dosing frequency of AEOL10150 to optimally inhibit pilocarpine-induced oxidative stress and cell death. 2) What is the therapeutic window of AEOL10150 neuroprotection? Once a dose and dosing frequency are established, we can determine the window of opportunity after pilocarpine treatment that yields statistically significant neuroprotection (see end points below). This can be addressed by varying the timing of AEOL10150 treatment before or after pilocarpine (30 min before, 60 min, 90 min, 3 h and 6 h after pilocarpine). To determine whether peripheral cholinergic systems need to be blocked to achieve optimal CNS neuroprotection with AEOL10150, we plan to include a group of animals injected with scopolamine (30 min prior to pilocarpine). Finally, 3) does AEOL10150 have any effect on seizure activity? Using an optimal dose of AEOL10150, its ability to influence seizure activity can be assessed by continuous video-EEG over a 24 h period. AEOL10150 can be administered 30 min prior to pilocarpine to determine if pre-treatment has an effect and at one selected time point after pilocarpine to determine any influence on ongoing seizure activity.

Aim 2b.

To determine the neuroprotective efficacy of AEOL10150 in the absence and presence of standard therapy for nerve agent exposure, the following treatment groups can be conducted: 1) control, 2) pilocarpine, 3) pilocarpine+atropine, 4) pilocarpine+diazepam 5) pilocarpine+atropine+AEOL10150+diazepam. Drug alone control groups (for determining effects on endpoints): 1) diazepam, 2) AEOL10150 and 3) atropine. Optimal dose and timing of atropine (0.5-2 mg/kg, dose range i.m., 5 min post-pilocarpine) and diazepam (10-20 mg/kg dose range i.p. and 30 min post first motor seizure) can be determined from studies. AEOL 10150 can be given via s.c. route (dose and timing to be determined from Specific Aim 2a). End points can be the same as discussed in Specific Aim 2a.

End Points.

End points for neuroprotection include mitochondrial functions (basal respiration, ATP turnover, proton leak, and maximal respiratory capacity) and glycolytic rates which can be measured using an extracellular flux analyzer (Seahorse Biosciences) 16 hr after pilocarpine hippocampal synaptosomes. We have optimized these assays in synaptosomes from pilocarpine and kainite injected rats. Mitochondrial aconitase activity can be measured because of its known sensitivity to ROS and its mitochondrial localization and fumarase activity because it serves as a control enzyme that is insensitive to oxidative damage. See e.g., Patel, M., 1996, *Molecular Psychiatry* 1:362-363. ATP levels (as well as ADP and AMP) can be measured to monitor bioenergetic status (16 hr).

Additional end points for neuroprotection include oxidative stress indices (24 hr): Several indices of oxidative stress can be measured including GSH and GSSG which assess the cellular redox status, 4-HNE, which is an electrophilic lipid peroxidation end product, 8OHdG/2dG, which is an index of oxidative DNA damage and 3-NT, which is an indicator of protein nitration. The choice of oxidative stress indices (GSH/GSSG, 4-NHE and 8-OHdg/2dG) has been aligned with the standard markers used to assess the protective effects of AEOL10150 in other studies. Additionally, we have included two additional markers, 3-NT/tyr and aconitase/fumarase to obtain information regarding nitrosative stress (3-NT) and mitochondrial oxidative stress (aconitase inactivation).

Additional end points for neuroprotection include cell death and gliosis: A principal end point of this study is evaluation of neuronal viability and glial response to injury. Neuronal viability can be assessed by Fluoro Jade B analysis which detects injured neurons by stereological methods. Gliosis can be assessed by analysis of GFAP, a marker of astrocytes and Iba1, a marker of activated microglia at the 2 and 7d time points.

Tissue and Brain Regions:

AEOL10150 levels can be measured in plasma and hippocampus, piriform cortex and frontal cortex. Oxidative stress end points can be measured in hippocampus, piriform cortex and cerebellum (control region). Neuronal viability and gliosis can be assessed in the hippocampus, piriform cortex, frontal cortex and cerebellum (control region). Mitochondrial and glycolytic function assays can be measured in synaptosomes from hippocampus and piriform cortex.

Methods:

Male Sprague-Dawley rats (200-250 g) can be treated with 340 mg/kg pilocarpine hydrochloride i.p. alone or after pretreatment with methyl-scopolamine (1 mg/kg) i.p. (Aim 2a) or 5 min prior to atropine (0.5-2 mg/kg, i.m.) followed by AEOL10150 at varying time points following pilocarpine and then diazepam (10-20 mg/kg, i.p.) 30 min after the first motor seizure (Aim 2b). All rats can be directly observed and those having a minimum of 5 P3 seizures based on a modified Racine scale [Racine, R. J., 1972, *Electroencephalogr Clin Neurophysiol.* 32:281-94.] can be treated with either saline or AEOL10150 s.c. beginning 30 min prior to or 90 min, 3 h or 6 h post-pilocarpine and every 4, 8, 24 hours thereafter until sacrifice (Aim 2a). Measurements of GSH, GSSG, 8OHDdG/2dG, 3NT and tyrosine can be performed with a HPLC equipped electrochemical and UV detectors by previous methods. See e.g., Liang, L. P., et al., 2007, Id.; Day, B. J., et al., 1999, *Free Radical Biology and Medicine* 26(5-6):730-6; Hensley, K., et al., 1998, *J Neurosci* 18(20):8126-32. 4-HNE can be measured by HPLC-EC methods and GC mass spectrometry for verification. Mitochondrial functions can be analyzed in isolated synaptosomes (subregions in Aim 2) 16 h after pilocarpine using the XF analyzer. The effect on cellular respiration rates [OCR] can be measured after vehicle, 1.2 M oligomycin (inhibitor of ATP synthase), 4 M FCCP (to short-circuit proton circuit and get maximal respiration), 1 µM myxothiazol and 2 M rotenone (to inhibit electron transfer). AMP, ADP and ATP can be quantified by HPLC-UV at 258 nm. See, e.g., Sellevold, O. F., et al., 1986, *J Mol Cell Cardiol* 18(5):517-27; Botker, H. E., et al., 1994, *J Mol Cell Cardiol,* 26(1):41-8.

Statistical Analysis:

Two-way ANOVA can be used to determine the differences between treatment and drug. Group measures can be expressed as mean+SEM. The statistical significance of differences can be assessed with the Neuman-Keul post hoc test. The level of significance can be set at p<0.05.

Example 3

Further Investigation of BBB Penetration of AEOL10150

Because the tetrakis diethylimidazolium porphyrin AEOL10150 has a net charge of at least +5 under physiological conditions of pH, this compound would not be expected a priori to transit the blood brain barrier (BBB) solely due to passive diffusion, e.g., absent an active transport system in the cells forming the BBB including endothelial, basement membrane and/or astrocytic cells. Moreover, we find no evidence for an active transport system for AEOL10150. Thus, it has been surprisingly discovered that AEOL10150 indeed transits the BBB.

Figure 12:
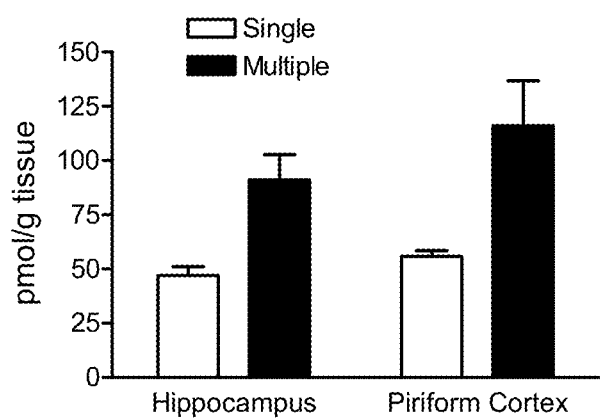
FIG. 12 depicts histograms of the concentration AEOL10150 (pmol/g tissue) in the hippocampus and piriform cortex after s.c. injection of AEOL10150 in the rat. Legend: (open): single injection of AEOL10150 (5 mg/kg, s.c.) at 4-hrs; (closed): multiple injections of AEOL10150 (5 mg/kg, s.c., every 4-hrs, 6 injections total) at 24-hrs. Error bars: SEM (standard error of the mean). Groups: n=4. Histogram ordering (left to right): hippocampus single dose; hippocampus multiple dose; piriform cortex single dose; piriform cortex multiple dose. Legend: Single dose of AEOL10150 (open); multiple dose (closed).

In order to determine the extent and distribution of AEOL10150 upon administration via modes which do not include intracerebral implantation, intracerebroventricular or convection enhanced diffusion, as known in the art, rats were administered either a single injection (5 mg/kg, s.c.), or multiple injections (5 mg/kg, s.c., every 4-hr for 24-hrs) of AEOL10150. As depicted in FIG. 12, the concentration (pmol/g tissue) of AEOL10150 was quantified in the hippocampus and piriform cortex. Based on the potent antioxidant activity profile of AEOL10150, the concentrations reported in FIG. 12 are expected to exert neuroprotection when administered every 4-hrs for at least 24-hrs, e.g., 24-48 hrs.

Example 4

Therapeutic Window of Neuroprotective Effects of AEOL10150

Studies were conducted to determine the therapeutic effects including timing (i.e., the so-called "therapeutic window") of AEOL10150 on pilocarpine-induced oxidative stress and neuronal injury. Rats received pilocarpine (340 mg/kg, i.p.) alone or in combination with AEOL10150 (5 mg/kg, s.c.).

Figure 13A:
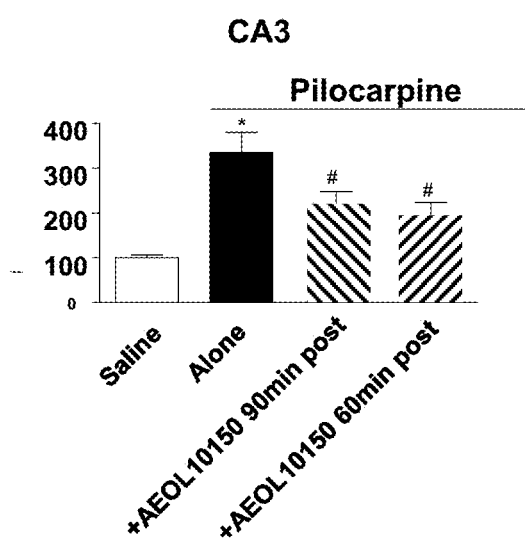
FIGS. 13A-13B depict histograms of quantitative analysis of Fluoro-Jade B histofluorescence staining in the CA3 (FIG. 13A) and Hilus (FIG. 13B) of the rats at 24 h after receiving either pilocarpine (340 mg/kg, i.p.) alone or in presence of AEOL10150 (5 mg/kg, s.c., start at 60 or 90 min post pilocarpine treatment and every 4 h therefore until sacrificed). The Fluoro-Jade B positive signal in a given area of hippocampal subregions from three slides of each animal was estimated with Image J. Bars represent mean+S.E.M, $*p<0.01$ vs. saline; $\#p<0.05$ vs. pilocarpine; one way ANOVA, n=6 rats per group. Legend: Control (saline) (open); pilocarpine alone (closed); pilocarpine+AEOL10150 90 min post pilocarpine administration (diagonal lines upper left to lower right); pilocarpine+AEOL10150 60 min post pilocarpine administration (diagonal lines lower left to upper right).
Figure 13B:
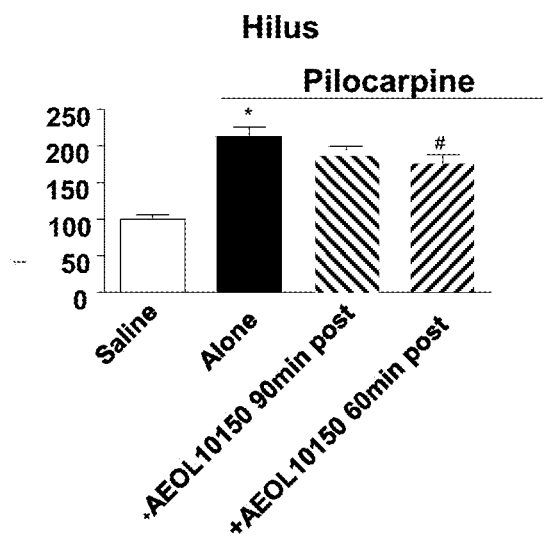

As depicted in the histograms of FIGS. 13A-13B, quantitative analysis of Fluoro-Jade B histofluorescence staining in the CA3 (FIG. 13A) and Hilus (FIG. 13B) of the rats at 24 h after receiving either pilocarpine alone or in the presence of AEOL10150 at 60 or 90 min post pilocarpine treatment and every 4 h therefore until sacrifice. The Fluoro-Jade B positive signals in a given area of hippocampal subregions from three slides of each animal were estimated with Image J (available at the rsb.info.nih.gov website). For FIGS. 13A-13B, bars represent mean+S.E.M, *p<0.01 vs. saline; #p<0.05 vs. pilocarpine; one way ANOVA, n=6 rats per group.

Figure 14A:
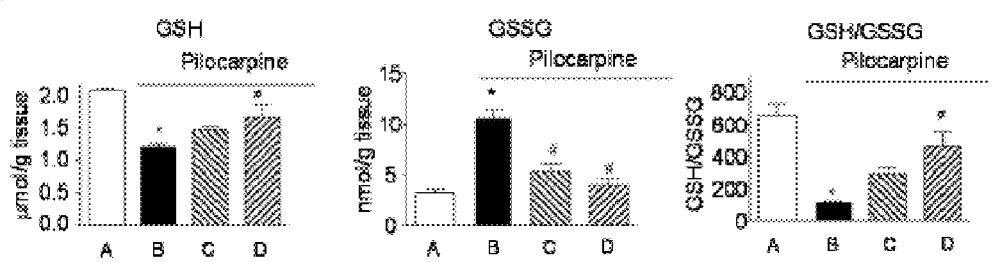
FIGS. 14A-14C.
Figure 14B:
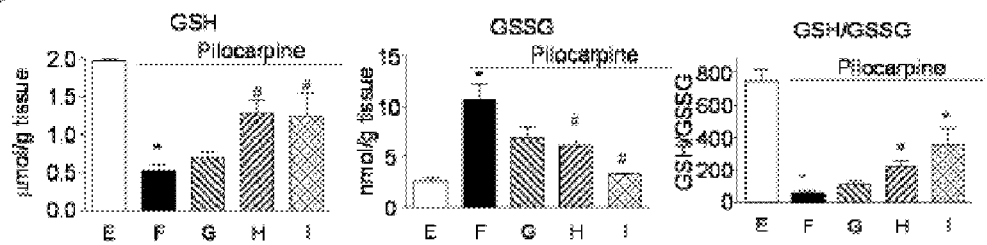

As depicted in FIGS. 14A-14B, injection of AEOL10150 at 60 or 90 minutes after pilocarpine administration resulted in inhibition of oxidative stress indices (i.e., GSH, GSSG, and GSH/GSSG ratios, left, center and right panels, respectively) in the hippocampus.

As depicted in FIG. 14B, 30 min pretreatment of AEOL10150 resulted in maximum protection of oxidative stress indices followed by 60 min which afforded better protection than 90 min post-pilocarpine treatment.

Figure 14C:
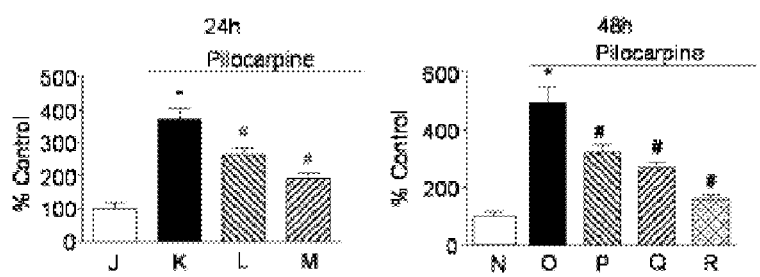

As depicted in FIG. 14C, 3-nitrotyrosine/tyrosine ratio in the hippocampus of the rat at 24-hrs (left panel) and 48-hrs (right panel) after either pilocarpine alone, or additionally with AEOL10150 administration at 90 min after, 60 min after, or 30-min before (right panel only) and continued every 4-hrs until sacrifice.

Example 5

Effects of AEOL10150 on Pilocarpine-Induced Mitochondrial Respiratory Defects

Figure 15A:
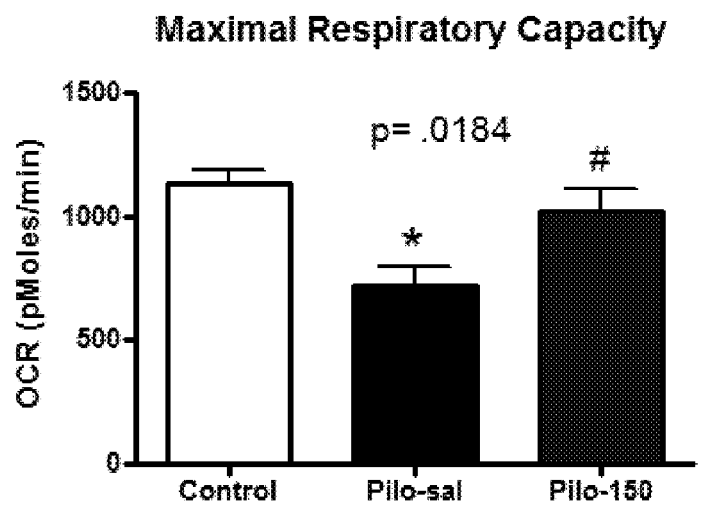
FIGS. 15A-15B.
Figure 15B:
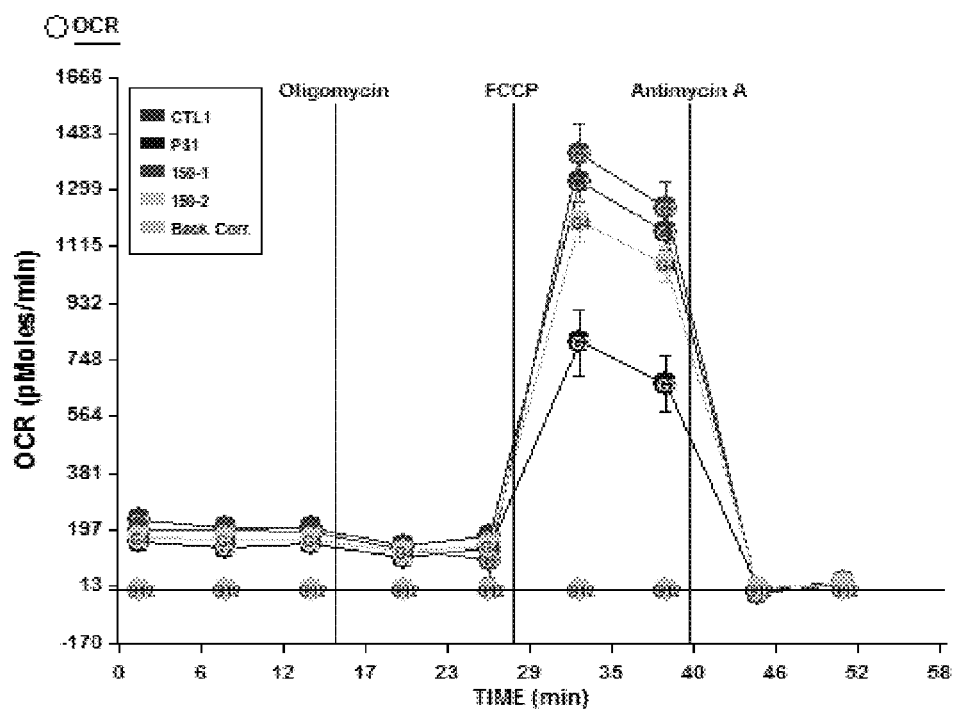

In order to test the hypothesis that mitochondrial ROS production mediates metabolic dysfunction which occurs following pilocarpine exposure, we determined oxygen consumption rates (OCR) in synaptosomes isolated from saline, pilocarpine alone and pilocarpine+AEOL10150 (latter injected 60 min after and every 4 h (q4 h) thereafter for 24 h). Methods for determining OCR as well known in the art. As depicted in FIG. 15A, maximal respiratory capacity is rescued by administration of AEOL10150 and pilocarpine. Indeed, maximal respiratory rates (FIG. 15B) as well as ATP turnover, baseline respiration and glycolytic rates (data not shown) decreased by pilocarpine were largely prevented by AEOL10150. This provides the first evidence that metabolic dysfunction following pilocarpine is inhibited by a catalytic antioxidant, e.g., AEOL10150.

Example 6

AEOL10150 Inhibits Pilocarpine-Induced Microglial Activation

Figure 16A:
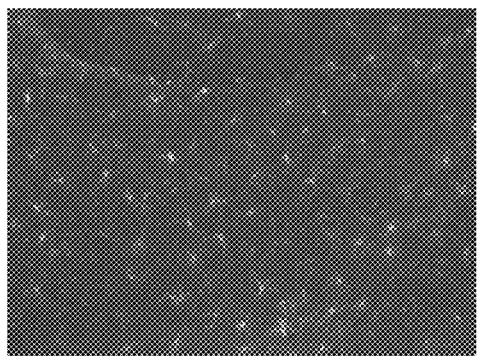
FIGS. 16A-16F.
Figure 16B:
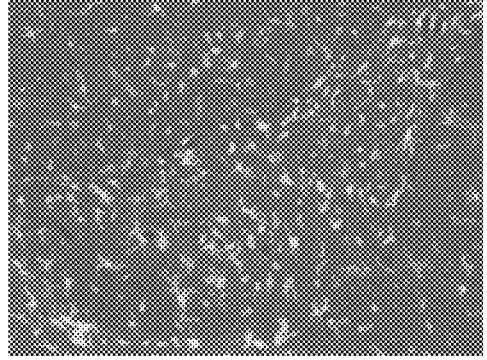
Figure 16C:
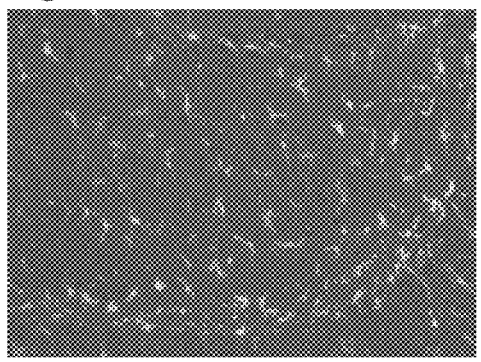
Figure 16D:
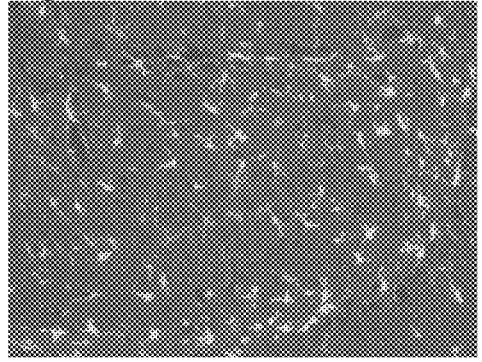
Figure 16E:
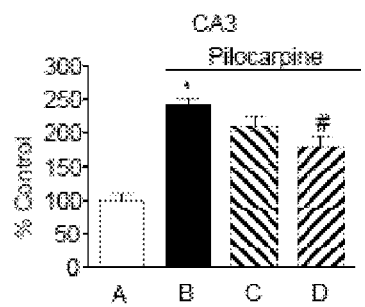
Figure 16F:
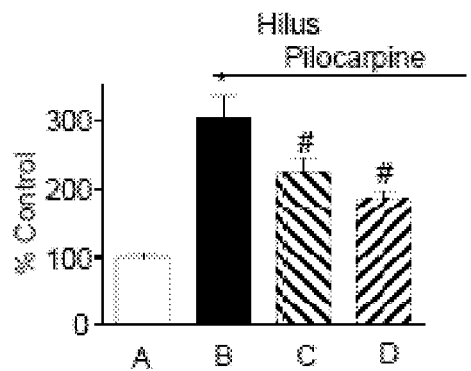
Figure 17A:
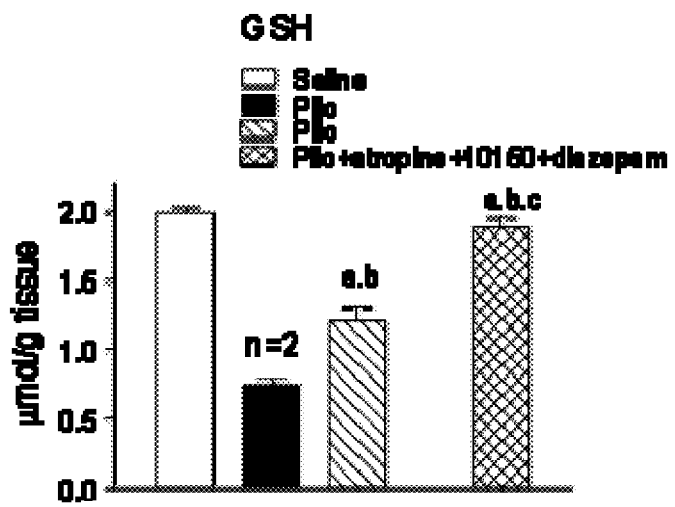
FIGS. 17A-17D are histograms depicting concentrations of GSH (FIG. 17A), GSSG (FIG. 17B), and ratios of GSH/GSSG (FIG. 17C) and 3-nitrotyrosine/tyrosine (FIG. 17D) in the hippocampus of the rat at 24 h after either pilocarpine (340 mg/kg) alone with or without atropine and diazepam or in the presence of AEOL 10150 treatment (5 mg/kg, s.c., every 4 h). Bars represent mean+S.E.M; $^a p<0.01$ vs. control rats; $^b p<0.05$ vs. pilocarpine treated rats; $^c p<0.05$ vs. pilocarpine+atropine+diazepam treated rats. one-way ANOVA, n=2-6 rats per group. saline n=6; pilocarpine, n=2 (3 of 5 dead); pilocarpine+atropine+diazepam, n=6; pilocarpine+atropine+AEOL10150+diazepam, n=6). Histogram ordering (left to right): Control (saline) (open); pilocarpine (closed); pilocarpine+atropine+diazepam (diagonal lines); pilocarpine+atropine+diazepam+AEOL10150 (cross checkered).
Figure 17B:
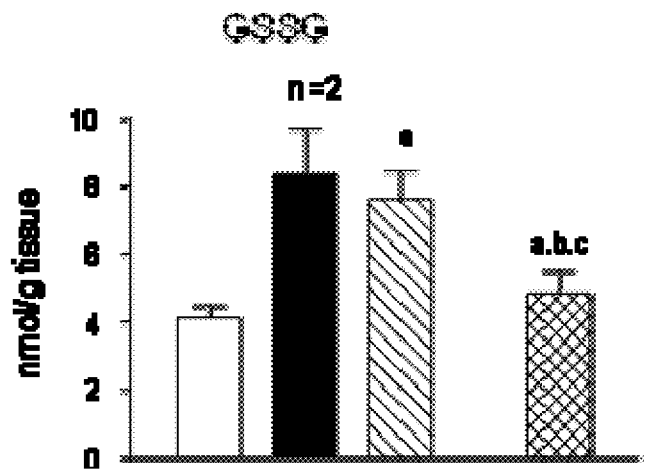
Figure 17C:
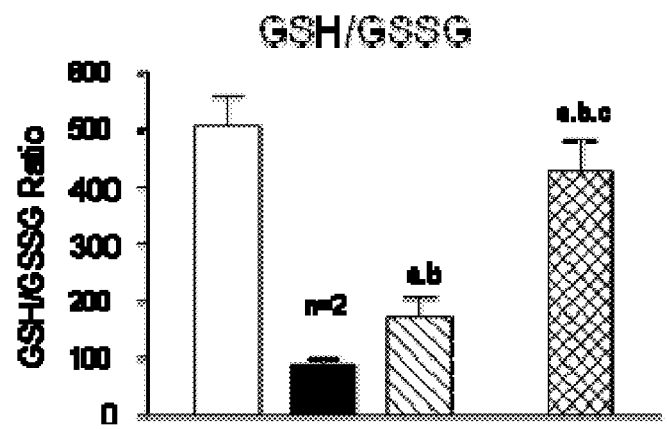
Figure 17D:
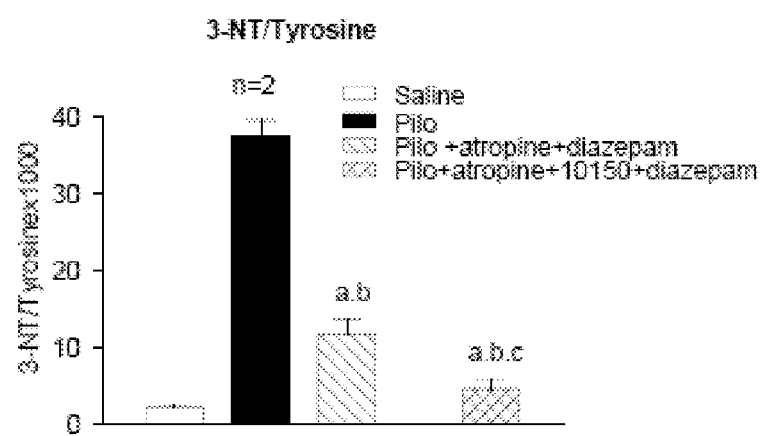

Oxidative stress and neuronal damage can activate inflammation. Accordingly, we investigated whether inflammatory cell activation by pilocarpine-induced seizures was inhibited by AEOL10150. See FIGS. 16A-16D. Hippocampal microglial activation in pilocarpine treated rats analyzed by Iba1 antibody straining histochemical procedures was significantly attenuated by AEOL10150. See FIGS. 16E-16F. This provides evidence that inflammation in this model likely occurs as a result of oxidative damage, and that scavenging ROS can inhibit inflammation.

Example 7

AEOL10150 in Combination Therapy

In order to determine the effect of combination of AEOL10150 in the treatment of subjects administered pilocarpine, a rat model was employed. Male Sprague-Dawley rats (300-350 g) were divided into four different groups: saline, pilocarpine alone, pilocarpine+atropine+diazepam, and pilocarpine+atropine+AEOL10150+diazepam.

Pilocarpine (340 mg/kg, s.c.) or saline was administered to the subjects. Atropine (1 mg/kg, i.m.) or saline was administered at 10 min after pilocarpine. AEOL10150 (5 mg/kg, s.c.) or saline was administered at 60 min after pilocarpine and every 4 hours thereafter until sacrifice. Diazepam (10 mg/kg, i.p.) or saline was administered at 90 min after pilocarpine.

As shown in FIGS. 17A-17D, which are histograms depicting concentrations of GSH (FIG. 17A), GSSG (FIG. 17B), and ratios of GSH/GSSG (FIG. 167) and the ratio 3-nitrotyrosine/tyrosine (FIG. 17D) in the hippocampus of the rat at 24 h after the administration regimen, addition of AEOL10150 in the treatment protocol is observed to enhance the effects of atropine and diazepam as judged by increased GSH concentration and GSH/GSSG ratio, and decreased GSSG and 3-nitrotyrosine/tyrosine ratio.

V. Embodiments

Embodiments contemplated herein include the following.

Embodiment 1

A method for treating a subject suffering from exposure to a chemical threat agent, said method comprising administering to said subject an effective amount of a compound selected from: a) a compound having the structure of Formula (I) or Formula (II),

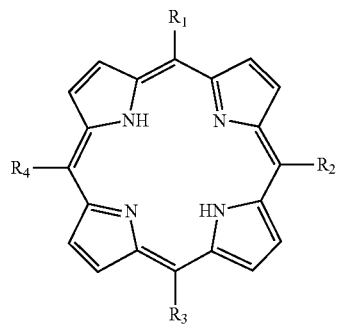

(I)

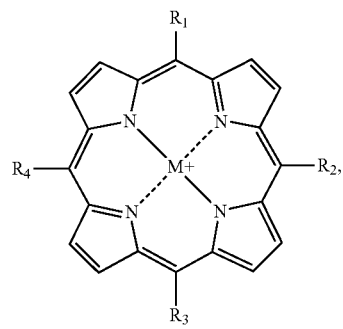

(II)

wherein $R_1$, $R_2$, $R_3$, and $R_4$ are each independently —$CF_3$, —$CO_2R_8$, —$COR_{8'}$,

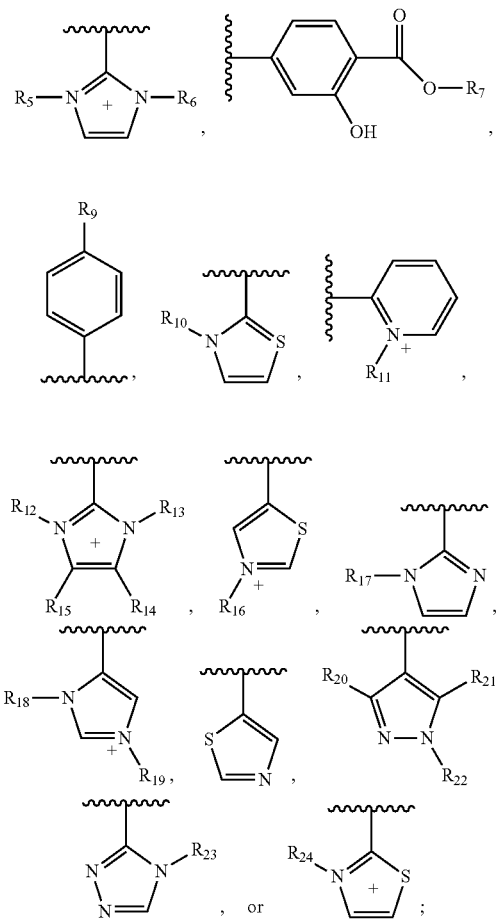

$R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are each independently hydrogen, halogen, —CN, —$CF_3$, —OH, —$NH_2$, —COOH, —$COOR_{25}$, —$CH_2COOR_{25}$, —$CH_2COOH$, an unsubstituted or substituted alkyl, unsubstituted or substituted heteroalkyl, unsubstituted or substituted cycloalkyl, unsubstituted or substituted heterocycloalkyl, unsubstituted or substituted aryl, or an unsubstituted or substituted heteroaryl; $R_{25}$ is an unsubstituted alkyl; and M is a metal; b) a compound having the structure of one of Formulae (X)-(XV),

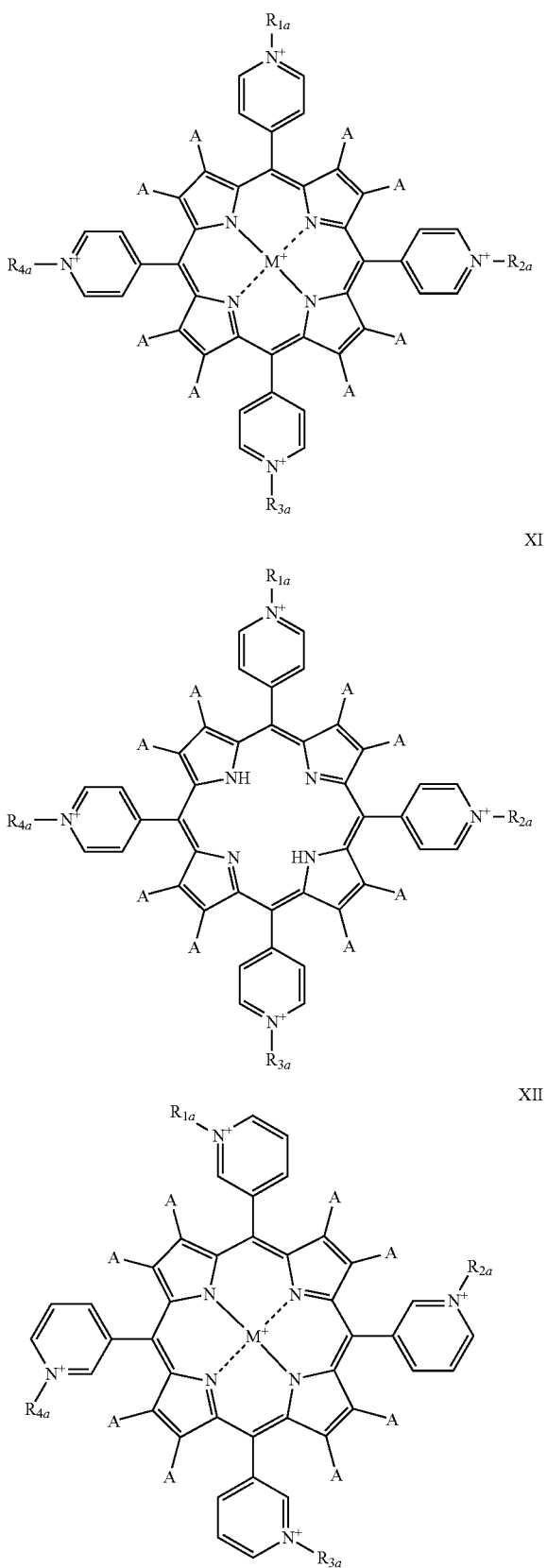
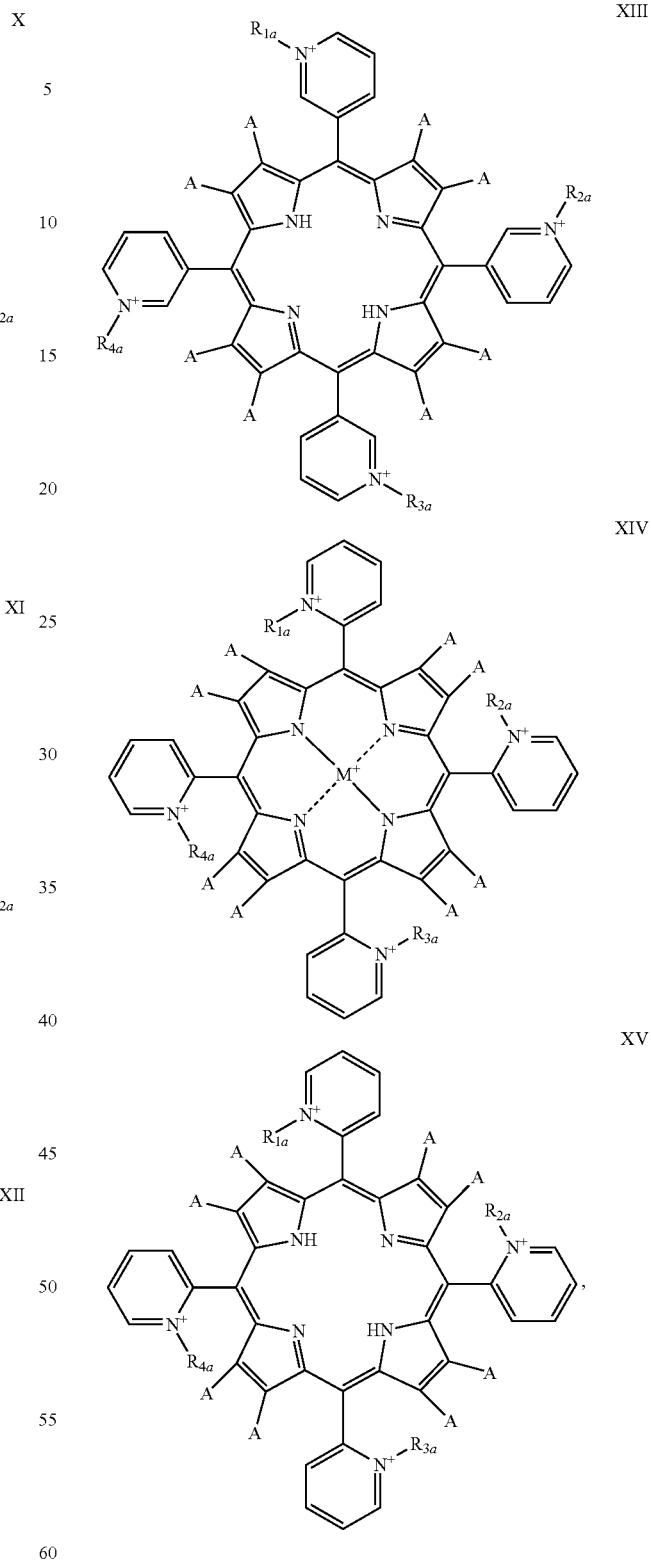
wherein $R_{1a}$, $R_{2a}$, $R_{3a}$, and $R_{4a}$ are independently —$(CH_2)_mCH_2OX_1$ or —$(CH_2CH_2O)_nX_1$; m is 1-6; n is 3-50; $X_1$ is substituted or unsubstituted $C_{1-12}$ alkyl; M is a metal; and each A is, independently, hydrogen or an electron withdrawing group; and c) a compound having the structure of one of Formulae (XVI)-(XVII),

XVI

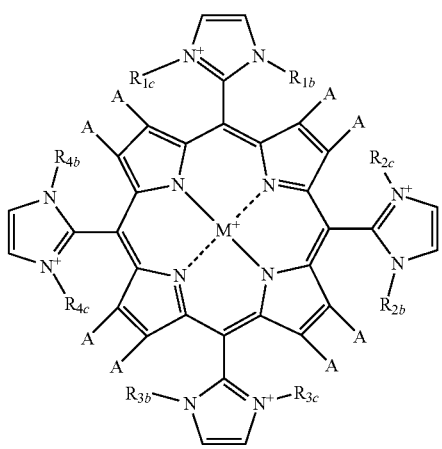

XVII

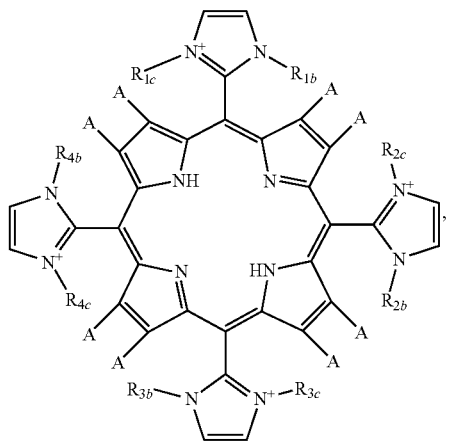

wherein at least one of $R_{1b}$ or $R_{1c}$, $R_{2b}$ or $R_{2c}$, $R_{3b}$ or $R_{3c}$, and $R_{4b}$ or $R_{4c}$ is, independently, $-(CH_2)_pCH_2OX_2$ or $-(CH_2CH_2O)_qX_2$; the other one of $R_{1b}$ or $R_{1c}$, $R_{2b}$ or $R_{2c}$, $R_{3b}$ or $R_{3c}$, and $R_{4b}$ or $R_{4c}$ is, independently, a $C_{1-12}$ alkyl (straight chain or branched); p is 1-6; q is 3-50; $X_2$ is substituted or unsubstituted $C_{1-12}$ alkyl; M is a metal; and each A is, independently, hydrogen or an electron withdrawing group; wherein said chemical threat agent is an anti-cholinesterase agent, a GABA-agent or a metabolic poison.

Embodiment 2

The method according to embodiment 1, wherein said compound has the structure of Formula (I) or Formula (II).

Embodiment 3

The method according to embodiment 2, wherein said compound has the structure of Formula (II).

Embodiment 4

The method according to embodiment 3, wherein said metal is manganese, iron, cobalt, copper, nickel, or zinc.

Embodiment 5

The method according to embodiment 4, wherein said metal is manganese.

Embodiment 6

The according to embodiment 2, wherein $R_1$, $R_2$, $R_3$, and $R_4$ are each

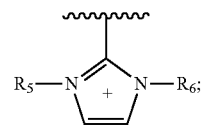

and $R_5$ and $R_6$ are independently unsubstituted alkyl.

Embodiment 7

The method according to embodiment 6, wherein said compound has the structure of Formula (VII)

(VII)

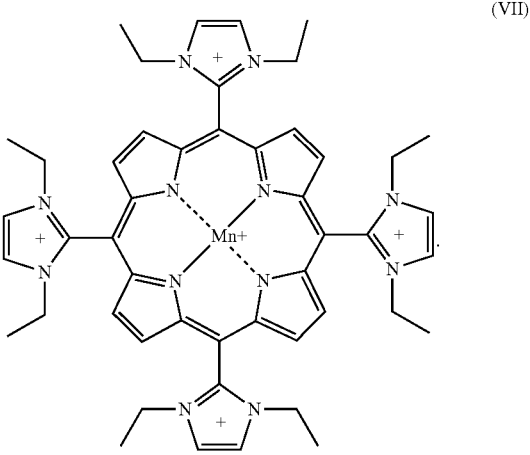

Embodiment 8

The method according to embodiment 1, wherein said compound has the structure of one of Formulae (X)-(XV).

Embodiment 9

The method according to embodiment 8, wherein said metal is manganese, iron, cobalt, copper, nickel, or zinc.

Embodiment 10

The method according to embodiment 9, wherein said metal is manganese.

Embodiment 11

The method according to embodiment 1, wherein said compound has the structure of one of Formulae (XVI)-(XVII).

Embodiment 12

The method according to embodiment 11, wherein said metal is manganese, iron, cobalt, copper, nickel, or zinc.

Embodiment 13

The method according to embodiment 12, wherein said metal is manganese.

Embodiment 14

The method according to any one of embodiments 1 to 13, wherein said chemical threat agent causes seizures and neuropathology.

Embodiment 15

The method according to embodiment 14, wherein said chemical threat agent is a nerve agent.

Embodiment 16

The method according to embodiment 15, wherein said nerve agent disrupts nerve signal by inhibiting acetylcholinesterase.

Embodiment 17

The method according to embodiment 14, wherein said chemical threat agent is sarin, parathion, aldicarb or tetramine (TETS).

Embodiment 18

The method according to any one of embodiments 1 to 13, wherein said chemical threat agent targets the blood.

Embodiment 19

The method according to embodiment 18, wherein said chemical threat agent is cyanide, sodium fluoroacetate, arsenic trioxide or strychnine.

Embodiment 20

The method according to embodiment 1, wherein the effect of said treating a subject suffering from exposure to a chemical threat agent lasts for at least 90 minutes following said administration.

Embodiment 21

A method for reducing brain injury in a subject in need thereof, comprising administering to said subject an effective amount of a compound selected from: a) a compound having the structure of Formula (I) or Formula (II),

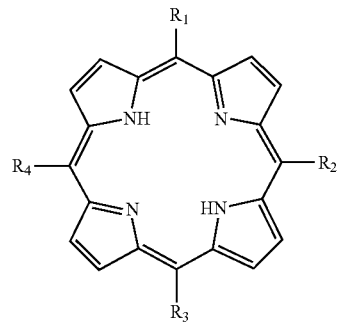

(I)

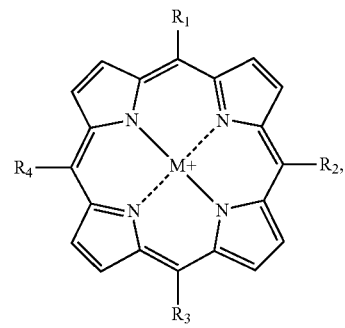

(II)

wherein $R_1$, $R_2$, $R_3$, and $R_4$ are each independently —$CF_3$, —$CO_2R_8$, —$COR_{8'}$,

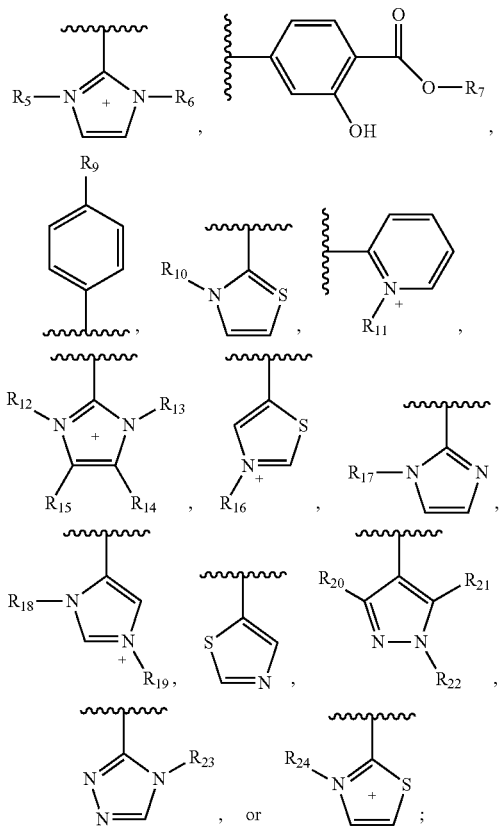

$R_5, R_6, R_7, R_8, R_{8'}, R_9, R_{10}, R_{11}, R_{12}, R_{13}, R_{14}, R_{15}, R_{16}, R_{17}, R_{18}, R_{19}, R_{20}, R_{21}, R_{22}, R_{23}$, and $R_{24}$ are each independently hydrogen, halogen, —CN, —CF$_3$, —OH, —NH$_2$, —COOH, —COOR$_{25}$, —CH$_2$COOR$_{25}$, —CH$_2$COOH, an unsubstituted or substituted alkyl, unsubstituted or substituted heteroalkyl, unsubstituted or substituted cycloalkyl, unsubstituted or substituted heterocycloalkyl, unsubstituted or substituted aryl, or an unsubstituted or substituted heteroaryl; $R_{25}$ is an unsubstituted alkyl; and M is a metal; b) a compound having the structure of one of Formulae (X)-(XV),

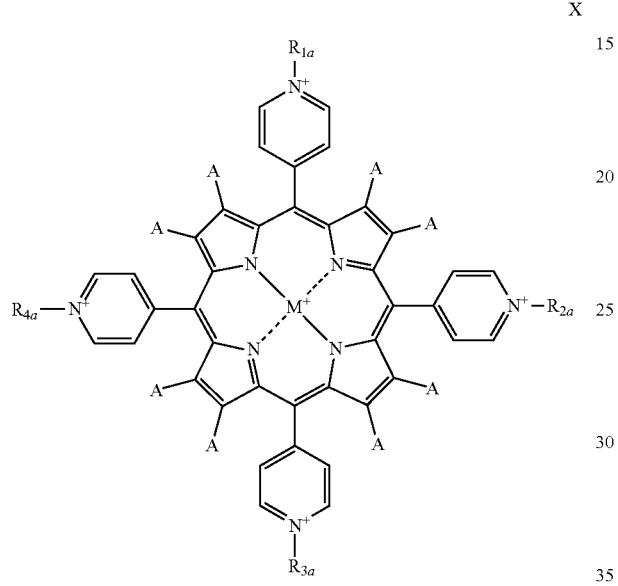

X

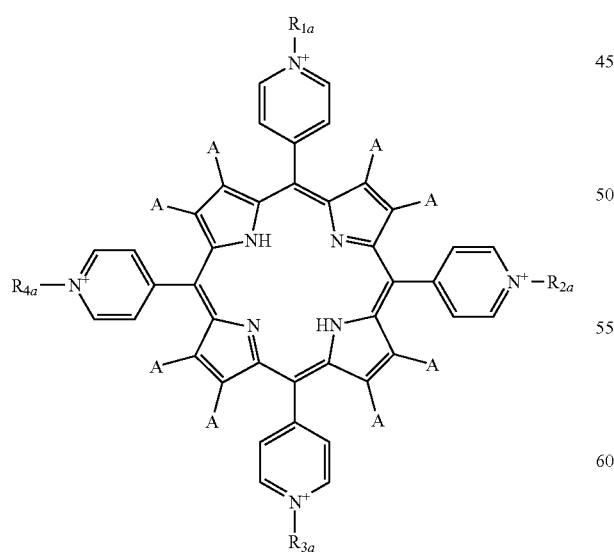

XI

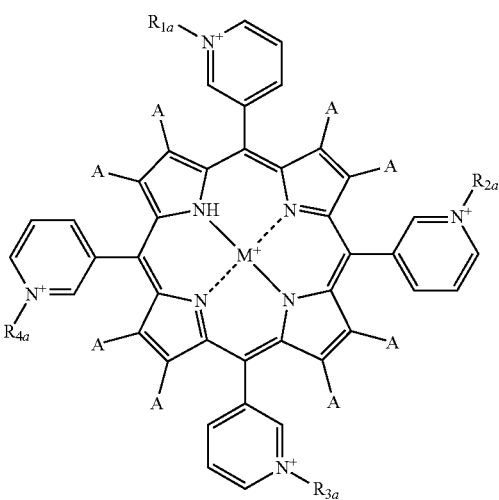

XII

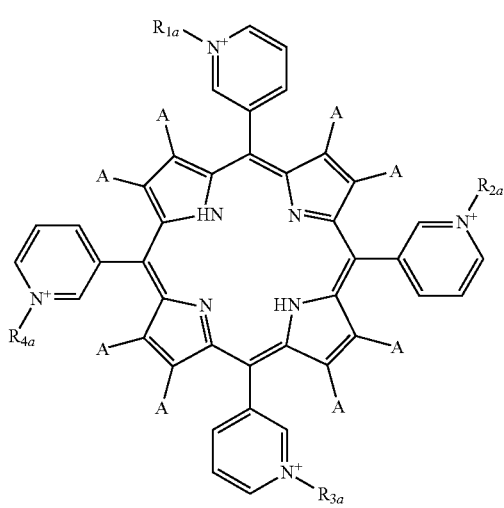

XIII

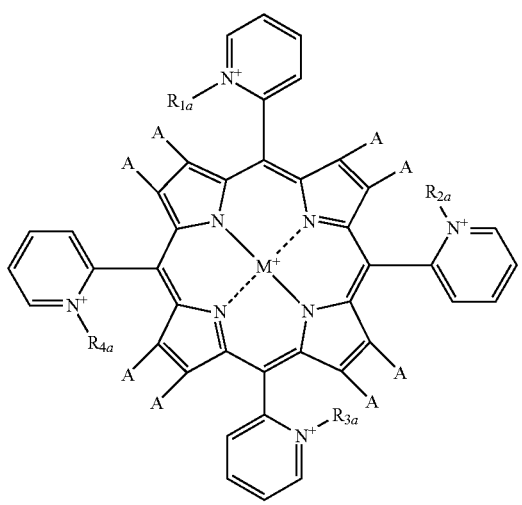

XIV

-continued

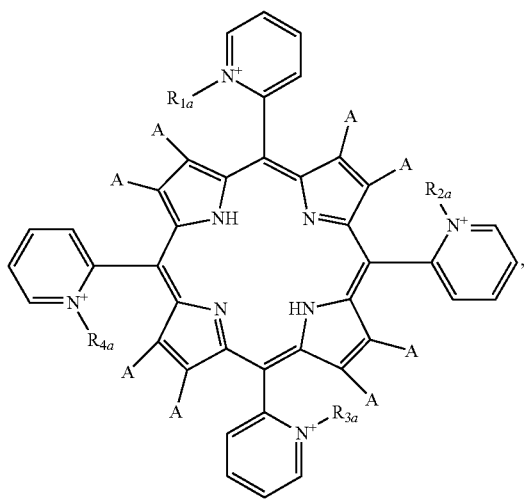

XV wherein $R_{1a}$, $R_{2a}$, $R_{3a}$, and $R_{4a}$ are independently —(CH$_2$)$_m$CH$_2$OX$_1$ or —(CH$_2$CH$_2$O)$_n$X$_1$; m is 1-6; n is 3-50; X$_1$ is substituted or unsubstituted C$_{1-12}$ alkyl; M is a metal; and each A is, independently, hydrogen or an electron withdrawing group; and c) a compound having the structure of one of Formulae (XVI)-(XVII),

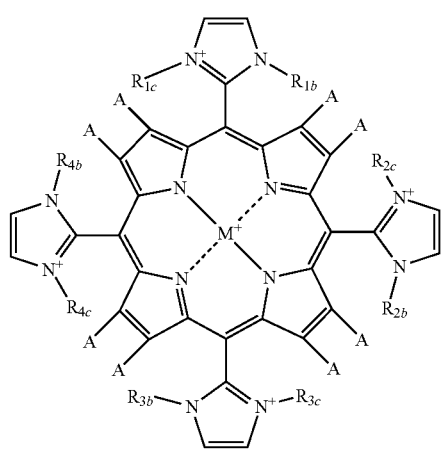

XVI

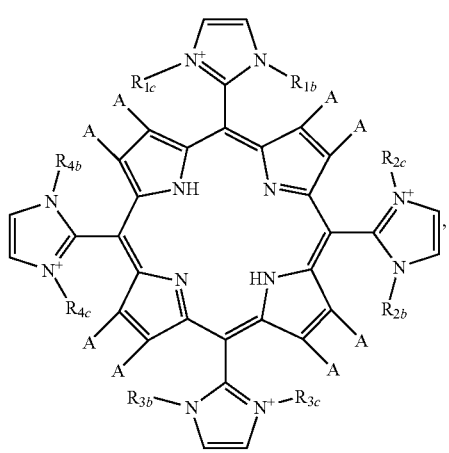

XVII wherein at least one of $R_{1b}$ or $R_{1c}$, $R_{2b}$ or $R_{2c}$, $R_{3b}$ or $R_{3c}$, and $R_{4b}$ or $R_{4c}$ is, independently, —(CH$_2$)$_p$CH$_2$OX$_2$ or —(CH$_2$CH$_2$O)$_q$X$_2$; the other one of $R_{1b}$ or $R_{1c}$, $R_{2b}$ or $R_{2c}$, $R_{3b}$ or $R_{3c}$, and $R_{4b}$ or $R_{4c}$ is, independently, a C$_{1-12}$ alkyl (straight chain or branched); p is 1-6; q is 3-50; X$_2$ is substituted or unsubstituted C$_{1-12}$ alkyl; M is a metal; and each A is, independently, hydrogen or an electron withdrawing group.

Embodiment 22

The method according to embodiment 21, wherein said brain injury results from seizure.

Embodiment 23

The method according to embodiment 22, wherein said brain injury is cognitive dysfunction.

Embodiment 24

The method according to embodiment 22, wherein said seizure results from exposure to a chemical threat agent.

Embodiment 25

The method according to any one of embodiments 1 or 24, wherein said chemical threat agent is an anti-cholinesterase agent.

Embodiment 26

The method according to any one of embodiments 1 or 24, further comprising administering to said subject an anticholinergic agent.

Embodiment 27

The method according any one of embodiments 1 or 24, further comprising administering to said subject an anti-seizure agent.

Embodiment 28

The method according to embodiment 27, wherein said anti-seizure agent is a benzodiazepine.

Embodiment 29

The method according any one of embodiments 1 or 24, further comprising administering to said subject an anticholinergic agent and an anti-seizure agent.

Embodiment 30

The method according any one of embodiments 1 or 24, further comprising administering to said subject an acetylcholinesterase reactivating agent.

Embodiment 31

The method according to embodiment 30, wherein said acetylcholinesterase reactivating agent is pralidoxime.

Embodiment 32

The method according any one of embodiments 1 or 24, wherein said administering occurs prior to said exposure to said chemical threat agent.

Embodiment 33

The method according to embodiment 32, wherein said administering occurs at least 30 minutes prior to said exposure to said chemical threat agent.

Embodiment 34

The method according to embodiment 21, wherein the effect of said reducing brain injury lasts for at least 90 minutes following said administration.

Embodiment 35

The method according to embodiment 21, wherein said compound has the structure of Formula (I) or Formula (II).

Embodiment 36

The method according to embodiment 35, wherein said compound has the structure of Formula (II).

Embodiment 37

The method according to embodiment 36, wherein said metal is manganese, iron, cobalt, copper, nickel, or zinc.

Embodiment 38

The method according to embodiment 37, wherein said metal is manganese.

Embodiment 39

The according to embodiment 35, wherein $R_1$, $R_2$, $R_3$, and $R_4$ are each

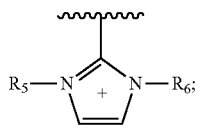

and $R_5$ and $R_6$ are independently unsubstituted alkyl.

Embodiment 40

The method according to embodiment 39, wherein said compound has the structure of Formula (VII)

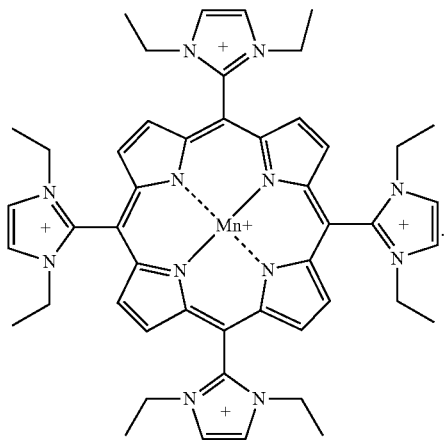

What is claimed is:

1. A method for treating exposure to a chemical threat agent in a subject so exposed, said method comprising administering to said subject an effective amount of a compound selected from:

a) a compound having the structure of Formula (I) or Formula (II),

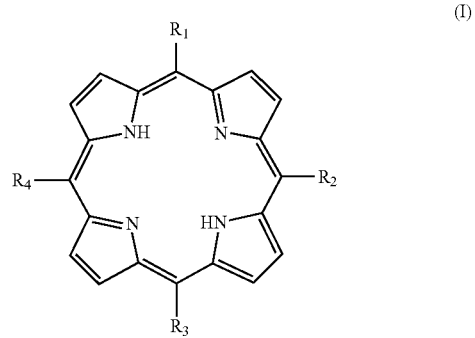

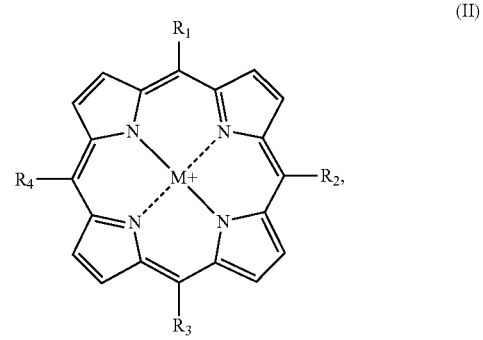

wherein $R_1$, $R_2$, $R_3$, and $R_4$ are each independently —$CF_3$, —$CO_2R_8$, —$COR_{8'}$,

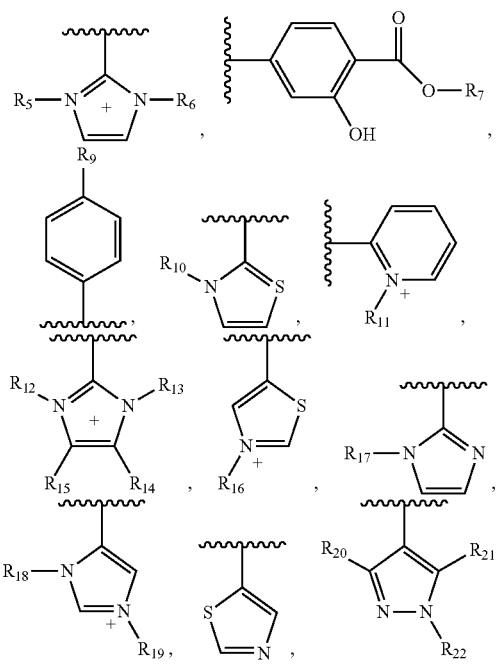

-continued

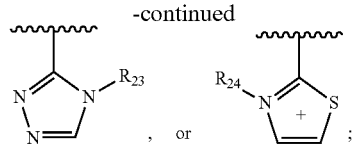

, or ;

R$_5$, R$_6$, R$_7$, R$_8$, R$_{8'}$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, and R$_{24}$ are each independently hydrogen, halogen, —CN, —CF$_3$, —OH, —NH$_2$, —COOH, —COOR$_{25}$, —CH$_2$COOR$_{25}$, —CH$_2$C OOH, an unsubstituted or substituted alkyl, unsubstituted or substituted heteroalkyl, unsubstituted or substituted cycloalkyl, unsubstituted or substituted heterocycloalkyl, unsubstituted or substituted aryl, or an unsubstituted or substituted heteroaryl;

R$_{25}$ is an unsubstituted alkyl; and

M is a metal;

b) a compound having the structure of one of Formulae (X)-(XV),

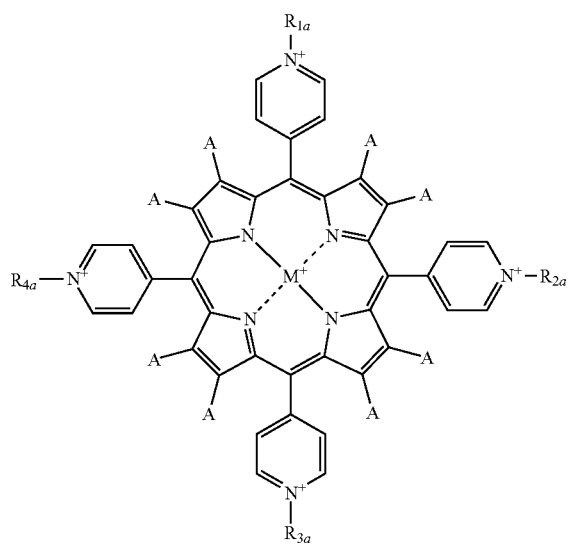

X

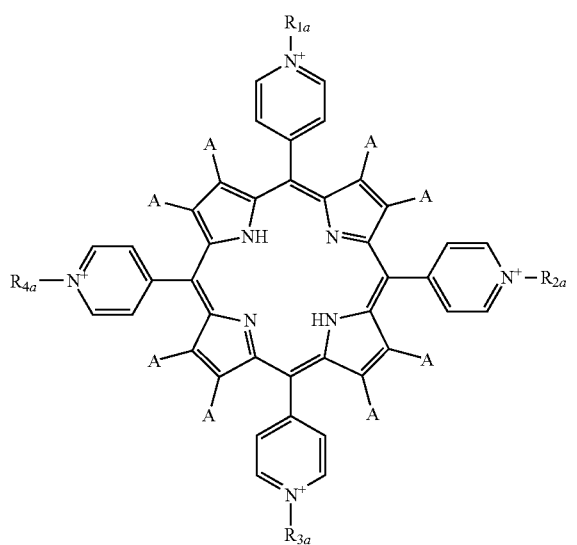

XI

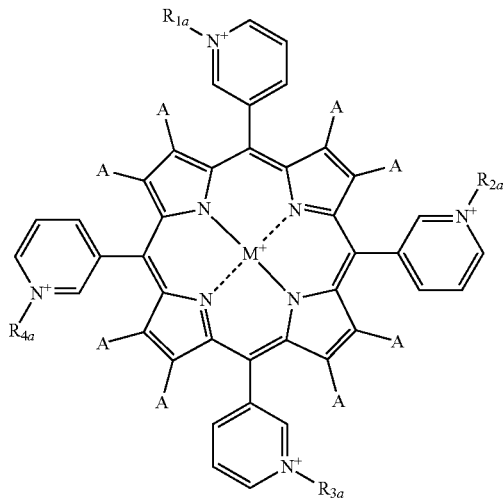

XII

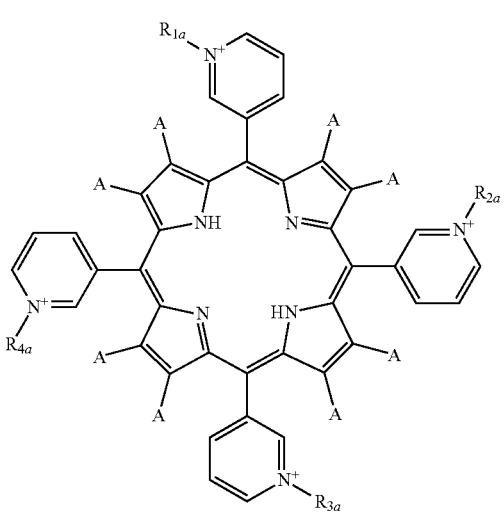

XIII

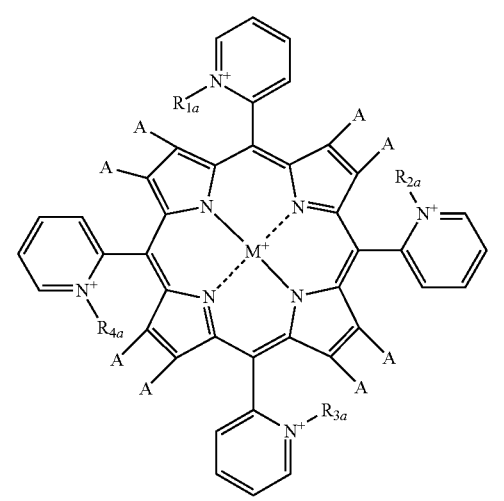

XIV

-continued

XV

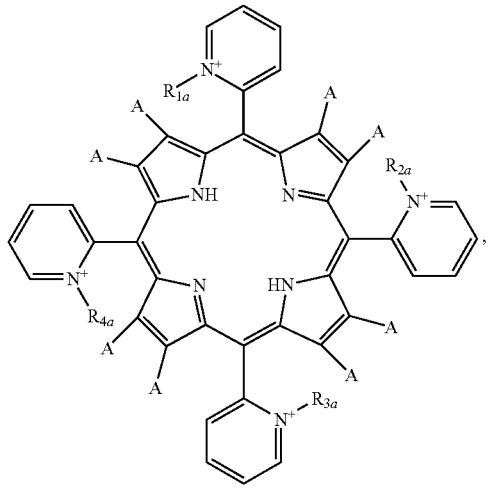

wherein
$R_{1a}$, $R_{2a}$, $R_{3a}$, and $R_{4a}$ are independently —$(CH_2)_m CH_2 OX_1$ or —$(CH_2CH_2O)_n X_1$;

m is 1-6;

n is 3-50;

$X_1$ is substituted or unsubstituted $C_{1-12}$ alkyl;

M is a metal; and each A is, independently, hydrogen or an electron withdrawing group; and c) a compound having the structure of one of Formulae (XVI)-(XVII),

XVI

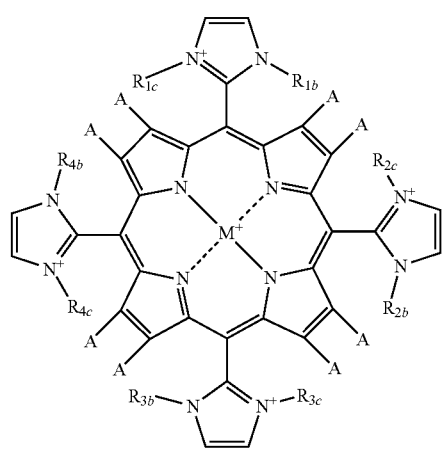

-continued

XVII

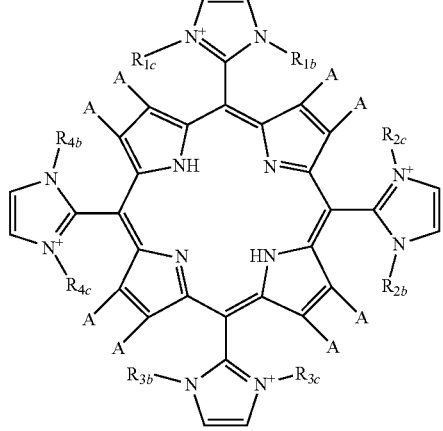

wherein
at least one of $R_{1b}$ or $R_{1c}$, $R_{2b}$ or $R_{2c}$, $R_{3b}$ or $R_{3c}$, and $R_{4b}$ or $R_{4c}$ is, independently, —$(CH_2)_p CH_2 OX_2$ or —$(CH_2CH_2O)_q X_2$;

the other one of $R_{1b}$ or $R_{1c}$, $R_{2b}$ or $R_{2c}$, $R_{3b}$ or $R_{3c}$, and $R_{4b}$ or $R_{4c}$ is, independently, a $C_{1-12}$ alkyl (straight chain or branched);

p is 1-6;

q is 3-50;

$X_2$ is substituted or unsubstituted $C_{1-12}$ alkyl;

M is a metal; and each A is, independently, hydrogen or an electron withdrawing group;

wherein said chemical threat agent is an anti-cholinesterase agent, a GABA-agent or a metabolic poison.

2. The method according to claim 1, wherein said compound has the structure of Formula (VII)

(VII)

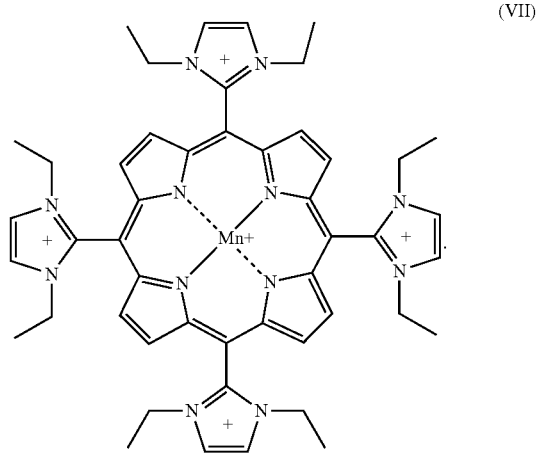

3. The method according to claim 1, wherein said compound has the structure of one of Formulae (X)-(XV).

4. The method according to claim 3, wherein said metal is manganese, iron, cobalt, copper, nickel, or zinc.

5. The method according to claim 4, wherein said metal is manganese.

6. The method according to claim 1, wherein said compound has the structure of one of Formulae (XVI)-(XVII).

7. The method according to claim 6, wherein said metal is manganese, iron, cobalt, copper, nickel, or zinc.

8. The method according to claim 7, wherein said metal is manganese.

9. The method according to claim 1, wherein said chemical threat agent causes seizures and neuropathology.

10. The method according to claim 9, wherein said chemical threat agent is a nerve agent.

11. The method according to claim 1, wherein said chemical threat agent targets the blood.

12. A method for reducing brain injury in a subject in need thereof, comprising administering to said subject an effective amount of a compound selected from:

a) a compound having the structure of Formula (I) or Formula (II),

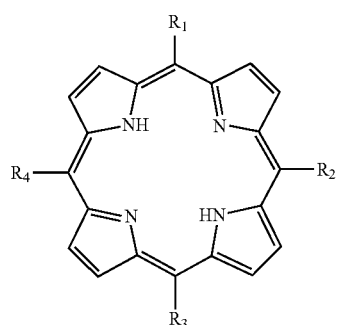
(I)

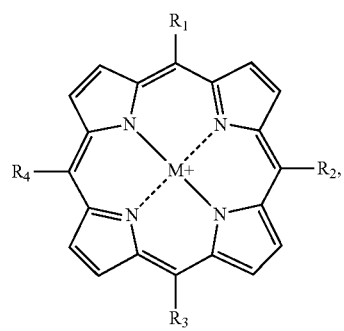
(II)

wherein $R_1$, $R_2$, $R_3$, and $R_4$ are each independently —$CF_3$, —$CO_2R_8$, —$COR_{8'}$,

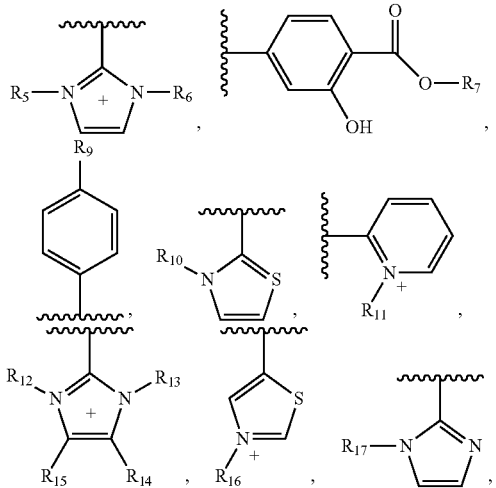

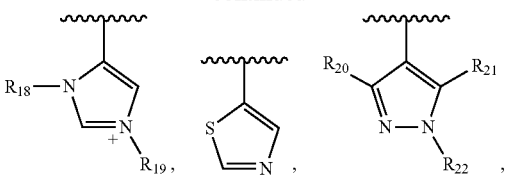

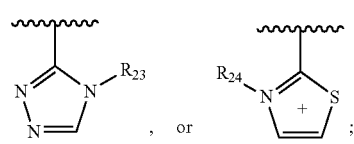

$R_5$, $R_6$, $R_7$, $R_8$, $R_{8'}$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are each independently hydrogen, halogen, —CN, —$CF_3$, —OH, —$NH_2$, —COOH, —$COOR_{25}$, —$CH_2COOR_{25}$, —$CH_2COOH$, an unsubstituted or substituted alkyl, unsubstituted or substituted heteroalkyl, unsubstituted or substituted cycloalkyl, unsubstituted or substituted heterocycloalkyl, unsubstituted or substituted aryl, or an unsubstituted or substituted heteroaryl;

$R_{25}$ is an unsubstituted alkyl; and

M is a metal;

b) a compound having the structure of one of Formulae (X)-(XV),

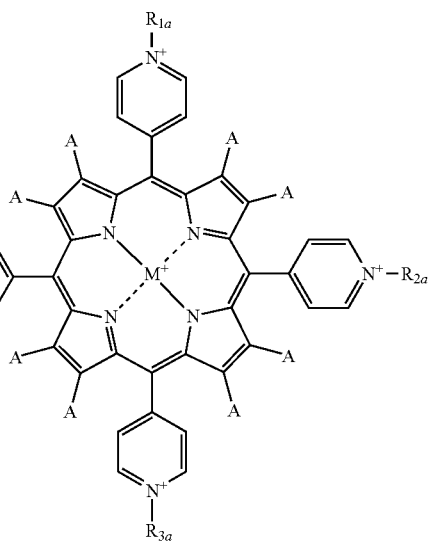
X

-continued
XI
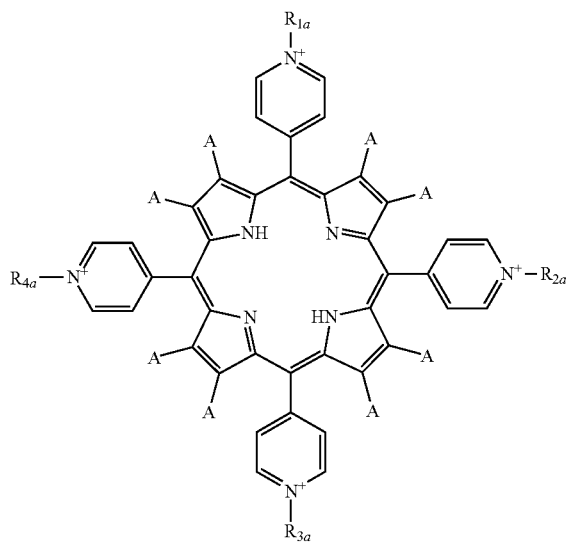
XII
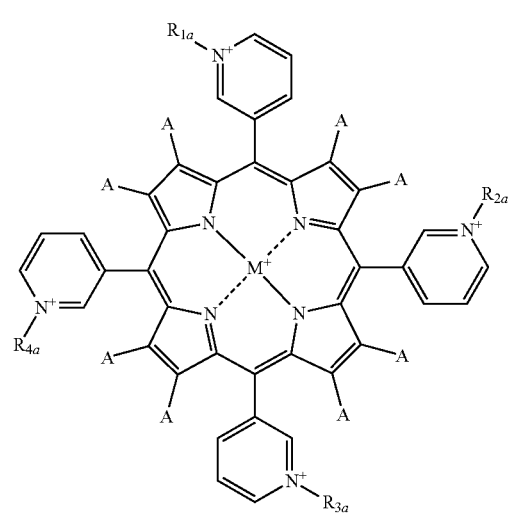
XIII
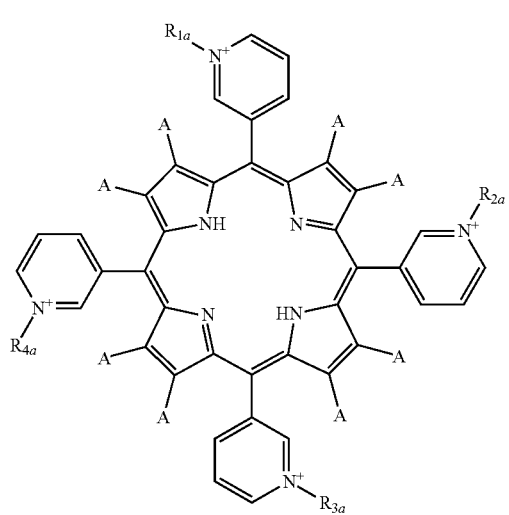
-continued
XIV
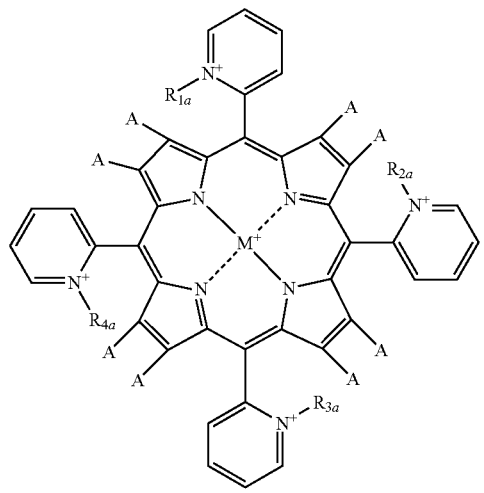
XV
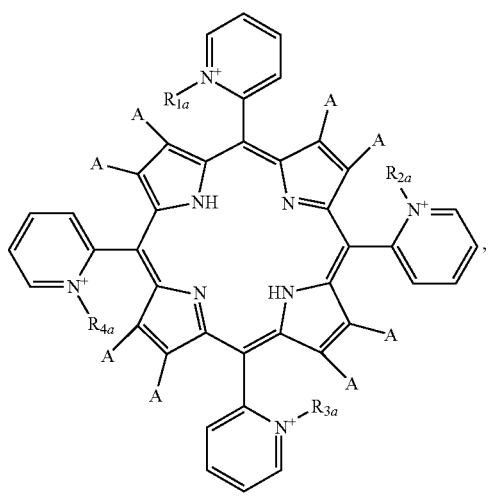
wherein
$R_{1a}$, $R_{2a}$, $R_{3a}$, and $R_{4a}$ are independently —$(CH_2)_m CH_2OX_1$ or —$(CH_2CH_2O)_n X_1$;
m is 1-6;
n is 3-50;
$X_1$ is substituted or unsubstituted $C_{1-12}$ alkyl;
M is a metal; and
each A is, independently, hydrogen or an electron withdrawing group; and c) a compound having the structure of one of Formulae (XVI)-(XVII),

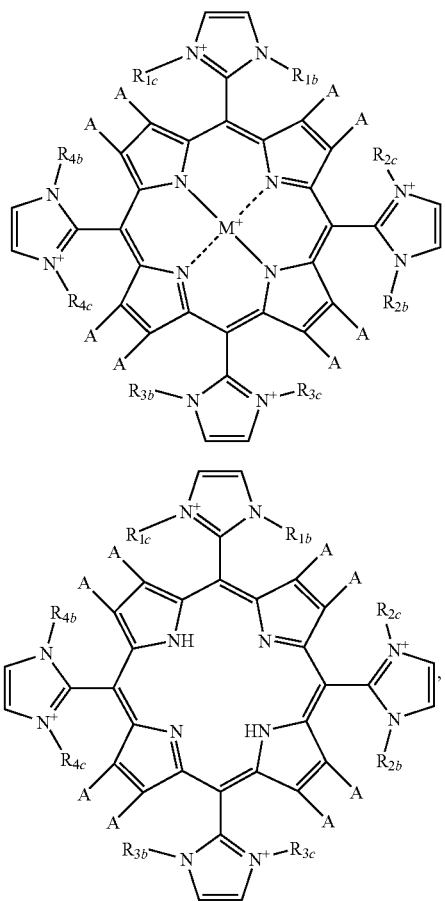

wherein
at least one of $R_{1b}$ or $R_{1c}$, $R_{2b}$ or $R_{2c}$, $R_{3b}$ or $R_{1c}$, and $R_{4b}$ or $R_{4c}$ is, independently, —(CH$_2$)$_p$CH$_2$OX$_2$ or —(CH$_2$CH$_2$O)$_q$X$_2$;
the other one of $R_{1b}$ or $R_{1c}$, $R_{2b}$ or $R_{2c}$, $R_{3b}$ or $R_{3c}$, and $R_{4b}$ or $R_{4c}$ is, independently, a $C_{1-12}$ alkyl (straight chain or branched);

p is 1-6;
q is 3-50;
$X_2$ is substituted or unsubstituted $C_{1-12}$ alkyl;
M is a metal; and
each A is, independently, hydrogen or an electron withdrawing group.

13. The method according to claim 12, wherein said compound has the structure of Formula (VII)

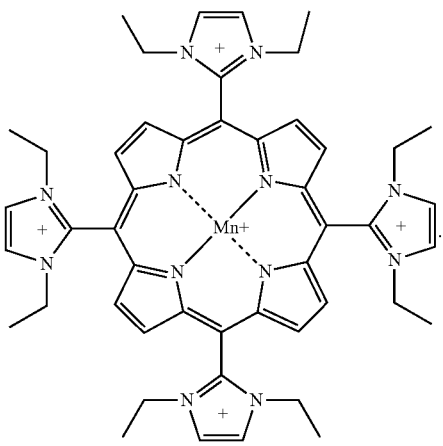

14. The method according to claim 12, wherein said brain injury results from seizure.

15. The method according to claim 14, wherein said seizure results from exposure to a chemical threat agent.

16. The method according to claim 15, wherein said chemical threat agent is an anti-cholinesterase agent.

17. The method according to claim 15, further comprising administering to said subject an anticholinergic agent.

18. The method according to claim 15, further comprising administering to said subject an anti-seizure agent.

19. The method according to claim 15, further comprising administering to said subject an anticholinergic agent and an anti-seizure agent.

20. The method according claim 15, wherein said administering occurs prior to said exposure to said chemical threat agent.

* * * * *